(12) United States Patent
Coffman et al.

(10) Patent No.: US 12,115,262 B2
(45) Date of Patent: Oct. 15, 2024

(54) PARTICLES COMPRISING A THERAPEUTIC OR DIAGNOSTIC AGENT AND SUSPENSIONS AND METHODS OF USE THEREOF

(71) Applicant: Elektrofi, Inc., Boston, MA (US)

(72) Inventors: Chase Coffman, Boston, MA (US); Lyndon Charles, Jr., Medford, MA (US); Paul Brown, Boston, MA (US); Daniel Benjamin Dadon, East Boston, MA (US); Lisa Liu, Somerville, MA (US); Sadiqua Shadbar, Allston, MA (US); Chaitanya Sudrik, Cambridge, MA (US)

(73) Assignee: Elektrofi, Inc., Boston, MA (US)

( * ) Notice: Subject to any disclaimer, the term of this patent is extended or adjusted under 35 U.S.C. 154(b) by 875 days.

(21) Appl. No.: 17/058,339

(22) PCT Filed: May 24, 2019

(86) PCT No.: PCT/US2019/033875
§ 371 (c)(1),
(2) Date: Nov. 24, 2020

(87) PCT Pub. No.: WO2019/226969
PCT Pub. Date: Nov. 28, 2019

(65) Prior Publication Data
US 2021/0220289 A1 Jul. 22, 2021

Related U.S. Application Data

(60) Provisional application No. 62/676,169, filed on May 24, 2018.

(51) Int. Cl.
*A61K 9/51* (2006.01)
*A61K 31/167* (2006.01)
*A61K 45/06* (2006.01)
*A61K 47/02* (2006.01)
*A61K 47/14* (2017.01)
*A61K 47/18* (2017.01)
*A61K 47/26* (2006.01)

(52) U.S. Cl.
CPC .......... *A61K 9/5192* (2013.01); *A61K 31/167* (2013.01); *A61K 45/06* (2013.01); *A61K 47/02* (2013.01); *A61K 47/14* (2013.01); *A61K 47/186* (2013.01); *A61K 47/26* (2013.01)

(58) Field of Classification Search
CPC .... A61K 9/5192; A61K 31/167; A61K 45/06; A61K 47/02; A61K 47/14; A61K 47/186; A61K 47/26; A61K 9/1611; A61K 9/1688
See application file for complete search history.

(56) References Cited

U.S. PATENT DOCUMENTS

| | | | |
|---|---|---|---|
| 3,013,007 | A | 12/1961 | Dale et al. |
| 3,882,036 | A | 5/1975 | Krezanoski et al. |
| 4,531,056 | A | 7/1985 | Labowsky et al. |
| 5,612,055 | A | 3/1997 | Bedford et al. |
| 5,840,731 | A | 11/1998 | Mayer et al. |
| 6,095,134 | A | 8/2000 | Sievers et al. |
| 8,013,022 | B2 | 9/2011 | DeAngelo et al. |
| 8,512,754 | B2 | 8/2013 | Needham |
| 8,939,388 | B1 | 1/2015 | Beetz et al. |
| 9,259,701 | B2 | 2/2016 | Palmer et al. |
| 11,654,112 | B2 | 5/2023 | Coffman et al. |
| 2002/0081732 | A1 | 6/2002 | Bowlin et al. |
| 2003/0055010 | A1 | 3/2003 | De Haan |
| 2005/0186183 | A1 | 8/2005 | DeAngelo et al. |
| 2006/0147400 | A1 | 7/2006 | Piot |
| 2008/0026068 | A1 | 1/2008 | Brown et al. |
| 2009/0035381 | A1 | 2/2009 | Stankus et al. |
| 2010/0092526 | A1 | 4/2010 | Baker, Jr. et al. |
| 2010/0092778 | A1 | 4/2010 | Watanabe et al. |
| 2010/0330169 | A1 | 12/2010 | Bunick et al. |
| 2012/0157591 | A1 | 6/2012 | Rufner et al. |
| 2014/0262694 | A1 | 9/2014 | Knigge |
| 2014/0263694 | A1 | 9/2014 | Lin et al. |
| 2014/0271843 | A1 | 9/2014 | Ma et al. |
| 2014/0303356 | A1 | 10/2014 | Gramer et al. |
| 2014/0378655 | A1 | 12/2014 | Anderson |
| 2015/0157576 | A1 | 6/2015 | Shum et al. |
| 2016/0271064 | A1 | 9/2016 | Sell et al. |

FOREIGN PATENT DOCUMENTS

| | | |
|---|---|---|
| CN | 1750811 A | 3/2006 |
| JP | 2013-166100 A | 8/2013 |
| WO | WO-2006/087354 A2 | 8/2006 |
| WO | WO-2010/082543 A1 | 7/2010 |
| WO | WO-2015/085898 A1 | 6/2015 |

(Continued)

OTHER PUBLICATIONS

Aniket et al., "MicroglassificationTM: A novel technique for protein dehydration," J Pharm Sci. 103(3): 810-820 (2014).
Banerjee et al., "Electrospray ionization mass spectrometry: a technique to access the information beyond the molecular weight of the analyte," Int J Anal Chem. Article 282574 (2012) (40 pages).
Bock et al., "Electrospraying of polymers with therapeutic molecules: state of the art," Prog Polym Sci. 37(11): 1510-1551(2012) (67 pages).
Bögelein et al., "Cyclone selection influences protein damage during drying in a mini spray-dryer," Int J Pharm. 401(1-2): 68-71 (2010).
Cloupeau et al., "Electrohydrodynamic spraying functioning modes: a critical review," J Aerosol Sci. 25(6): 1021-1036 (1994).

(Continued)

*Primary Examiner* — Robert A Wax
*Assistant Examiner* — Quanglong N Truong
(74) *Attorney, Agent, or Firm* — Hamilton, Brook, Smith & Reynolds, P.C.

(57) ABSTRACT

The invention provides particles, compositions including the particles, and methods of making the particles using electrospray. In certain embodiments, the particles allow for high concentrations of a therapeutic or diagnostic agent to be delivered at low viscosity. Particles may also exhibit beneficial properties with respect to stability.

19 Claims, 35 Drawing Sheets

(56) References Cited

FOREIGN PATENT DOCUMENTS

| WO | WO-2015/138844 A1 | 9/2015 |
|---|---|---|
| WO | WO-2015/196091 A1 | 12/2015 |

OTHER PUBLICATIONS

Cloupeau et al., "Electrostatic spraying of liquids: Main functioning modes," J Electrostat. 25(2): 165-184 (1990).
Dias et al., "Tolerability of High-Volume Subcutaneous Injections of a Viscous Placebo Buffer: A Randomized, Crossover Study in Healthy Subjects," AAPS PharmSciTech. 16(5): 1101-1107 (2015).
English translation of Office Action issued in Chinese Patent Application No. 201780072350.0, issued May 17, 2021 (16 pages).
Fenn et al., "Electrospray ionization for mass spectrometry of large biomolecules," Science. 246(4926):64-71 (Oct. 6, 1989).
Fernández de la Mora et al., "The current emitted by highly conducting taylor cones," J Fluid Mech. 260: 155-184 (1994).
Fernández de la Mora et al., "The fluid dynamics of Taylor cones," Annu Rev Fluid Mech. 39: 217-43 (2007) (29 pages).
Galam et al., "High-throughput assay for the identification of Hsp90 inhibitors based on Hsp90-dependent refolding of firefly luciferase," available in PMC Mar. 1, 2008, published in final edited form as: Bioorg Med Chem. 15(5): 1939-1946 (2007) (16 pages).
Gapinski et al., "Structure and dimensions of core-shell nanoparticles comparable to the confocal volume studied by means of fluorescence correlation spectroscopy," Langmuir. 32(10): 2482-2491 (2016).
Gañán-Calvo et al., "Current and droplet size in the electrospraying of liquids. Scaling laws," J Aerosol Sci. 28(2): 249-275 (1997).
Gikanga et al.,"Manufacturing of High-Concentration Monoclonal Antibody Formulations via Spray Drying—the Road to Manufacturing Scale," PDA J Pharm Sci Technol. 69(1): 59-73 (2015) (16 pages).
Giugliano et al., "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study," available in PMC Mar. 3, 2015, published in final edited form as: Lancet. 380(9858): 2007-17 (2012) (20 pages).
Haggag et al., "Evaluation of nano spray drying as a method for drying and formulation of therapeutic peptides and proteins," Front Pharmacol. 6:140 (2015) (5 pages).
International Search Report and Written Opinion for International Application No. PCT/US2019/033875, mailed Oct. 21, 2019 (15 pages).
Janssen Biotech Inc., "Highlights of prescribing information," <http://www.janssenlabels.com/package-insert/product-monograph/prescribing-information/DARZALEX-pi.pdf>, dated Jul. 2019, retrieved on Aug. 22, 2019 (13 pages).
Kaltashov et al., "Electrospray ionization mass spectrometry can provide estimates of protein surface areas in solution," available in PMC Jan. 27, 2009, published in final edited form as: Anal Chem. 77(16): 5370-5379 (2005) (21 pages).
Kim et al., "Controlled production of emulsion drops using an electric field in a flow-focusing microfluidic device," Appl Phys Lett. 91: 133106 (2007) (3 Pages).
Ku et al., "Electrospray characteristics of highly viscous liquids," J Aerosol Sci. 33(10): 1361-1378 (2002).
Lal et al., "Clean western blot signals from Immunoprecipitated samples," available in PMC Jan. 25, 2006, published in final edited form as: Mol Cell Probes. 19(6): 385-388 (2005) (5 pages).
Lavorini et al., "New inhaler devices—the good, the bad and the ugly," Respiration. 88(1): 3-15 (2014).
Lee et al., "Solid-state stabilization of a-Chymotrypsin and catalase with carbohydrates," Ind Eng Chem Res. 45(14): 5134-5147 (2006).
Lee, Spray-Drying of Proteins. *Rational Design of Stable Protein Formulations*. Carpenter and Manning, 135-158 (2002).
Li et al., "Effects of pulsed electric fields and heat treatment on stability and secondary structure of bovine immunoglobulin G," J Agric Food Chem. 53(3): 663-670 (2005).
Longman et al., "Identifying differences in solution Conformations of two chimeric IgG3 antibodies through triple detection SEC," LCGC Europe. 18(12): (2005) (10 pages).
Loscertales et al., "Micro/nano encapsulation via electrified coaxial liquid jets," Science. 295(5560): 1695-8 (2002).
López-Herrera et al., "Coaxial jets generated from electrified Taylor cones. Scaling laws," J Aerosol Sci. 34(5): 535-552 (2003).
Makadia et al., "Poly lactic-co-glycolic acid (PLGA) as biodegradable controlled drug delivery carrier," Polymers (Basel). 3(3): 1377-1397 (2011).
Mardles. E. W. J., "Viscosity of Suspensions and the Einstein Equation," Nature. 145: 970 (Jun. 22, 1940).
Miller et al., "Antibody nanoparticle dispersions formed with mixtures of crowding molecules retain activity and in vivo bioavailability," available in PMC Oct. 1, 2013, published in final edited form as: J Pharm Sci. 101(10): 3763-3778 (2012) (25 pages).
Miller et al., "Low viscosity highly concentrated injectable nonaqueous suspensions of lysozyme microparticles," available in PMC Feb. 17, 2011, published in final edited form as: Langmuir. 26(2): 1067-1074 (2010) (22 pages).
Moghadam et al., "Electro-spray of high viscous liquids for producing mono-sized spherical alginate beads," Particuology. 6(4): 271-275 (2008).
Morales-Cruz et al., "Two-step nanoprecipitation for the production of protein-loaded PLGA nanospheres," Results Pharma Sci. 2: 79-85 (2012).
Mueller et al., "The rheology of suspensions of solid particles," Proc R Soc A. 466: 1201-1228 (2010).
Naqvi et al., "Living cell factories—electrosprayed microcapsules and microcarriers for minimally invasive delivery," Adv Mater. 28(27): 5662-71 (2015) (10 pages).
Nema et al., *Pharmaceutical Dosage Forms: Parenteral Medications, Third Edition*, vol. 3: *Regulations, Validation and the Future*. Informa Healthcare, vii-304 (2010) (328 pages).
Nguyen et al., "Pharmaceutical applications of electrospraying," J Pharm Sci. 105(9): 2601-2620 (2016).
Park et al., "One step immobilization of protein encapsulated core/shell particles onto nanofibers," Macromol Mater Eng. 295(6): 544-550 (2010).
Patel et al., "Poloxamers: a pharmaceutical excipients with therapeutic behaviors," International Journal of PharmTech Research. 1(2):299-303 (2009).
Saglam et al., "Preparation of high protein micro-particles using two-step emulsification," Food Hydrocolloids. 25(5):1139-48 (2011).
Shire et al., "Challenges in the development of high protein concentration formulations," J Pharm Sci. 93(6): 1390-402 (2004).
Supplementary Partial European Search Report for European Patent Application No. 17873547.8, mailed Jun. 15, 2020 (9 pages).
Takáts et al., "Electrosonic spray ionization. A gentle technique for generating folded proteins and protein complexes in the gas phase and for studying ion-molecule reactions at atmospheric pressure," Anal Chem. 76(14): 4050-58 (2004).
Torchilin, "Multifunctional nanocarriers," Adv Drug Deliv Rev. 58(14): 1532-55 (2006).
U.S. Department of Health and Human Services, "Q3C—Tables and List: Guidance for Industry," Aug. 2018 (10 pages).
Vehring, "Pharmaceutical particle engineering via spray drying," Pharm Res. 25(5): 999-1022 (2008).
Vonhoff, Sebastian, Thesis: "The Influence of Atomization Conditions on Protein Secondary and Tertiary Structure During Microparticle Formation by Spray-Freeze-Drying," PhD, Univ. of Erlangen-Nuremberg, 2010 (195 pages).
Wang et al., "FDA's regulatory science program for generic PLA/PLGA-based drug products," Am Pharm Rev. <https://www.americanpharmaceuticalreview.com/Featured-Articles/188841-FDA-s-Regulatory-Science-Program-for-Generic-PLA-PLGA-Based-Drug-Products/>, dated Jun. 15, 2016, retrieved on Aug. 22, 2019 (5 pages).
Wanning et al., "Pharmaceutical spray freeze drying," Int J Pharm. 488(1-2): 136-53 (2015).

(56) References Cited

OTHER PUBLICATIONS

Xie et al., "Encapsulation of protein drugs in biodegradable microparticles by co-axial electrospray," J Colloid Interface Sci. 317(2): 469-76 (2008).
Yuan et al., "Coaxial electrospray of curcumin-loaded microparticles for sustained drug release," PLoS One. 10(7): e0132609 (2015) (15 pages).
Yuan et al., "One-step fabrication of triple-layered microcapsules by a tri-axial flow focusing device for microencapsulation of soluble drugs and imaging agents," Proc SPIE vol. 9711, Imaging, Manipulation, and Analysis of Biomolecules, Cells, and Tissues IX (2016) (12 pages).
Zhang et al., "Coaxial electrospray of microparticles and nanoparticles for biomedical applications," Expert Rev Med Devices. 9(6): 595-612 (2012).
Zhang et al., "Coaxial electrospray of ranibizumab-loaded microparticles for sustained release of anti-VEGF therapies," PloS One. 10(8):e0135608 (2015) (16 pages).
Ziabicki et al., "Crystal nucleation in an electric field," Macromol Symp. 104(1): 65-87 (1996).

| Technology | Particle counts/mL | Adjusted counts/mL* |
|---|---|---|
| Control Sample | 734,578 | --- |
| Particles of the Invention | 1,229,299 | 494,721 |

Fig. 31

PARTICLES COMPRISING A THERAPEUTIC OR DIAGNOSTIC AGENT AND SUSPENSIONS AND METHODS OF USE THEREOF

STATEMENT OF FEDERALLY SPONSORED RESEARCH

This invention is made with government support under grant No. 1722066 awarded by the National Science Foundation. The government has certain rights to this invention.

TECHNICAL FIELD

The present invention relates to electrospray techniques for producing active particles with reduced aggregation, fragmentation and change in charge variants of the active agent. In particular, the invention relates to compositions of the particles that are suitable for high-concentration formulations. The invention also relates to the administration of the particle formulations.

BACKGROUND OF THE INVENTION

There is an urgent and unmet need for therapeutic and diagnostic formulations which are reliable, convenient, and cost-effective to administer. This is particularly true in relation to therapeutic proteins, e.g., monoclonal antibodies, which are increasingly important in the treatment of a wide range of life-threatening and debilitating diseases. Desirable formulations comprise a high concentration of therapeutic or diagnostic agents and confer appropriate stability, such that a minimal volume of the formulation can be used to administer a high dose of the agents. In some cases, this helps to curtail the time to deliver the required dose and the pain or discomfort experienced by the patient. In some cases, this may also help to decrease the frequency of administration of the agents. Such formulation attributes are, however, typically unattainable in aqueous solution. High concentrations of aqueous therapeutic or diagnostic agents are often typified by high fluid dynamic viscosity, precluding the use of standard injection devices, while degradation of the active ingredient proceeds through one or several pathways at an accelerated rate.

SUMMARY OF THE INVENTION

In one aspect, the invention provides a method of forming particles by electrospraying, e.g., conventional electrospraying, a stream of a first liquid including a first therapeutic or diagnostic agent toward a collector (e.g., another liquid), the particles being collected on the collector, the concentration of the first therapeutic or diagnostic agent in the liquid ranging from 0.0001 to 1000 mg/mL, e.g., 1 to 1000 mg/mL, 1 to 900 mg/mL, 1 to 500 mg/mL, 1 to 250 mg/mL, 1 to 100 mg/mL, 1 to 50 mg/mL, 5 to 1000 mg/mL, 100 to 900 mg/mL, 150 to 800 mg/mL, or 200 to 700 mg/mL, and the viscosity of the liquid ranging from 0.1 to 5000 cP, e.g., 0.75 to 1.5 cP, 0.1 to 1000 cP, 0.1 to 100 cP, 1 to 5000 cP, 10 to 1000 cP, or 100 to 500 cP. In some embodiments, the invention provides a method of forming particles by electrospraying an annular stream of an encapsulant in a second liquid toward the collector, and centrally with respect to the annular steam of encapsulant, electrospraying a stream of the first liquid. In some embodiments, an encapsulant is in the first liquid.

In another aspect, the invention provides a method of electrospraying, e.g., conventional electrospraying, a first liquid including a first therapeutic or diagnostic agent to form droplets and removing (e.g., evaporating) the first liquid to produce particles from the droplets. The therapeutic or diagnostic agent in the particles has 0.5 to 1.0 activity per unit, e.g., 0.75 to 1.0 activity per unit, or 0.9 to 1.0 activity per unit.

In either method, the method may further include suspending the particles in a pharmaceutically acceptable medium, thereby forming a pharmaceutical composition. Alternatively, the particles may be formulated as a pharmaceutical composition in dry form, e.g., a powder.

In some embodiments, the particles in suspension have less than 10% aggregation of the first diagnostic or therapeutic agent, e.g., less than 9, 8, 7, 6, 5, 4, 3, 2, 1, or 0.5%. In other embodiments, the particles in suspension have less than 10% fragmentation of the first diagnostic or therapeutic agent, e.g., less than 9, 8, 7, 6, 5, 4, 3, 2, 1, or 0.5%. In certain embodiments, the particles in suspension have less than 50% change in charge variants of the first diagnostic or therapeutic agent, e.g., less than 40, 30, 20, 10, 9, 8, 7, 6, 5, 4, 3, 2, 1, or 0.5%, compared to the agent prior to particle formation.

In some embodiments, the encapsulant includes poly (vinyl alcohol), poly(acrylic acid), poly(acrylamide), poly (ethylene oxide), poly(lactic acid), poly(glycolic acid), polycaprolactone, poly(lactic-co-glycolic acid), chitosan, cellulose, or any combination thereof. In some embodiments, the encapsulant is any excipient, therapeutic agent, or diagnostic agent.

In other embodiments, the first liquid is aqueous, an organic solvent, an ionic liquid, a hydrogel, an ionogel, or a combination thereof. Organic solvents include benzyl alcohol, benzyl benzoate, castor oil, coconut oil, corn oil, cottonseed oil, fish oil, grape seed oil, hazelnut oil, hydrogenated palm seed oil, olive oil, peanut oil, peppermint oil, safflower oil, sesame oil, soybean oil, sunflower oil, vegetable oil, walnut oil, polyethylene glycol, glycofurol, acetone, diglyme, dimethylacetamide, dimethyl isosorbide, dimethyl sulfoxide, ethanol, ethyl acetate, ethyl ether, ethyl lactate, isopropyl acetate, methyl acetate, methyl isobutyl ketone, methyl tert-butyl ether, N-methyl pyrrolidone, perfluorodecalin, 2-pyrrolidone, trigylcerides, tetrahydrofurfuryl alcohol, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP (diethylene glycol monoethyl ether), solketal, isosorbide dimethyl ether, ethyl formate, ethyl hexyl acetate, and any combination thereof. In some embodiments, the organic solvent is polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP (diethylene glycol monoethyl ether), solketal, isosorbide dimethyl ether, ethyl formate, ethyl hexyl acetate, or a combination including one or more of these organic solvents. Aqueous liquids include water, 0.9% saline, lactated Ringer's solution, dextrose 5%, and buffers (e.g., acetate buffer, histidine buffer, succinate buffer, HEPES buffer, tris buffer, carbonate buffer, citrate buffer, phosphate buffer, glycine buffer, barbital buffer, and cacodylate buffer). The liquid may further include another component, such as a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, nutrient media, a paraben, a bactericide, a fungicide, or a vitamin. In some embodiments, other components of the liquid include a paraben, a bactericide, a fungicide, or a vitamin. In further embodiments, the liquid may include an analgesic, such as lidocaine or acetaminophen. In some embodiments, the first liquid can further include an analgesic, such as acetaminophen or lidocaine. In some embodiments, each of the other components is, independently, at 0.0001 to 99% (w/v) of sprayed liquid, e.g., at 0.0001 to 90% (w/v), at 0.0001 to 50% (w/v), at 0.0001 to 10% (w/v), at 0.0001 to 1% (w/v), or at 0.0001 to 0.1% (w/v). One of ordinary skill in the art would be able to determine an appropriate amount of the other components in the sprayed liquid. Carbohydrates include dextran, trehalose, sucrose, agarose, mannitol, lactose, sorbitol, and maltose. The pH adjusting agent may be, e.g., acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. Salts include sodium chloride, calcium chloride, potassium chloride, sodium hydroxide, stannous chloride, magnesium sulfate, sodium glucoheptonate, sodium pertechnetate, or guanidine hydrochloride. The chelator can be, e.g., disodium edetate or ethylenediaminetetraacetic acid. The mineral can be, e.g., calcium, zinc, or titanium dioxide. Suitable polymers include propyleneglycol, glucose star polymer, silicone polymer, polydimethylsiloxane, polyethylene glycol, carboxymethylcellulose, poly(glycolic acid), poly(lactic-co-glycolic acid), and polylactic acid. The surfactant can be, e.g., polysorbate, magnesium stearate, sodium dodecyl sulfate, polyethylene glycol nonylphenyl ether (TRITON™ N-101), glycerin, or polyoxyethylated castor oil. Protein stabilizers include acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids (e.g., an oligopeptide), hydroxyethylstarch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, or mannitol. The emulsifier can be, e.g., polysorbate 80, polysorbate 20, sorbitan monooleate, sorbitan monopalmitate, sorbitan monostearate, sorbitan tristearate, sorbitan trioleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In preferred embodiments, the emulsifier can be polysorbate 80 or sorbitan monooleate. Antiseptics include phenol, m-cresol, benzyl alcohol, 2-phenyloxyethanol, chlorobutanol, neomycin, benzethonium chloride, gluteraldehyde, or beta-propiolactone. The amino acid may be, e.g., alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, or glutamine, e.g., asparagine, L-arginine, histidine, glycine, or glutamine. The antioxidant can be, e.g., glutathione, ascorbic acid, cysteine, or tocopherol. The protein can be, e.g., protamine, protamine sulfate, or gelatin. The organic solvent can be dimethyl sulfoxide or N-methyl-pyrrolidone, N-ethyl-pyrrolidone, or a mixture thereof. Suitable preservatives include methyl hydroxybenzoate, thimerosal, parabens, formaldehyde, and castor oil. The paraben can be a parahydroxybenzoate. The bactericide can be benzalkonium chloride. The liquid may further include adenine, tri-n-butyl phosphate, octa-fluoropropane, white petrolatum, or p-aminophenyl-p-anisate. Exemplary ionic liquids may contain pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6^-$, $BF_4^-$, triflate, nonaflate, bis(trifyl)amide, trifluoroacetate, heptafluorobutanoate, haloaluminate, or any combination thereof. Exemplary hydrogels or ionogels are collagen hydrogels, chitosan hydrogels, methylcellulose hydrogels, dextran hydrogels, alginate hydrogels, agarose hydrogels, poly(methyl methacrylate) hydrogels, poly(amido amine) hydrogels, poly(ethyleneimine) hydrogels, polyethylene oxide hydrogels, gelatin hydrogels, hyaluronic acid hydrogels, and any combinations thereof.

In certain embodiments, the reconstituted particles in suspension have less than 10% aggregation of the first diagnostic or therapeutic agent, e.g., less than 9, 8, 7, 6, 5, 4, 3, 2, 1, or 0.5%. In other embodiments, the reconstituted particles in suspension have less than 10% fragmentation of the first diagnostic or therapeutic agent, e.g., less than 9, 8, 7, 6, 5, 4, 3, 2, 1, 0.5%.

In some embodiments, the reconstituted particles in suspension have less than 50% change in charge variants of the first diagnostic or therapeutic agent, e.g., less than 40, 30, 20, 10, 9, 8, 7, 6, 5, 4, 3, 2, 1, or 0.5%, compared to the agent prior to particle formation.

In some embodiments, the pharmaceutical composition has a concentration of the first therapeutic or diagnostic agent from 0.0001 to 1000 mg/mL, e.g., 100 to 800, 200 to 700, 200 to 600, or 300 to 700 mg/mL.

In some embodiments, the pharmaceutical composition includes a second therapeutic or diagnostic agent, e.g., at a concentration from 0.0001 to 1000 mg/mL. The first and second therapeutic or diagnostic agents can be the same or different.

In other embodiments, the pharmaceutical composition further comprises insoluble particulate matter larger than or equal to 1 μm.

In some embodiments, a composition of the invention may include insoluble particulate matter larger than or equal to 1 μm in size. In some cases, the number of insoluble particles is from 0 to 100,000,000 per mL, e.g., less than 10,000,000, 1,000,000, 100,000, 10,000, 1000, 100, 10, or 1 per mL. For example, the number of insoluble particles greater than 10 μm is from 0 to 6,000 per mL, e.g., less than 5,000, 4,000, 3,000, 2,000, 1,000, 500, 100, 10, or 1 per mL, and/or the number of insoluble particles greater than 25 μm is from 0 to 600 per mL, e.g., less than 500, 400, 300, 200, 100, 50, 10, or 1 per mL. Therapeutic and diagnostic agents include nucleic acids, oligonucleotides, antibodies (or fragment thereof), amino acids, peptides, proteins, cells, bacteria, gene therapeutics, genome engineering therapeutics, epigenome engineering therapeutics, carbohydrates, chemical drugs, contrast agents, magnetic particles, polymer beads, metal nanoparticles, metal microparticles, quantum dots, antioxidants, antibiotic agents, hormones, nucleoproteins, polysaccharides, glycoproteins, lipoproteins, steroids, analgesics, local anesthetics, anti-inflammatory agents, antimicrobial agents, chemotherapeutic agents, exosomes, outer membrane vesicles, vaccines, viruses, bacteriophages, adjuvants, vitamins, minerals, organelles, and any combination thereof.

In some embodiments, any of a second liquid being electrosprayed, a liquid collector, or suspension medium is aqueous, an organic solvent, an ionic liquid, a hydrogel, ionogel, or a combination thereof. Organic solvents for use in the medium include benzyl alcohol, benzyl benzoate, castor oil, coconut oil, corn oil, cottonseed oil, fish oil, grape seed oil, hazelnut oil, hydrogenated palm seed oil, olive oil, peanut oil, peppermint oil, safflower oil, sesame oil, soybean oil, sunflower oil, vegetable oil, walnut oil, polyethylene glycol, glycofurol, acetone, diglyme, dimethylacetamide, dimethyl isosorbide, dimethyl sulfoxide, ethanol, ethyl acetate, ethyl ether, ethyl lactate, isopropyl acetate, methyl acetate, methyl isobutyl ketone, methyl tert-butyl ether, N-methyl pyrrolidone, perfluorodecalin, 2-pyrrolidone, trigylcerides, tetrahydrofurfuryl alcohol, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP (diethylene glycol monoethyl ether), Solketal, isosorbide dimethyl ether, ethyl formate, ethyl hexyl acetate, and any combination thereof. In some embodiments, the organic solvent for use in the medium is polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP (diethylene glycol monoethyl ether), Solketal, isosorbide dimethyl ether, ethyl formate, ethyl hexyl acetate, or a combination including one or more of these organic solvents. Exemplary aqueous liquids are water, 0.9% saline, lactated Ringer's solution, dextrose 5%, and buffers (e.g., acetate buffer, histidine buffer, succinate buffer, HEPES buffer, tris buffer, carbonate buffer, citrate buffer, phosphate buffer, glycine buffer, barbital buffer, and cacodylate buffer). The medium may further include another component, such as a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, or nutrient media. In other embodiments, the medium can further include an analgesic, such as acetaminophen or lidocaine. In certain embodiments, the aqueous medium can further include an analgesic, such as acetaminophen or lidocaine. In some embodiments, other components of the liquid include a paraben, a bactericide, a fungicide, or a vitamin. In certain embodiments, the liquid may include an analgesic, such as lidocaine or acetaminophen. In some embodiments, each of the other components is, independently, at 0.0001 to 99% (w/v) of the liquid, e.g., at 0.0001 to 90% (w/v), at 0.0001 to 50% (w/v), at 0.0001 to 10% (w/v), at 0.0001 to 1% (w/v), or at 0.0001 to 0.1% (w/v). One of ordinary skill in the art would be able to determine an appropriate amount of the other components in the liquid. Carbohydrates include dextran, trehalose, sucrose, agarose, mannitol, lactose, sorbitol, or maltose. pH adjusting agents include acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. Salts include sodium chloride, calcium chloride, potassium chloride, sodium hydroxide, stannous chloride, magnesium sulfate, sodium glucoheptonate, sodium pertechnetate, or guanidine hydrochloride. An exemplary chelator is disodium edetate. Minerals include calcium, zinc, and titanium dioxide. Polymers include propyleneglycol, glucose star polymer, silicone polymer, polydimethylsiloxane, polyethylene glycol, carboxymethylcellulose, poly(glycolic acid), poly(lactic-co-glycolic acid), and polylactic acid. Surfactants include polysorbate, magnesium stearate, sodium dodecyl sulfate, polyethylene glycol nonylphenyl ether (TRITON™ N-101), glycerin, or polyoxyethylated castor oil. Protein stabilizers include acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids (e.g., an oligopeptide), hydroxyethylstarch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, or mannitol. The emulsifier can be, e.g., polysorbate 80, polysorbate 20, sorbitan monooleate, sorbitan monopalmitate, sorbitan monostearate, sorbitan tristearate, sorbitan trioleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In preferred embodiments, the emulsifier can be polysorbate 80 or sorbitan monooleate. Antiseptics include phenol, m-cresol, benzyl alcohol, 2-phenyloxyethanol, chlorobutanol, neomycin, benzethonium chloride, gluteraldehyde, and beta-propiolactone. The amino acid may be, e.g., alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, or glutamine, e.g., asparagine, L-arginine, histidine, glycine, glutamine, or a combination thereof. Suitable antioxidants include glutathione, ascorbic acid, cysteine, and tocopherol. The protein can be protamine, protamine sulfate, or gelatin. The organic solvent can be dimethyl sulfoxide, N-ethyl-pyrrolidone, N-methyl-pyrrolidone, or mixtures thereof. The preservative can be, e.g., methyl hydroxybenzoate, thimerosal, parabens, formaldehyde, or castor oil. The paraben can be a parahydroxybenzoate. The bactericide can be benzalkonium chloride. The medium may further include, e.g., adenine, tri-n-butyl phosphate, octa-fluoropropane, white petrolatum, or p-aminophenyl-p-anisate. Ionic liquids may contain, e.g., pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6^-$, $BF_4^-$, triflate, nonaflate, bis(trifyl)amide, trifluoroacetate, heptafluorobutanoate, haloaluminate, or any combination thereof. Exemplary hydrogels or ionogels are collagen hydrogels, chitosan hydrogels, methylcellulose hydrogels, dextran hydrogels, alginate hydrogels, agarose hydrogels, poly(methyl methacrylate) hydrogels, poly (amido amine) hydrogels, poly(ethyleneimine) hydrogels, polyethylene oxide hydrogels, gelatin hydrogels, hyaluronic acid hydrogels, and any combinations thereof.

In certain embodiments, the amount of additional compound, i.e., excipient, present in the first liquid, second, liquid, collecting liquid, or medium, is as shown in the following table. The percentages are as a percentage of the total solute loading by weight. For a first liquid with a therapeutic at a concentration of 10 mg/mL and an excipient at a concentration of 5 mg/mL, e.g., the weight fraction of the excipient, relative to the total solute population, is 33%.

| Excipient | Range 1 | Range 2 | Range 3 | Range 4 |
| --- | --- | --- | --- | --- |
| Carbohydrate | 10-30% | 3-50% | 1-80% | 0.3-99% |
| pH adjusting agent | 0.5-5% | 0.2-40% | 0.05-70% | 0.01-99% |
| Salt | 10-50% | 3-70% | 1-85% | 0.3-99% |
| Chelator | 0.01-1% | 0.003-40% | 0.001-80% | 0.0003-99% |
| Mineral | 10-50% | 3-70% | 1-80% | 0.3-99% |
| Polymer | 10-60% | 3-75% | 1-85% | 0.3-99% |
| Surfactant | .01-1% | 0.003-40% | 0.001-80% | 0.0003-99% |
| Protein stabilizer | 10-70% | 3-70% | 1-85% | 0.3-99% |
| Emulsifier | .01-1% | 0.003-40% | 0.001-80% | 0.0003-99% |
| Antiseptic | .5-10% | 0.2-50% | 0.05-70% | 0.02-99% |
| Amino acids | 10-25% | 3-50% | 1-85% | 0.3-99% |
| Antioxidant | 0.01-1% | 0.003-40% | 0.001-80% | 0.0003-99% |
| Protein | 1-10% | 0.3-50% | 0.1-75% | 0.03-99% |
| Organic solvent | 0.001-2% | 0.0003-1% | 0.0001-10% | 0.00003-99% |
| Nutrient media | 10-50% | 3-70% | 1-85% | 0.3-99% |
| Paraben | 0.01-5% | 0.005-10% | 0.001-50% | 0.001-99% |
| Bactericide | 0.01-5% | 0.005-10% | 0.001-50% | 0.001-99% |
| Fungicide | 0.01-5% | 0.005-10% | 0.001-50% | 0.001-99% |
| Vitamin | 1-50% | 1-70% | 0.1-85% | 0.01-99% |
| Analgesic | 0.01-5% | 0.005-10% | 0.001-50% | 0.001-99% |

For second liquids, collecting liquids, and medium, Range 4 may be to 100% for any excipient listed in the table.

In some embodiments, the particles have less than 10% aggregation of the first diagnostic or therapeutic agent, e.g., less than 9, 8, 7, 6, 5, 4, 3, 2, 1, or 0.5%. In other embodiments, the particles have less than 10% fragmentation of the first diagnostic or therapeutic agent, e.g., less than 9, 8, 7, 6, 5, 4, 3, 2, 1, or 0.5%. In certain embodiments, the particles have less than 50% change in charge variants of the first diagnostic or therapeutic agent, e.g., less than 40, 30, 20, 10, 9, 8, 7, 6, 5, 4, 3, 2, 1, or 0.5%, compared to the agent prior to particle formation.

In some embodiments, the particles have diameters from 0.1 to 1000 μm, e.g., 1 to 400 μm, 1 to 200 μm, 1 to 100 μm, 1 to 50 μm, 1 to 25 μm, 1 to 10 μm, 10 to 100 μm, 50 to 100 μm, 50 to 75 μm, or 75 to 100 μm.

In certain embodiments, the particles have a polydispersity index from 0.05 to 0.9.

In some embodiments, the pharmaceutical composition has a viscosity from 0.27 to 200 cP, e.g., 0.27 to 100 cP, 0.27 to 50 cP, 0.27 to 30 cP, 20 to 50 cP, 1 to 30 cP, 1 to 20 cP, or 1 to 15 cP.

In certain embodiments, the pharmaceutical composition includes from 5 to 90% particles by volume, e.g., 20 to 90%, 40 to 80%, 50 to 60%, or 70 to 90%.

In some embodiments, the composition further comprises insoluble particulate matter larger than or equal to 1 μm.

In a related aspect, the invention provides a composition including particles made by a method of the invention.

In another aspect, the invention provides a method of administering a first therapeutic or diagnostic agent by administering a pharmaceutical composition including particles made by a method of the invention.

In another aspect, the invention provides a method of administering a first therapeutic or diagnostic agent to a mammal. The method includes administering an effective amount of a pharmaceutical composition to the mammal. In certain embodiments, the pharmaceutical composition includes a medium and particles including the therapeutic or diagnostic agent, where the pharmaceutical composition has a viscosity from 0.27 to 200 cP, e.g., 0.27 to 100 cP, 0.27 to 50 cP, 0.27 to 30 cP, 20 to 50 cP, 1 to 30 cP, 1 to 20 cP, or 1 to 15 cP, and a concentration of the first therapeutic or diagnostic agent from 0.0001 to 1000 mg/mL, e.g., 100 to 800, 200 to 700, 200 to 600, or 300 to 700 mg/mL. In other embodiments, the pharmaceutical composition is a dry form of particles including the therapeutic or diagnostic agent. In a related aspect, the invention provides a composition, e.g., a pharmaceutical composition, including particles including a first therapeutic or diagnostic agent. In certain embodiments, the composition further includes a medium, where the composition has a viscosity from 0.27 to 200 cP, e.g., 0.27 to 100 cP, 0.27 to 50 cP, 0.27 to 30 cP, 20 to 50 cP, 1 to 30 cP, 1 to 20 cP, or 1 to 15 cP, and a concentration of the first therapeutic or diagnostic agent from 0.0001 to 1000 mg/mL, e.g., 100 to 800, 200 to 700, 200 to 600, or 300 to 700 mg/mL. In other embodiments, the composition includes particles in dry form.

In some embodiments, the composition includes from 5 to 90% particles by volume, e.g., 20 to 90%, 40 to 80%, 50 to 60%, or 70 to 90%.

The administering may occur by auricular, buccal, conjunctival, cutaneous, dental, electro-osmotical, endocervical, endosinusial, endotracheal, enteral, epidural, extra amniotical, extracorporeal, infiltration, interstitial, intra-abdominal, intra-amniotical, intra-arterial, intra-articular, intrabiliary, intrabronchial, intrabursal, intracameral, intracardial, intracartilaginous, intracaudal, intracavernous, intracavitary, intracerebral, intracisternal, intracorneal, intracoronal, intracoronary, intracorporus cavernosum, intradermal, intradiscal, intraductal, intraduodenal, intradural, intraepidermal, intraesophageal, intragastrical, intragingival, intrailleal, intralesional, intraluminal, intralymphatical, intramedullar, intrameningeal, intramuscular, intraocular, intraovarian, intrapericardial, intraperitoneal, intrapleural, intraprostatical, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastrical, occlusive dressing technique, ophthalmical, oral, oropharyngeal, parenteral, percutaneous, periarticular, peridural, perineural, periodontal, rectal, inhalation, retrobulbar, soft tissue, subarachnoidial, subconjunctival, subcutaneous, sublingual, submucosal, topical, transdermal, transmucosal, transplacental, transtracheal, transtympanic, ureteral, urethral, or vaginal administration.

In particular embodiments, the administration is by small volume injection (SVI).

In some embodiments of any aspect of the invention, the viscosity is measured at a shear rate in the Newtonian regime. In other embodiments, the viscosity is measured at a shear rate of 100 s$^{-1}$ or greater, e.g., at 1000 s$^{-1}$, or greater than 1000 s$^{-1}$, or greater than 10,000 s$^{-1}$ or greater than 50,000 s$^{-1}$.

In some embodiments, the concentration of the first therapeutic or diagnostic agent in the first liquid is from 0.0001 to 1000 mg/mL, e.g., 1 to 1000 mg/mL, 1 to 900 mg/mL, 1 to 500 mg/mL, 1 to 250 mg/mL, 1 to 100 mg/mL, 1 to 50 mg/mL, 5 to 1000 mg/mL, 100 to 900 mg/mL, 150 to 800 mg/mL, or 200 to 700 mg/mL.

In another aspect, the invention provides a method of administering a first therapeutic or diagnostic agent to a mammal. The method includes administering an effective amount of a suspension or a dry formulation of the particles including the therapeutic or diagnostic agent to the mammal, where the first therapeutic or diagnostic agent has 0.5 to 1.0 activity per unit, e.g., 0.75 to 1.0 activity per unit, or 0.9 to 1.0 activity per unit (e.g., about 0.99 activity per unit). In a related aspect, the invention provides a composition including particles including a first therapeutic or diagnostic agent has 0.5 to 1.0 activity per unit, e.g., 0.75 to 1.0 activity per unit, or 0.9 to 1.0 activity per unit. The composition may be a suspension of the particles in a non-aqueous or aqueous liquid. Alternatively, the composition is in dry form, e.g., a powder, such as for inhalation or needleless injection. The composition may be in the form of a pharmaceutical composition in which the first therapeutic or diagnostic agent is present in an effective amount.

In some embodiments, the suspension has viscosity from 0.27 to 200 cP, e.g., 0.27 to 100 cP, 0.27 to 50 cP, 0.27 to 30 cP, 20 to 50 cP, 1 to 30 cP, 1 to 20 cP, or 1 to 15 cP.

In some embodiments, the suspension includes from 5 to 90% particles by volume, e.g., 20 to 90%, 40 to 80%, 50 to 60%, or 70 to 90%.

In some embodiments, the suspension has a concentration of the first therapeutic or diagnostic agent from 0.0001 to 1000 mg/mL, e.g., 100 to 800, 200 to 700, 200 to 600, or 300 to 700 mg/mL.

In some embodiments, the liquid in a suspension or a dry formulation includes a second therapeutic or diagnostic agent, e.g., at a concentration from 0.0001 to 1000 mg/mL. The first and second therapeutic or diagnostic agents can be the same or different. In other embodiments, the suspension or dry formulation is administered by small volume injection (SVI). In certain embodiments, the suspension further comprises insoluble particulate matter larger than or equal to 1 μm.

The present methods may be useful for producing active particles and compositions of active particles with reduced aggregation of the active agent. The present methods may also be useful for administering the particle formulations. In preferred embodiments, the particles have less than 10% fragmentation of the first diagnostic or therapeutic agent. In certain preferred embodiments, the particles have less than 50% change in charge variants of the first diagnostic or therapeutic agent compared to the agent prior to particle formation.

Definitions

The term "activity" refers to the ratio of a functional or structural aspect of a therapeutic or diagnostic agent at two points in time. The denominator of the ratio corresponds to a measure of the functional or structural aspect of the therapeutic or diagnostic agent in the feed solution, immediately in advance of electrospray particle formation. The numerator of the ratio corresponds to the same measure of a functional or structural aspect of the therapeutic or diagnostic agent at a later point in time, e.g., immediately after electrospray particle formation. In certain embodiments, the activity of a protein is assessed through SEC-HPLC or the proclivity of the protein for binding select targets.

The term "conventional electrospray" is used to refer to an electrospray produced with an assembly comprising a capillary tube, a hydraulic pump, a power supply, and a counter-electrode. The capillary tube and counter-electrode are coordinated at a distance from one another and disposed in a dielectric medium. The power supply connects the tube to the counter-electrode in an electrical fashion, such that a relative electrical bias can be enforced. This produces an electric field, the agency of which facilitates an electrospray when the pump is used to eject a liquid from the end of the capillary tube.

A "dry" particle component, i.e., a dry core or a dry shell, including the therapeutic or diagnostic agents, has undergone a desiccation step or series of desiccation steps, such that its moisture or solvent content is substantially reduced in relation to that which prevailed before any desiccation. In some embodiments, the residual moisture or solvent content of the dry component is less than about 10% by weight, e.g., less than about 5% by weight. Exemplary methods for the measurement of moisture content include chemical titration methods, e.g., Karl Fischer titration involving a vacuum oven. A variety of solvents, including water, may also be measured using weight loss methods involving thermal excitation. Exemplary methods include thermogravimetric analysis with Infrared spectroscopy (TGA-IR).

The term "electrospray" refers to a process by which droplets of a first liquid are formed in a dielectric medium in the presence of an electric field. Suitable dielectric media include vacuo, air, and a second liquid which is at least partially immiscible with the first liquid. The droplets need not be electrically charged (e.g., droplets can be formed from electrically insulating liquids, such as oils), and the electric field need not be the primary driving force behind the formation of the droplets. In some embodiments, the droplets are produced by a conventional electrospray (M. Cloupeau and B. Prunet-Foch, J. Aerosol Sci., vol. 25, no. 6, pp. 1021-1036, 1994; J. F. de la Mora, Annu. Rev. Fluid Mech., vol. 39: 217-243, 2007). In other embodiments, the droplets are formed by an atomizer, e.g., a pneumatic nozzle atomizer (Z. Takats, J M Wiseman, B. Gologan, and R G Cooks, Anal. Chem., 2004, 76 (14), pp. 4050-4058), under an electric field. In other embodiments, the droplets are formed by a microfluidic device, e.g., a T-junction (H. Kim, D. Luo, D. Link, D. Weitz, M. Marquez, and Z. Cheng, Appl. Phys. Lett., 91, 133106, 2007), under an electric field. In some embodiments, electrospraying is a gentle method of atomization that is used to generate the particles. In some embodiments, in electrospraying, liquid or gel (or pre-gel) is pumped from a supply through a capillary nozzle into an electric field formed at the opening of the nozzle causing the liquid or gel (or pre-gel) to be dispersed away from the nozzle as a uniform particle aerosol.

The term "electrospray particle formation" refers to the process of electrospraying a first liquid including a solute to form droplets and then removing the first liquid to form particles including the solute. Removal of the first liquid, or desiccation, can be performed with one of several methods known in the art, or some combination thereof. In some embodiments, desiccation is carried out by contacting the droplets with a stream of hot gas, such as in spray drying (B. Gikanga, R. Turok, A. Hui, M. Bowen, O. B. Stauch, Y. Maa, J. Pharm Sci. Tech., 2015, 69, 59-73). In other embodiments, desiccation is carried out by freezing the droplets and then subliming the first liquid, such as in spray freeze drying (S. Wanning, R. Suverkrup, A. Lamprecht, Int. J. Pharm., 2015, 488, 136-153). In other embodiments, desiccation is carried out by contacting the first liquid with a second liquid, in which it is at least partially miscible, thereby causing the solute to precipitate, such as in certain microfluidic systems (Aniket, D. A. Gaul, D. L. Rickard, D. Needham J. Pharm. Sci., 2014, 103, 810-820).

The term "encapsulant" refers to a substance that can be dried or gelled around a particle core to form a shell.

The term "excipient" refers to an additive to a preparation of formulation, the agency of which may be useful in achieving a desired modification to the characteristics of the preparation or formulation. Such modifications include, but are not limited to, physical stability, chemical stability, and therapeutic efficacy. Exemplary excipients include, but are not limited to, a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, or nutrient media.

The term "feed solution" refers to a preparation of the therapeutic or diagnostic agents in the first liquid, either as a solution, a slurry, or some other liquid form. In some embodiments, the preparation contains excipients and, optionally, a buffer.

The term "injectability" refers to the relative ease with which a liquid formulation can be administered to a subject through the use of an injection device. In some embodiments, the injectability is determined by measuring the viscosity of the formulation at various shear rates. In some embodiments, the injectability is determined by measuring the breakaway and/or glide forces required to actuate a standard injection device consisting of a syringe barrel, a plunger, and, optionally, a needle. In some embodiments, the injectability of the suspension formulation is superior to that of an aqueous formulation with about the same concentration of therapeutic or diagnostic agents.

The term "injection breakaway force" refers to the force required to overcome friction between the syringe barrel and plunger of a standard injection device before ejection of the contents of the syringe can take place at a steady rate. The force is applied at the outward-facing end of the syringe plunger shaft and directed along the axis of the syringe barrel. The contents of the syringe are optionally ejected through a syringe needle of prescribed gauge and length. In some embodiments, the injection breakaway force is measured through a load cell placed at the outward-facing end of the syringe plunger during actuation.

The term "injection glide force" refers to the force required to maintain a steady ejection of the contents of a standard injection device. The force is applied at the outward-facing end of the syringe plunger shaft and directed along the axis of the syringe barrel. The contents of the syringe are optionally ejected through the tip of a syringe needle of prescribed gauge and length. In some embodiments, the injection glide force is measured through a load cell placed at the outward-facing end of the syringe plunger during actuation.

The term "medium" refers to a liquid in which particles are dispersed.

The term "Newtonian regime" means a range of shear rates over which the highest and lowest values of viscosity differ by at most 1% of the highest value.

The term "particle" refers to a quantity of therapeutic or diagnostic material which, in one aspect, is in a state of matter that is substantially solid as compared to a liquid droplet, or in a gel form. In some embodiments, the particle includes a core and a shell, where the shell is viewed as an encapsulant. In other embodiments, the particle does not include a shell, in which case, the particle is made up entirely of a core.

The term "pharmaceutical composition" denotes a composition in which a therapeutic or diagnostic agent retains, or partially retains, its intended biological activity or functional form, and in which only pharmaceutically acceptable components are included.

A "pharmaceutically acceptable" component, e.g., an excipient, is a component which is suitable for administration to a subject, e.g., a human.

The term "powder formulation" refers to a solid formulation including solid particles in the absence of a carrier liquid. In some embodiments, the powder formulation is suitable for powder injection, e.g., with a Portal PRIME device.

The term "Rayleigh limit" refers to the specific charge, e.g., in units of Coulombs per kilogram, corresponding to the point at which Coulombic repulsion overcomes the binding forces of surface tension in a drop, leading to Coulomb fission.

The term "stabilizer" refers to an excipient or a mixture of excipients which stabilizes the physical and/or chemical properties of the pharmaceutical formulation. In some embodiments, stabilizers prevent, e.g., degradation of the therapeutic or diagnostic agents during electrospray, desiccation, and/or storage of the particulate matter. Exemplary stabilizers include, but are not limited to, sugars, salts, hydrophobic salts, detergents, reducing agents, cyclodextrins, polyols, carboxylic acids, and amino acids. A "stable" formulation refers to a formulation in which the therapeutic or diagnostic agent retains an acceptable portion of its essential physical and/or chemical and/or biological properties over an acceptable period of time. In the case of proteins and peptides, e.g., exemplary methods of assessing stability are reviewed in (i) Peptide and Protein Drug Delivery, 247-301, Vincent Lee Ed., Marcel Dekker, Inc., New York, NY, 1991, and (ii) Jones, A., Adv. Drug Delivery Rev. 10: 29-90 (1993). In certain embodiments, chemical stability of a protein is assessed by measuring the size distribution of the sample at several stages. These include, e.g., before particle formation (assessment of the feed solution), immediately after particle formation, and again after a period of storage, where storage takes place either within or in the absence of a suspension formulation carrier medium. In certain embodiments, the size distribution is assessed by size exclusion chromatography (SEC-HPLC).

A "sterile" formulation is aseptic or free from living microorganisms and their spores.

The term "suspension formulation" refers a liquid formulation including solid particles disposed within a carrier liquid in which they are not soluble on an appropriate timescale. The particles may settle over time, i.e., the physical stability of the suspension is not indefinite, but may be re-suspended using a form of agitation or excitation.

A "therapeutic amount" refers to an amount of a therapeutic or diagnostic agent required to produce the desired effect.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

The term "viscosity" is used to describe the property of a fluid acting to resist shearing flow. For the purposes of the present invention, viscosity can be determined using a rheometer, e.g., AR-G2 Rheometer (TA Instruments, USA), fitted with a cone and plate (2°/40 mm) at 25° C. at a specified shear rate. In certain embodiments, the viscosity is measured at a shear rate in the Newtonian regime. In other embodiments, the viscosity is measured at a shear rate of 100 $s^{-1}$ or greater, e.g., at 1000 $s^{-1}$ or greater than 1000 $s^{-1}$.

Figure 1:
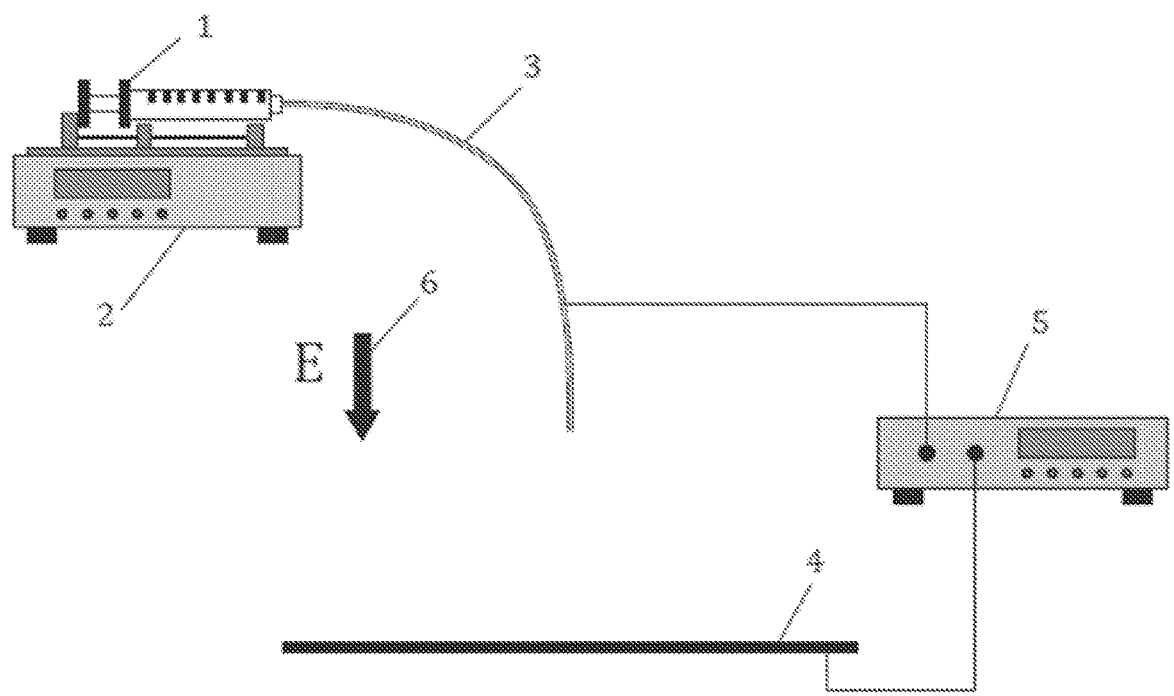
FIG. 1 shows a basic electrospray assembly. One end of a tube 3 is disposed a distance from an electrode 4 while the other end attaches to a syringe 1, controlled by a syringe pump 2. A power supply 5 charges the tube 3 relative to the electrode 4, creating an electric field 6 in the region between the two.
Figure 2:
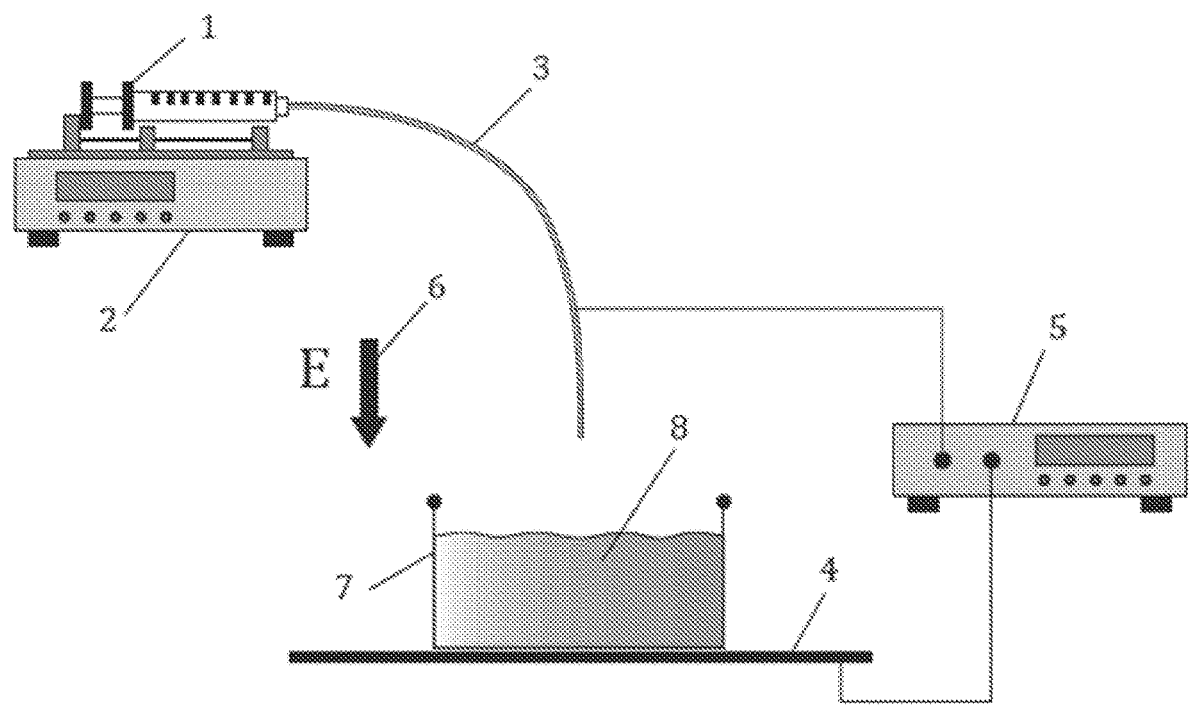
FIG. 2 shows a basic electrospray assembly in which a bath 7 containing a liquid 8 is disposed between an end of the tube 3 and an electrode 4. The end of the tube 3 is not immersed in the liquid 8.
Figure 3:
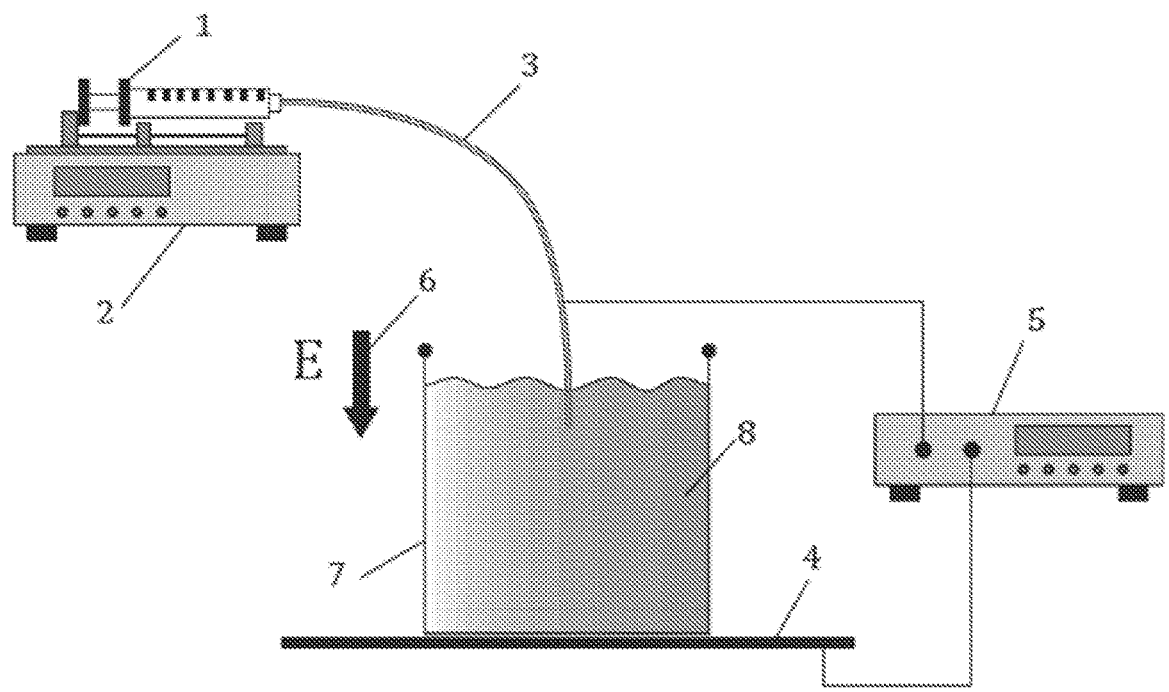
FIG. 3 shows a basic electrospray assembly in which a bath 7 containing a liquid 8 is disposed between an end of the tube 3 and an electrode 4. The end of the tube 3 is immersed in the liquid 8.
Figure 4:
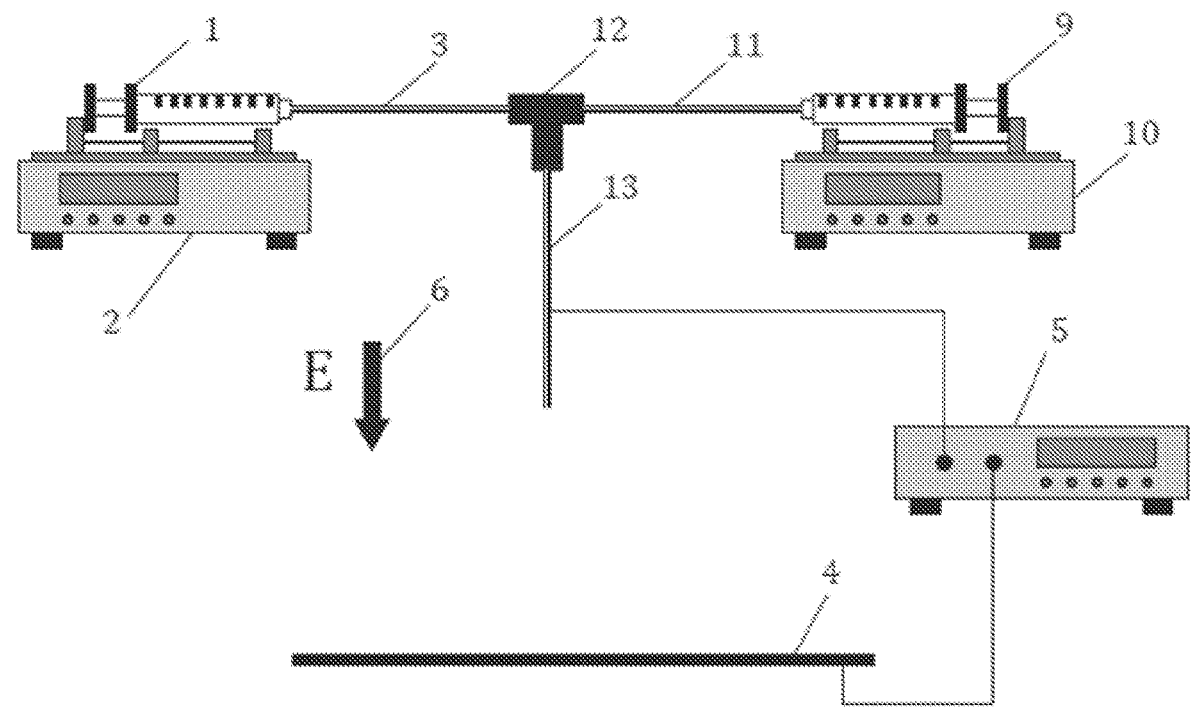
FIG. 4 shows a coaxial electrospray assembly. A tube 3 connects to a syringe 1, controlled by a syringe pump 2. A second tube 11 connects to a second syringe 9, controlled by a syringe pump 10.

The distal ends of tubes 3 and 11 connect to an adapter 12 that outputs a coaxial tube 13, an end of which is disposed a distance from an electrode 4. A power supply 5 charges the coaxial tube 13 relative to the electrode 4, creating an electric field 6 in the region between the two.

Figure 5:
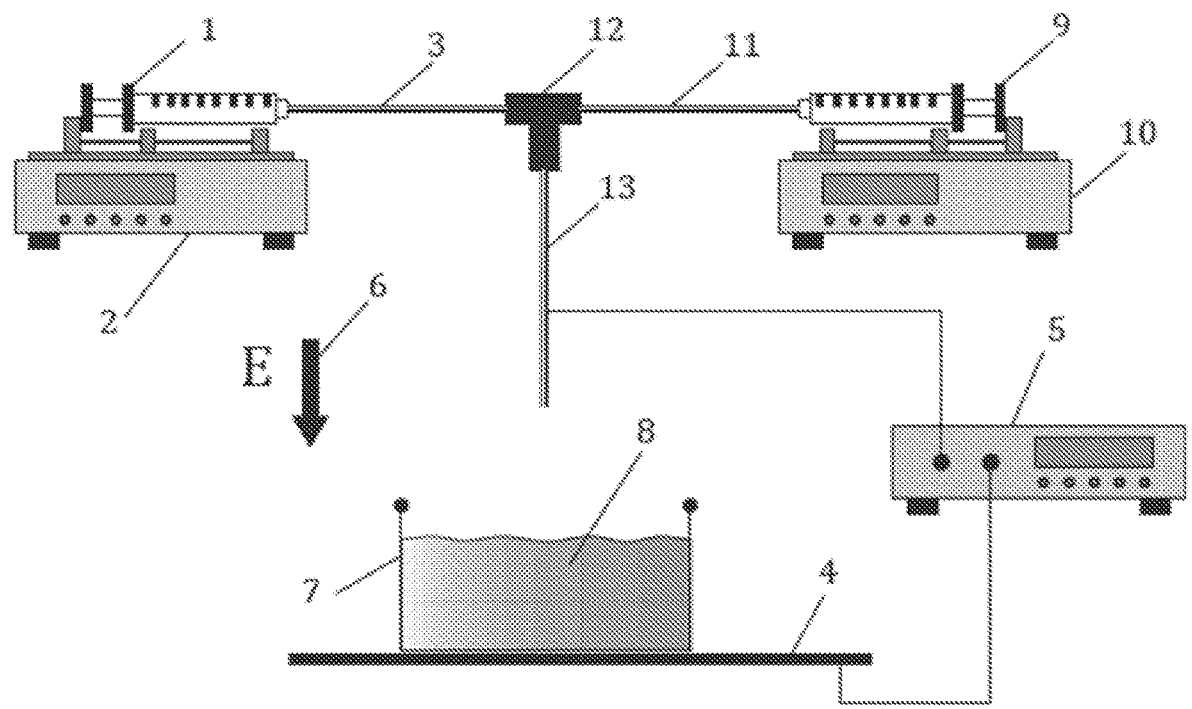

FIG. 5 shows a coaxial electrospray assembly in which a bath 7 containing a liquid 8 is disposed between an end of the tube 13 and an electrode 4. The end of the tube 13 is not immersed in the liquid 8.

Figure 6:
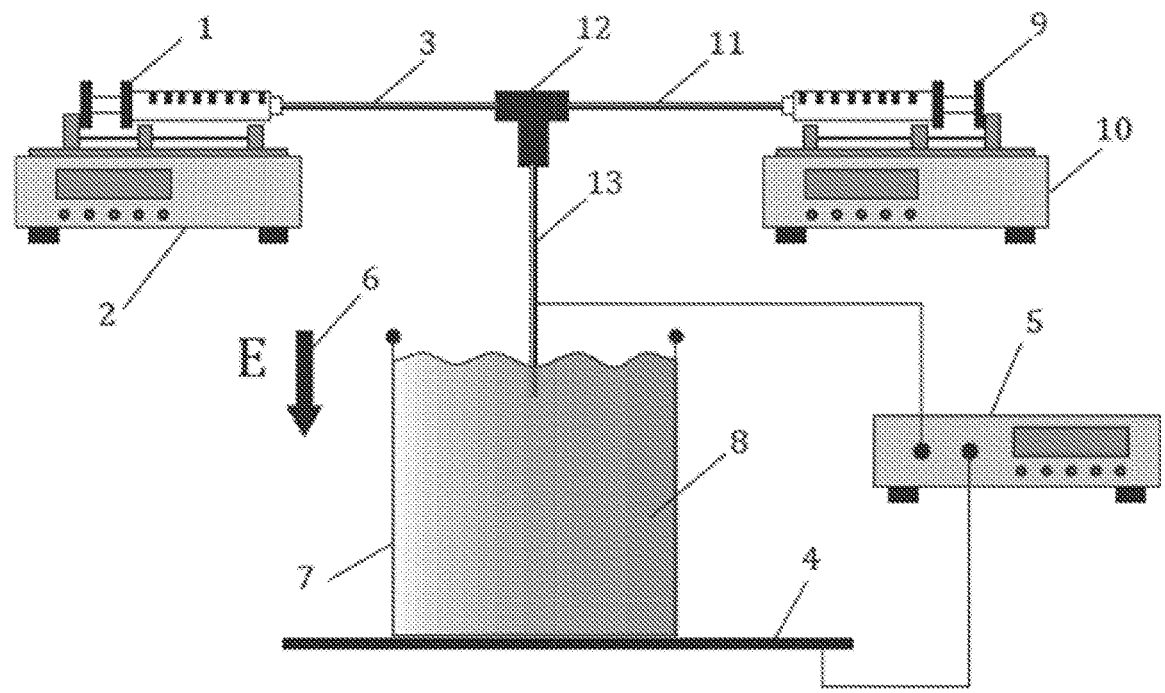

FIG. 6 shows a coaxial electrospray assembly in which a bath 7 containing a liquid 8 is disposed between an end of the tube 13 and an electrode 4. The end of the tube 13 is immersed in the liquid 8.

Figure 7:
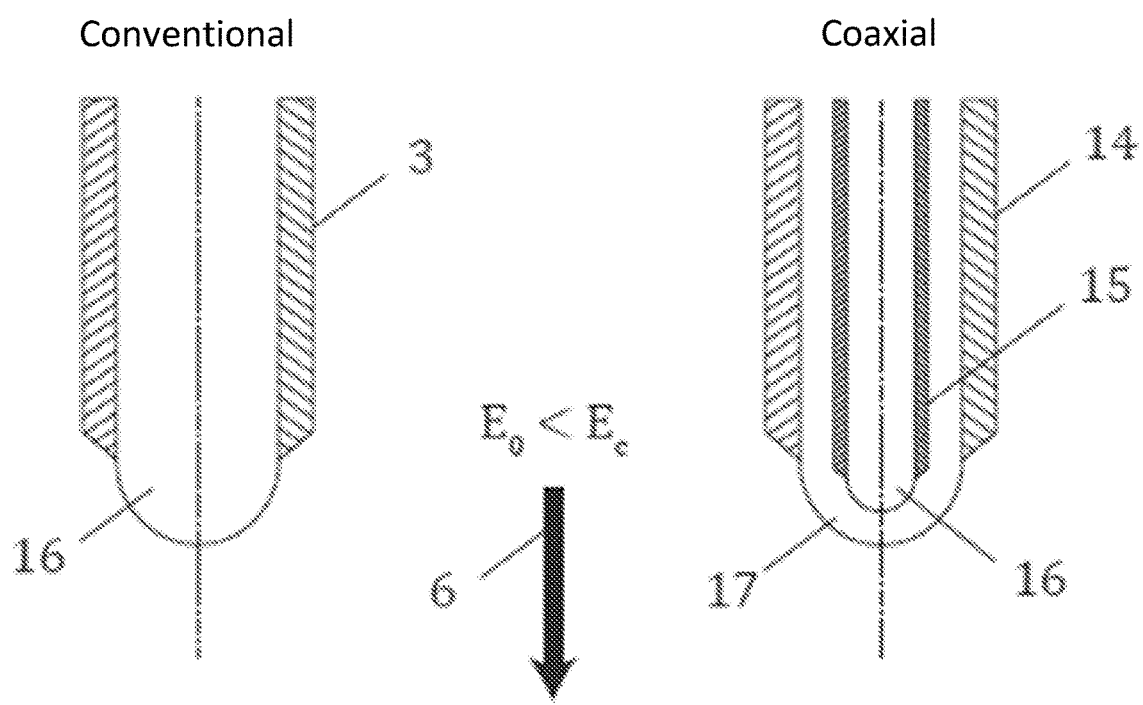

FIG. 7 shows the menisci at the end of a tube when the electric field 6 is below a threshold value for electrospray. In a conventional single-liquid tube 3, the meniscus of a liquid 16 does not form an electrospray jet. In a coaxial assembly including an outer tube 14 and inner tube 15, and an outer liquid 17 and an inner liquid 16, the meniscus at the end of the assembly does not form a coaxial electrospray jet.

Figure 8:
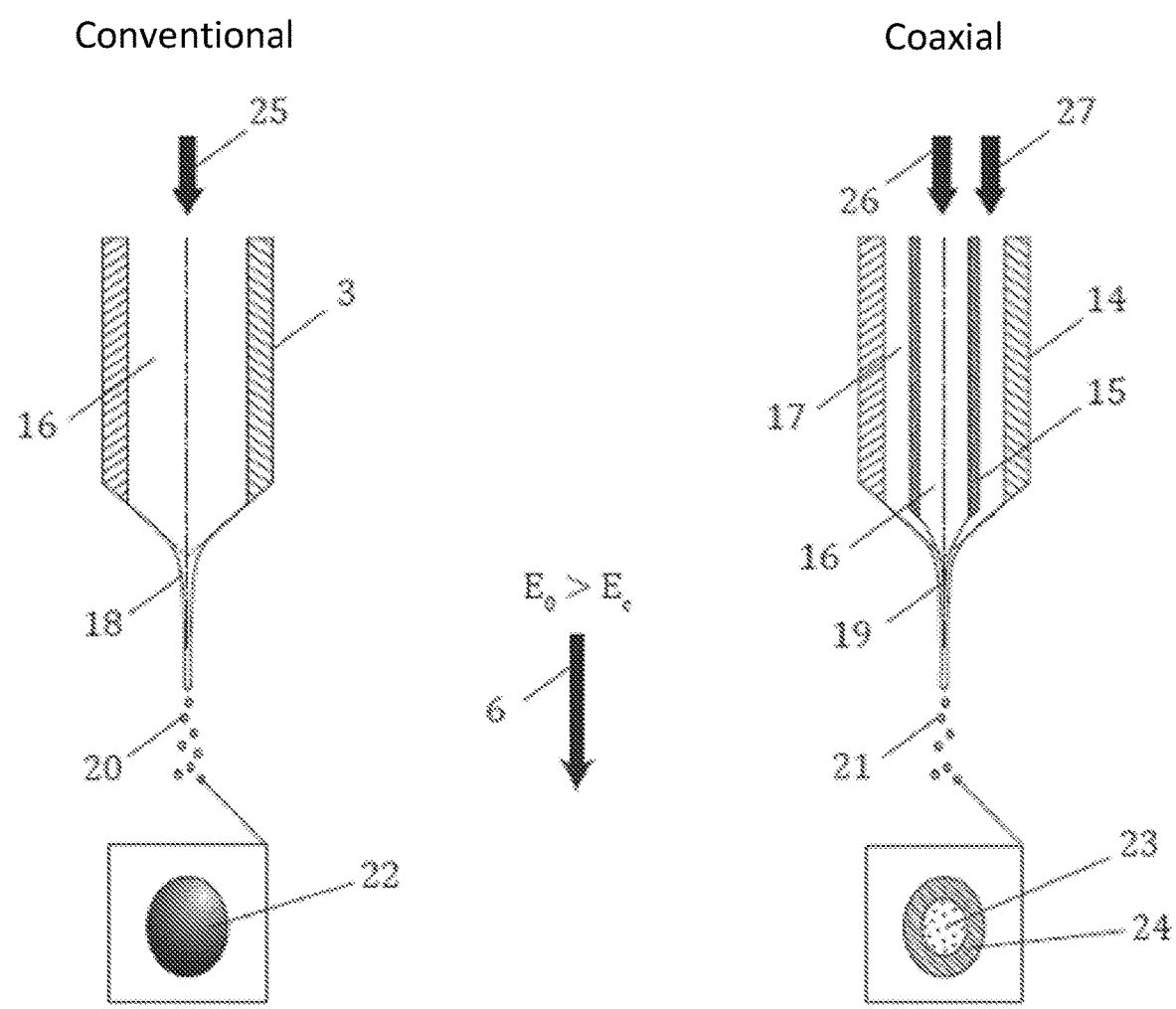

FIG. 8 shows droplet formation from the end of a tube when the electric field 6 is above a threshold value for electrospray. In a conventional single-liquid tube 3, a jet 18 breaks into a droplet ensemble 20 in which the droplets 22 include a single liquid 16. This accompanies a flow 25 of liquid 16 through the tube 3. In a coaxial electrospray assembly, a coaxial jet 19 breaks into an ensemble 21 of core-shell droplets having a core 23 of liquid 16 and a shell 24 of liquid 17. This accompanies a flow 26 of liquid 16 through the inner tube 15 and a flow 27 of liquid 17 through the outer tube 14.

Figure 9:
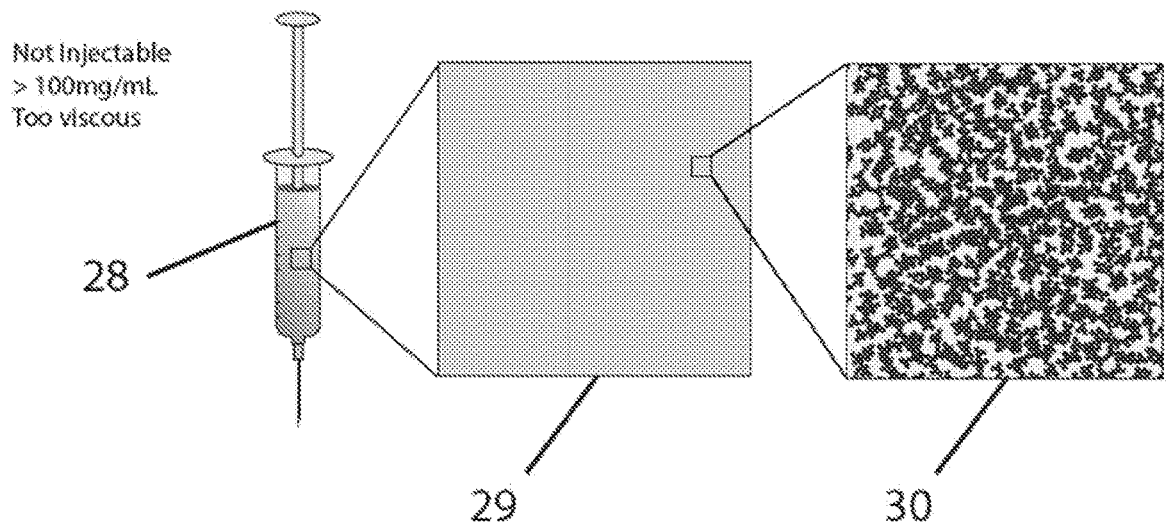
Figure 9:
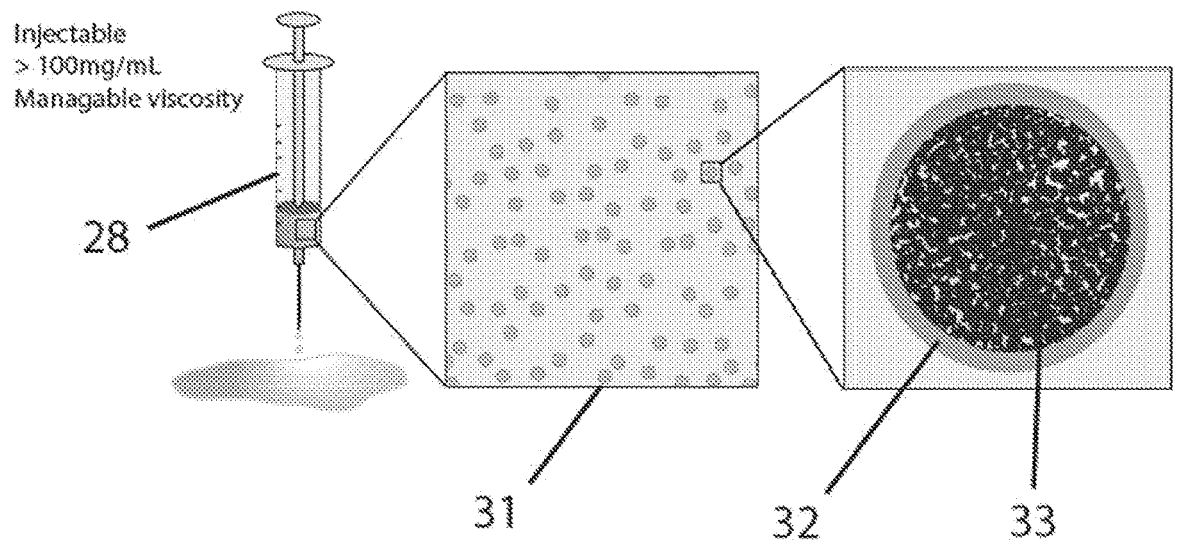

FIG. 9 shows a comparison of a solution and a suspension formulation produced by the disclosed methods. A solution of therapeutic or diagnostic agents 29 may be too viscous to administer with a standard injector 28 on account of onerous intermolecular interactions 30. In contrast, a suspension formulation 31 of particles 32 including therapeutic or diagnostic agents 33 may have a much lower effective viscosity, permitting administration with a standard injector 28.

Figure 10:
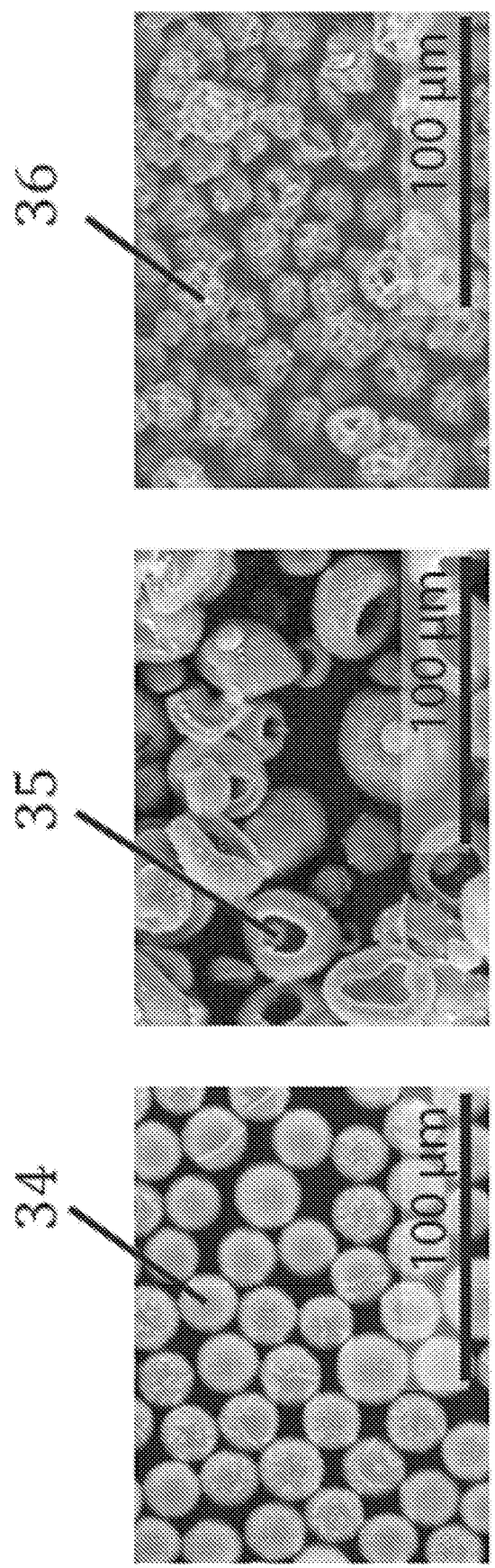

FIG. 10 is a series of images of particles of human IgG protein that were formed by electrospray particle production from an aqueous solution.

Figure 11:
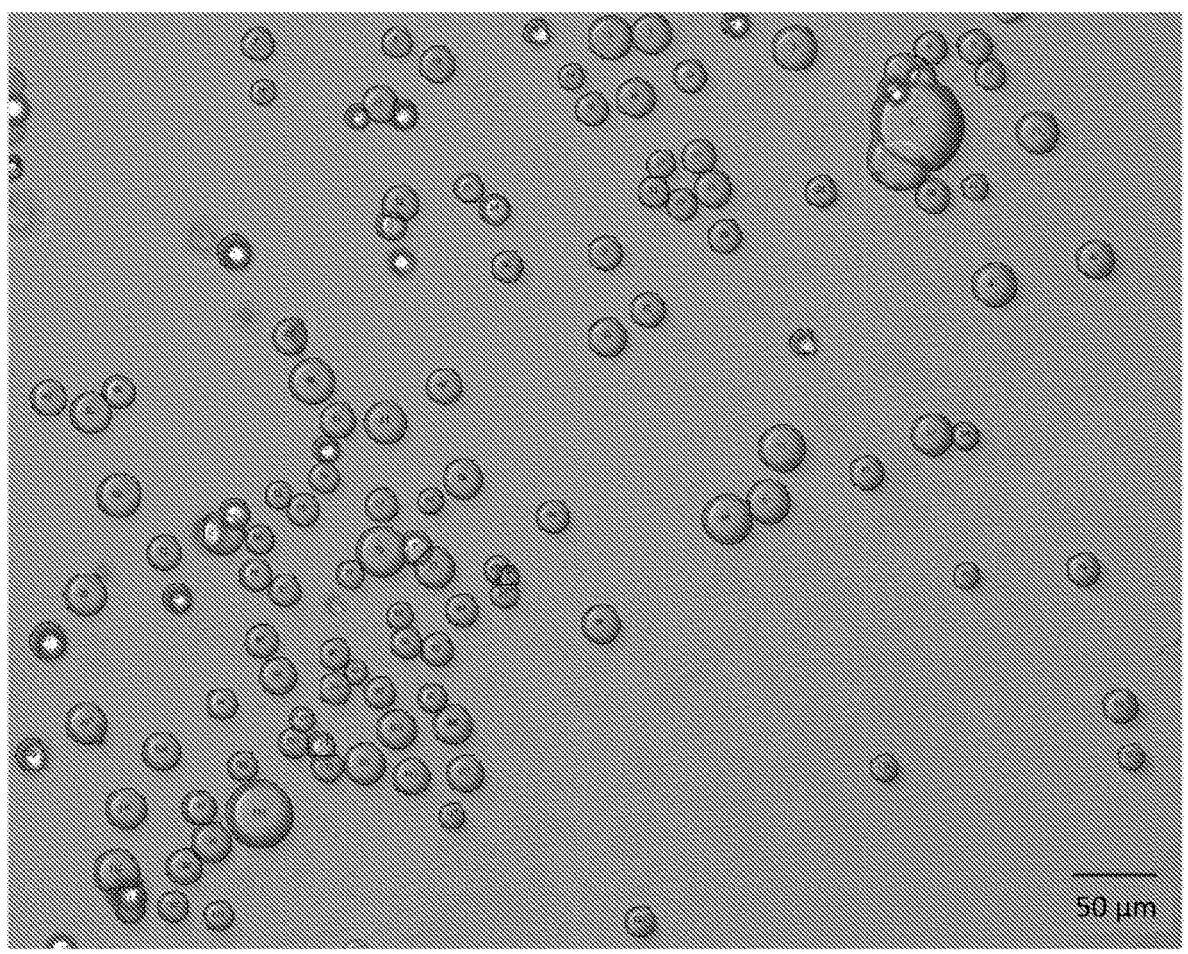

FIG. 11 is an image depicting particles of bovine serum albumin produced by electrospray particle production with an ImageJ analysis overlay. The scale bar is 50 μm.

Figure 12:
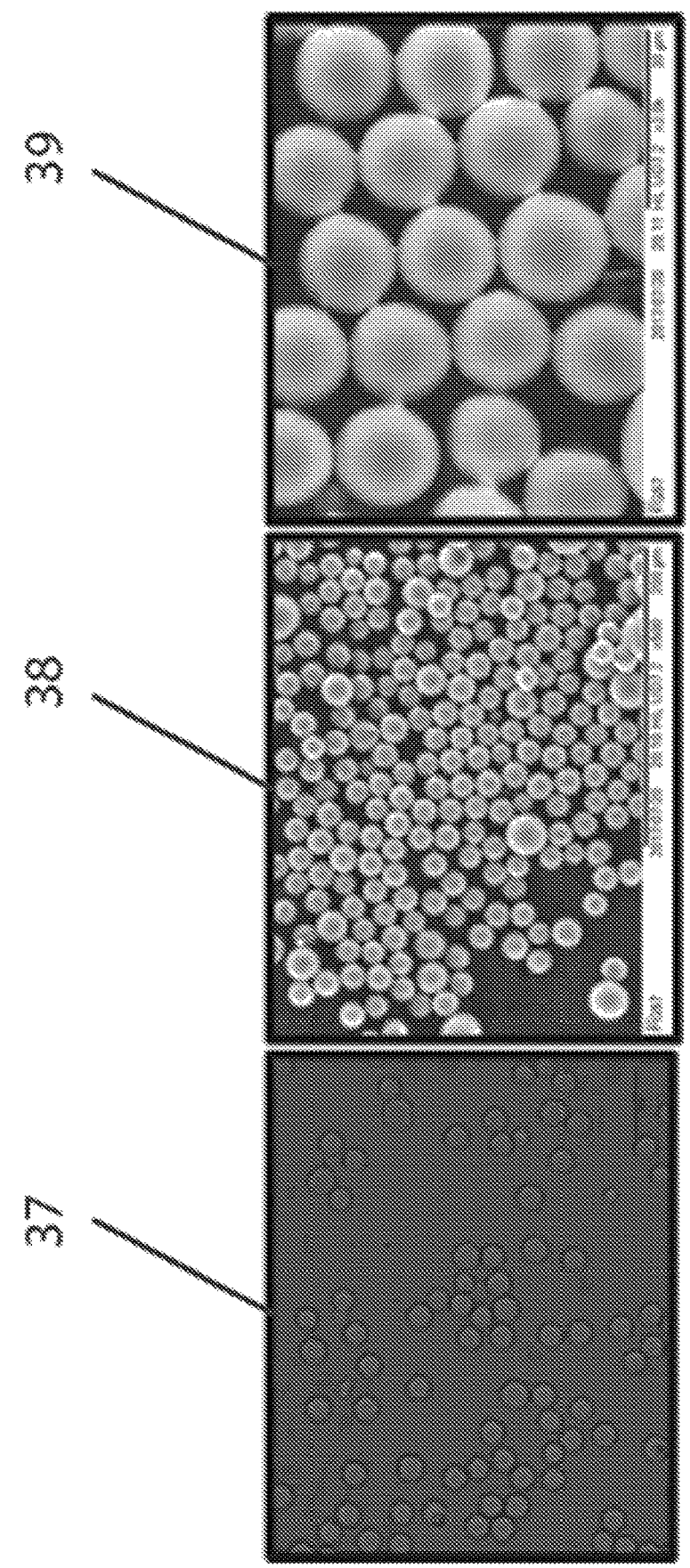

FIG. 12 is a series of images depicting particles of human IgG produced by electrospray particle production. Image 37 is an optical image at a magnification of 20×. Images 38 and 39 are SEM images at magnifications of 2000× and 5000×, respectively.

Figure 13:
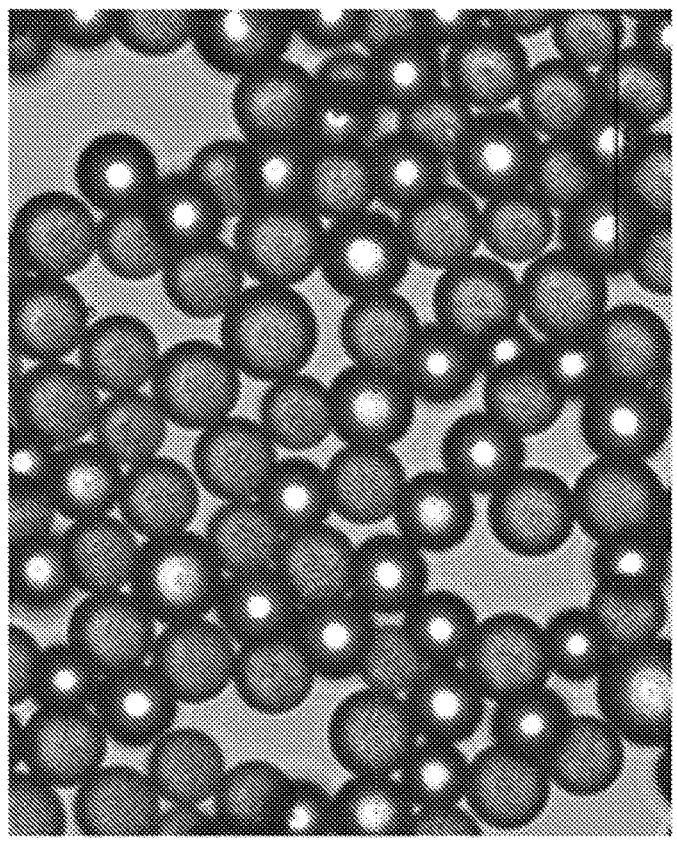
Figure 13:
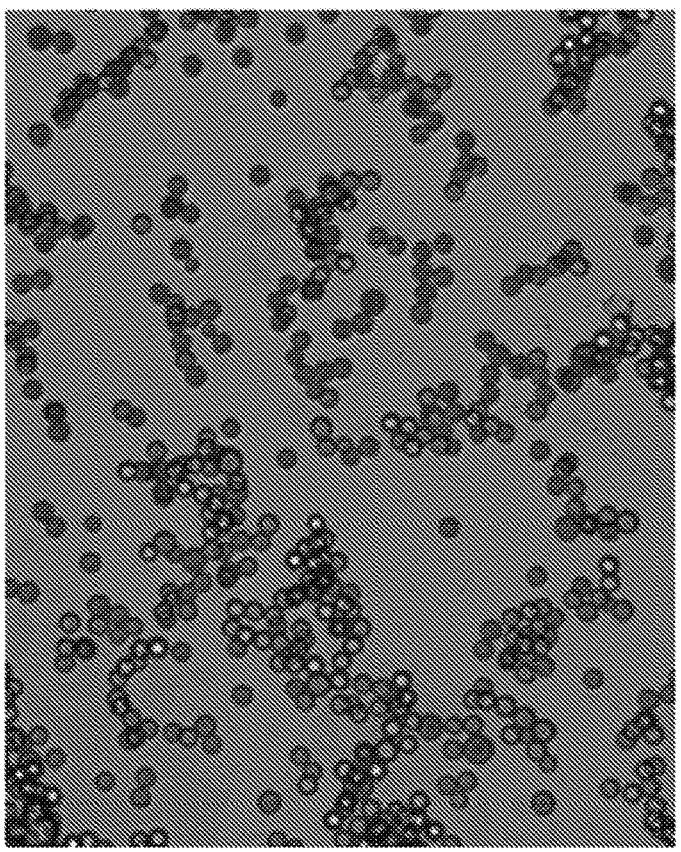

FIG. 13 is a series of optical images of particles of monoclonal antibodies produced by electrospray particle production. The scale bar is 50 μm.

Figure 14:
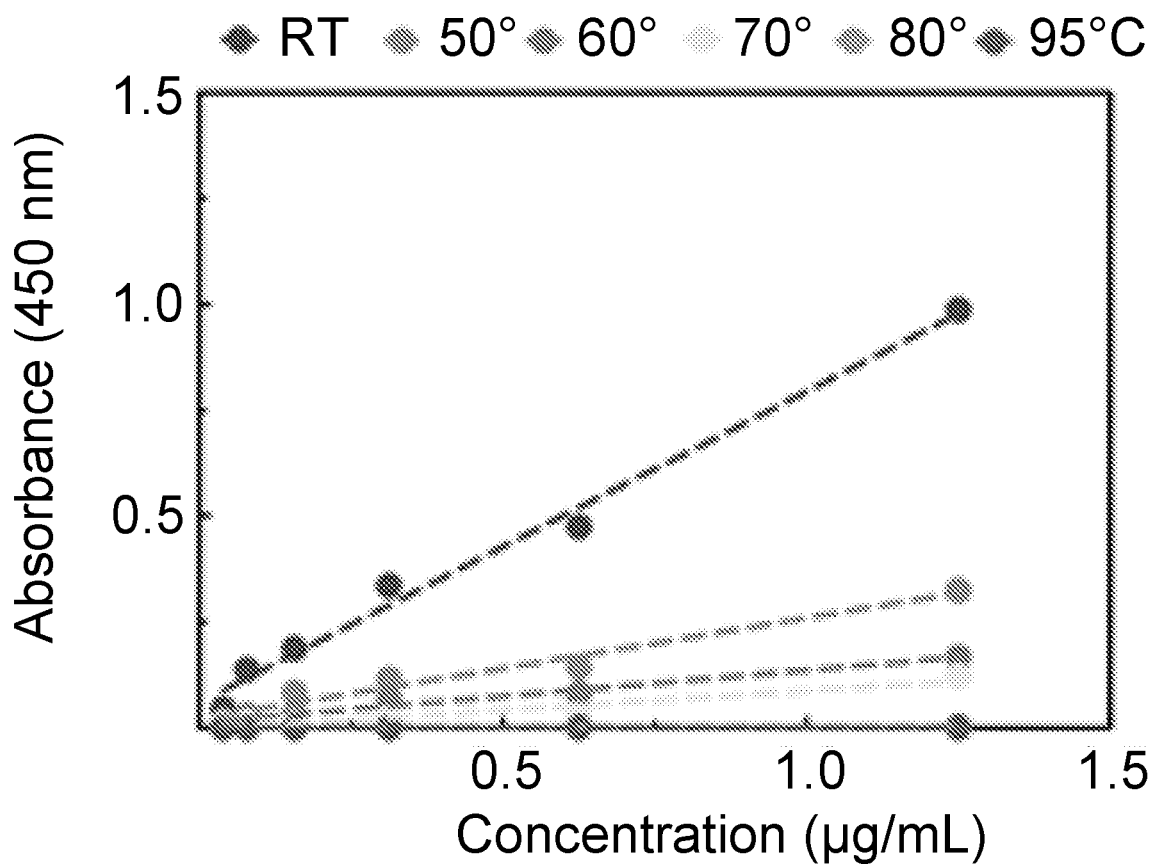

FIG. 14 is a graph showing ELISA assay control experiment results for human IgG.

Figure 15:
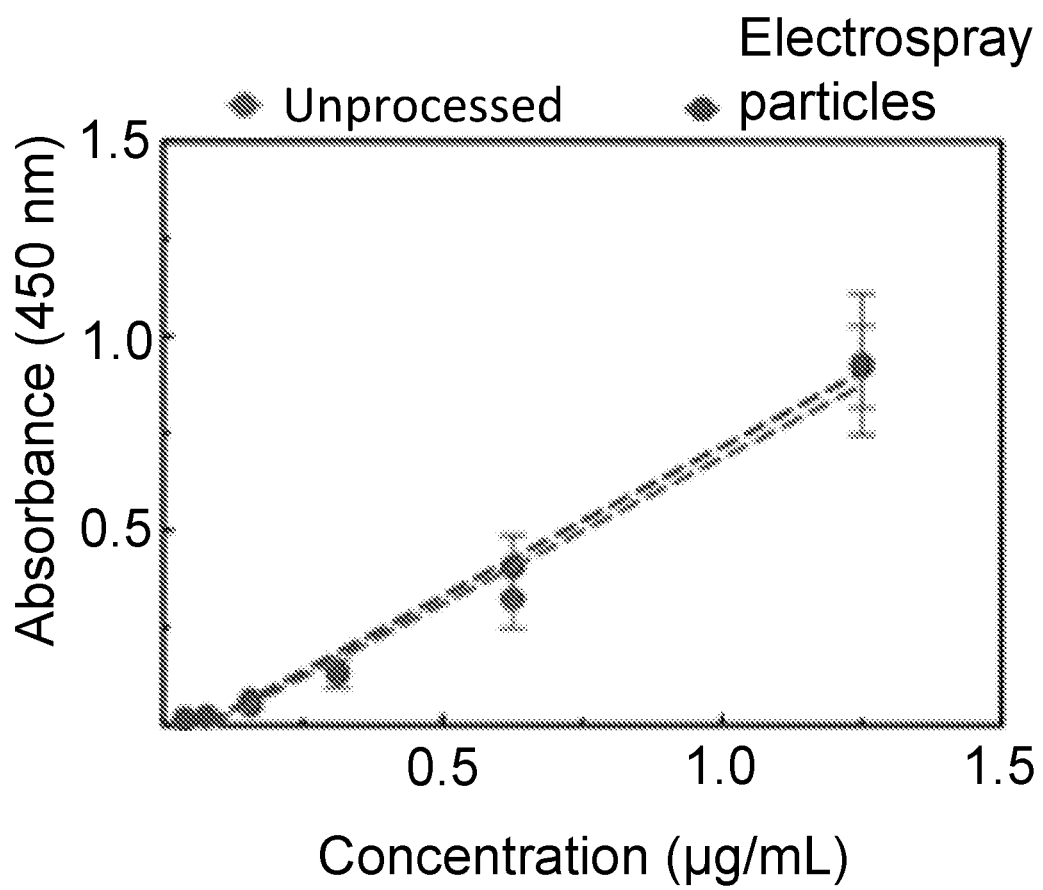

FIG. 15 is a graph showing a comparison of the ELISA signals for unprocessed (pre-electrospray particle formation) and electrosprayed human IgG.

Figure 16:
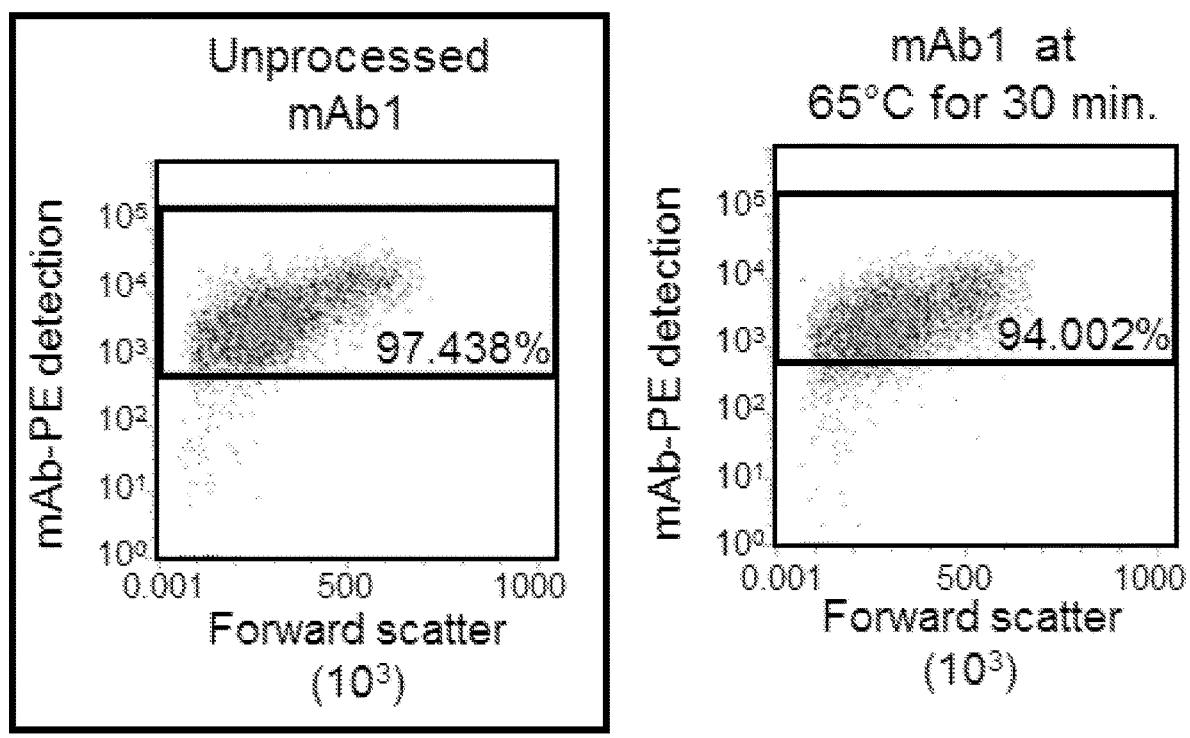
Figure 16:
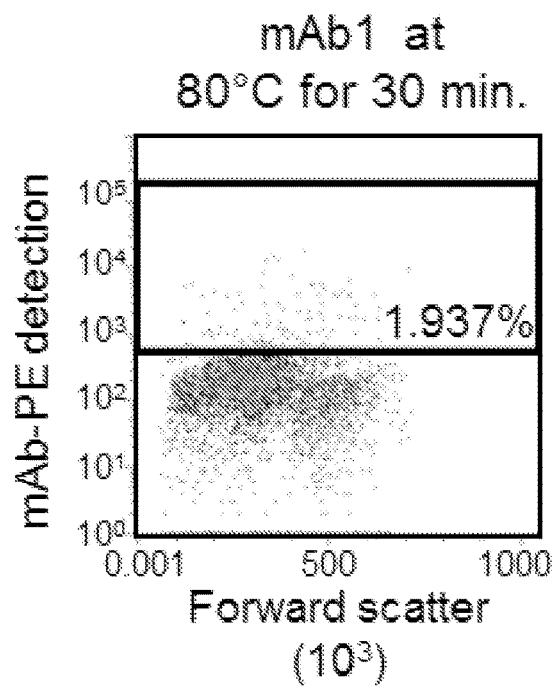
Figure 16:
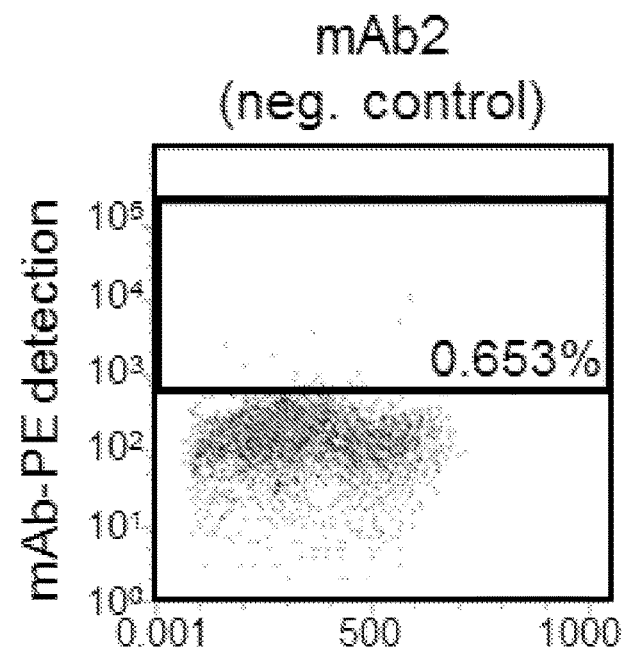
Figure 16:
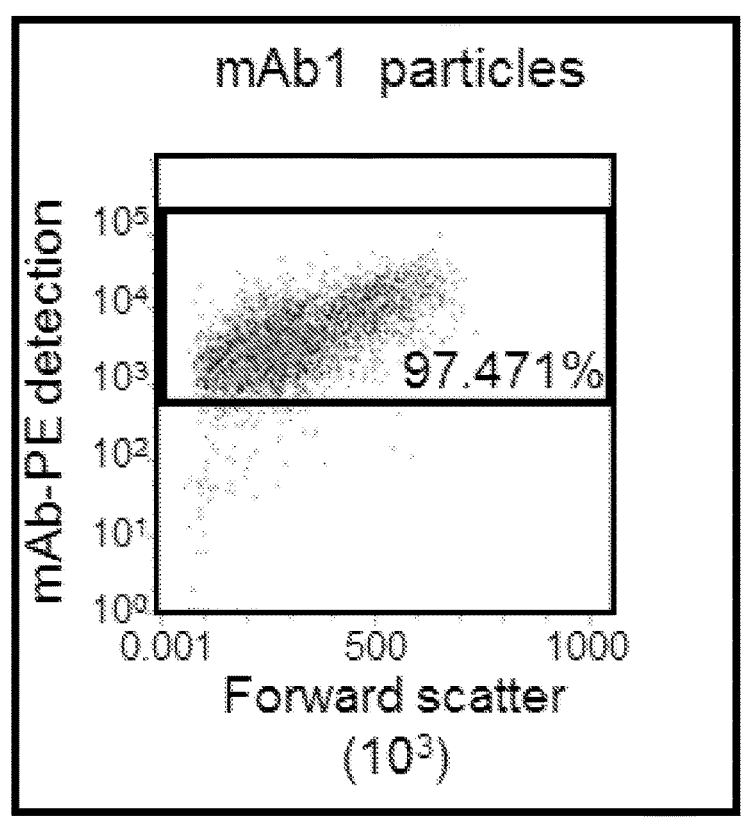

FIG. 16 is a series of graphs showing cellular binding data for an electrosprayed monoclonal antibody (mAb1).

Figure 17:
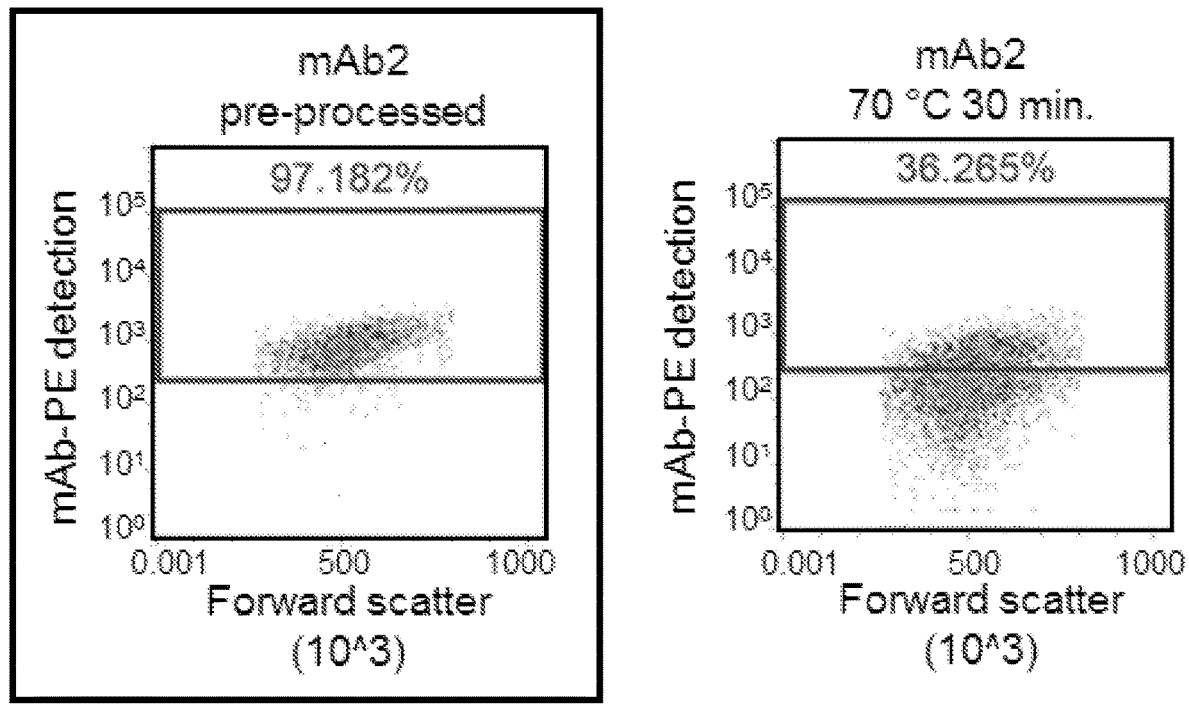
Figure 17:
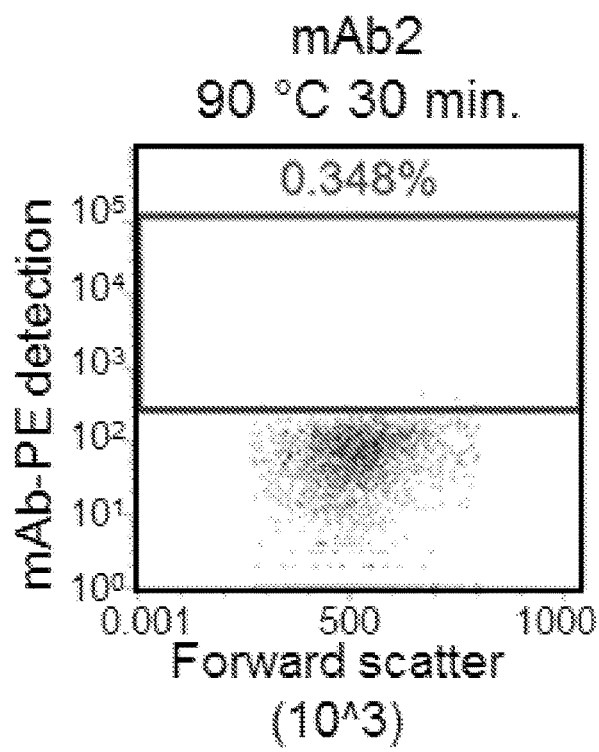
Figure 17:
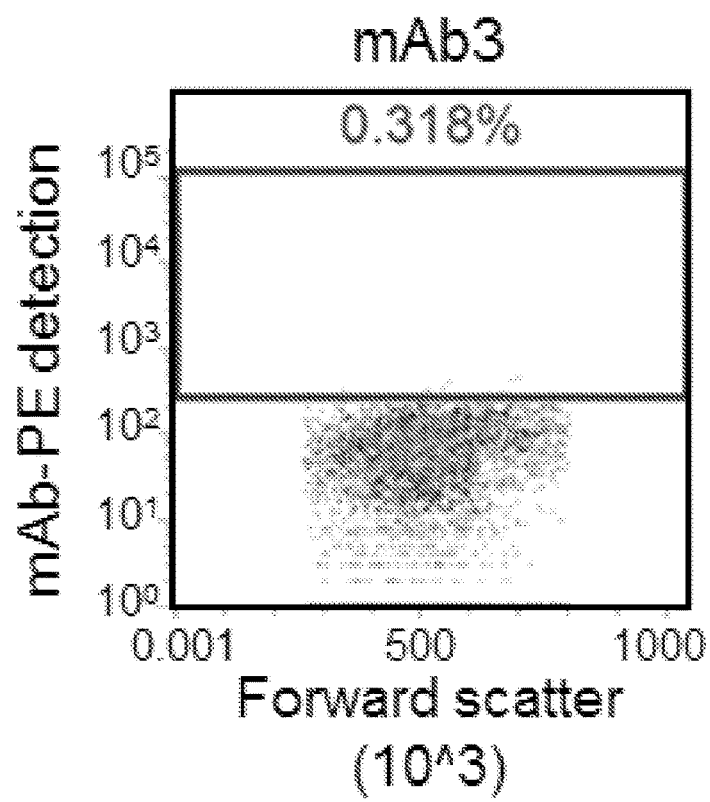
Figure 17:
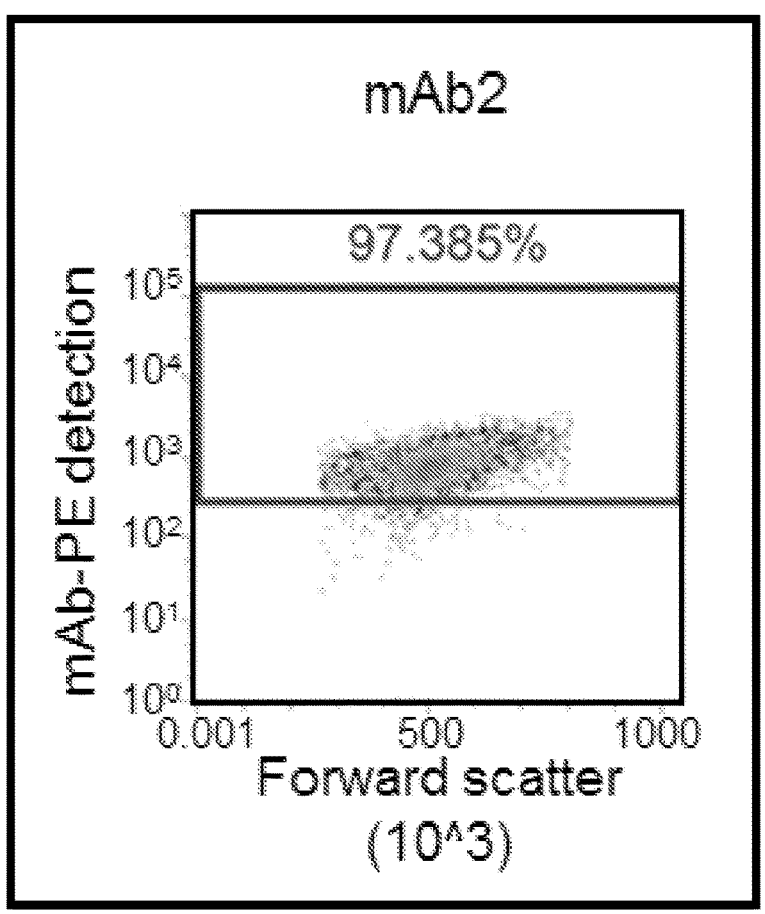

FIG. 17 is a series of graphs showing cellular binding data for an electrosprayed monoclonal antibody (mAb2).

Figure 18:
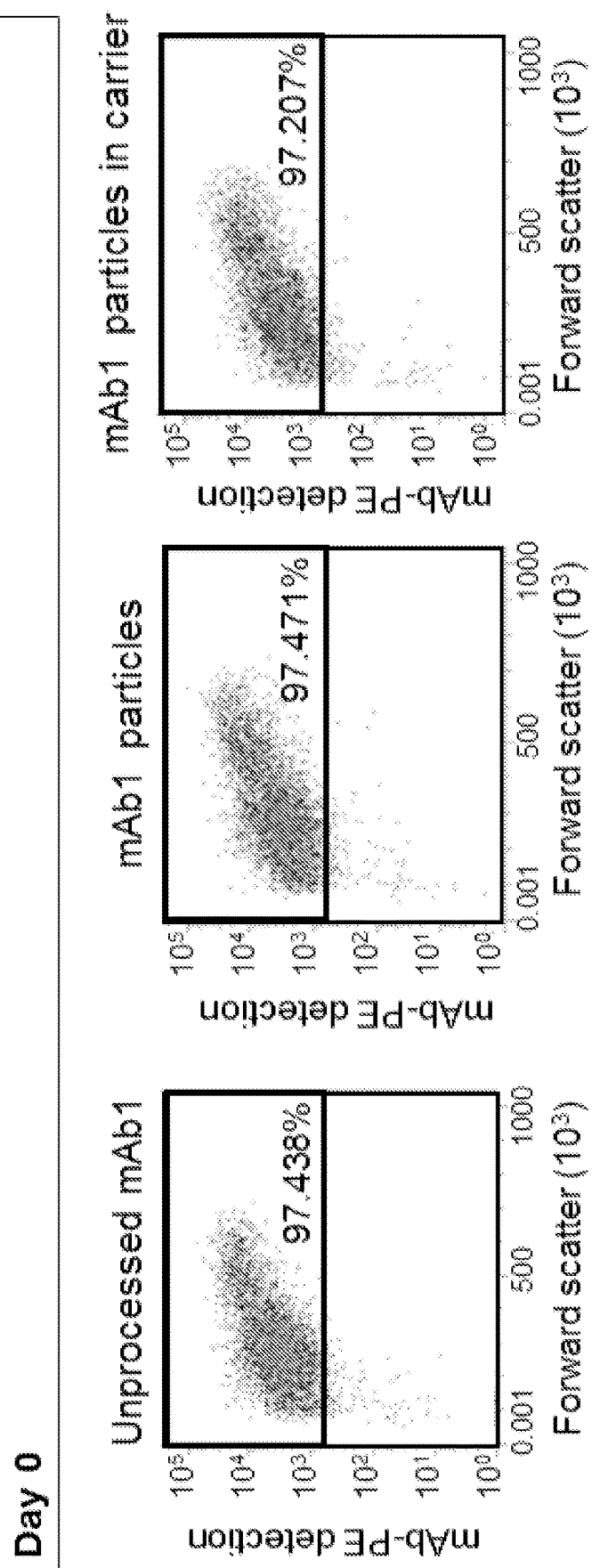
Figure 18:
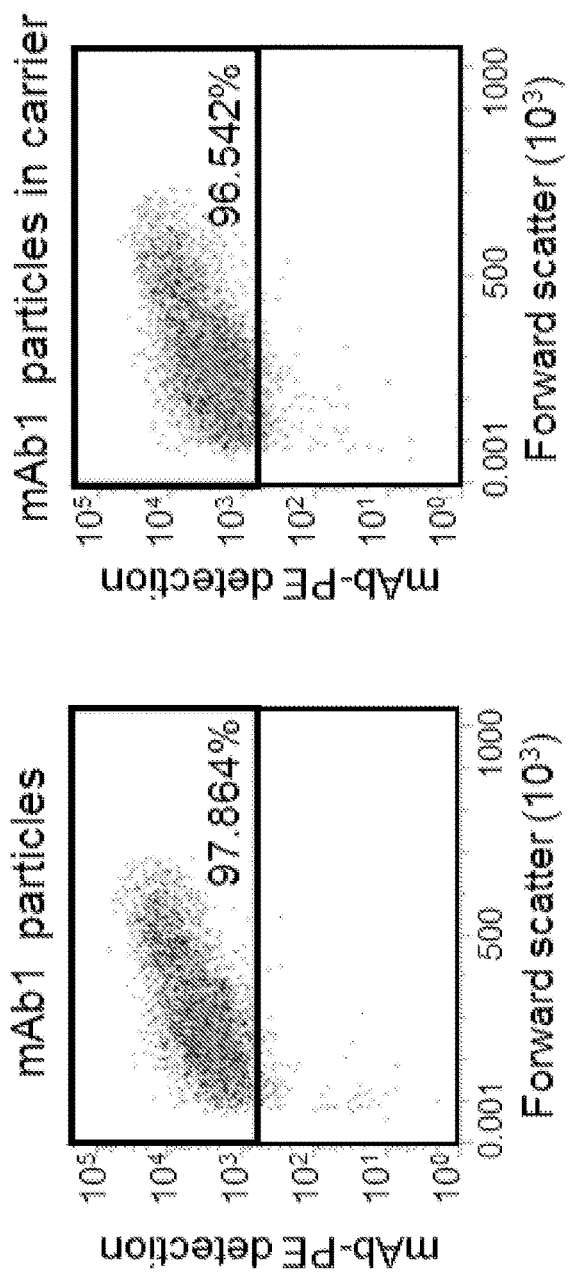

FIG. 18 is a series of graphs showing cellular binding data for an electrosprayed monoclonal antibody (mAb1) before and after accelerated storage. Particles were stored with and without a suspension medium (carrier).

Figure 19:
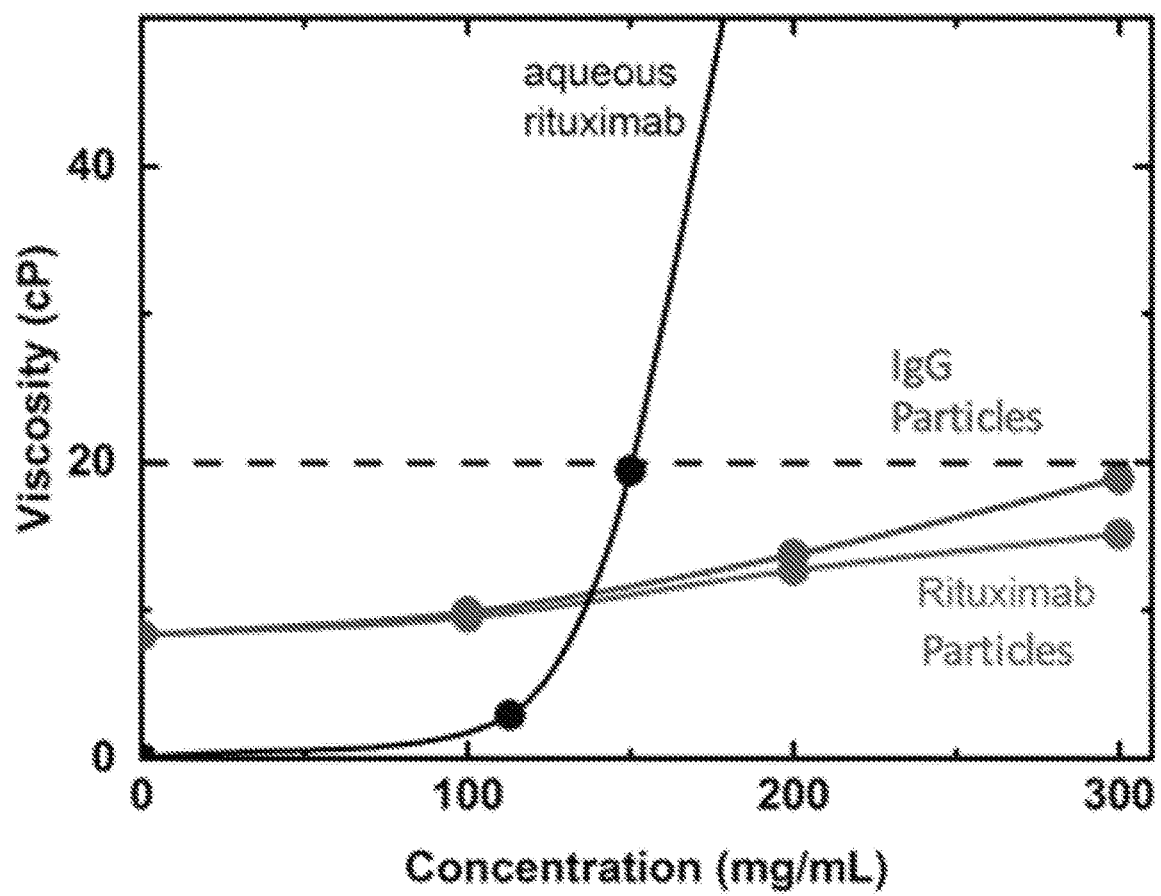

FIG. 19 is a graph showing viscosity data for various aqueous and suspension formulations at different concentrations.

Figure 20:
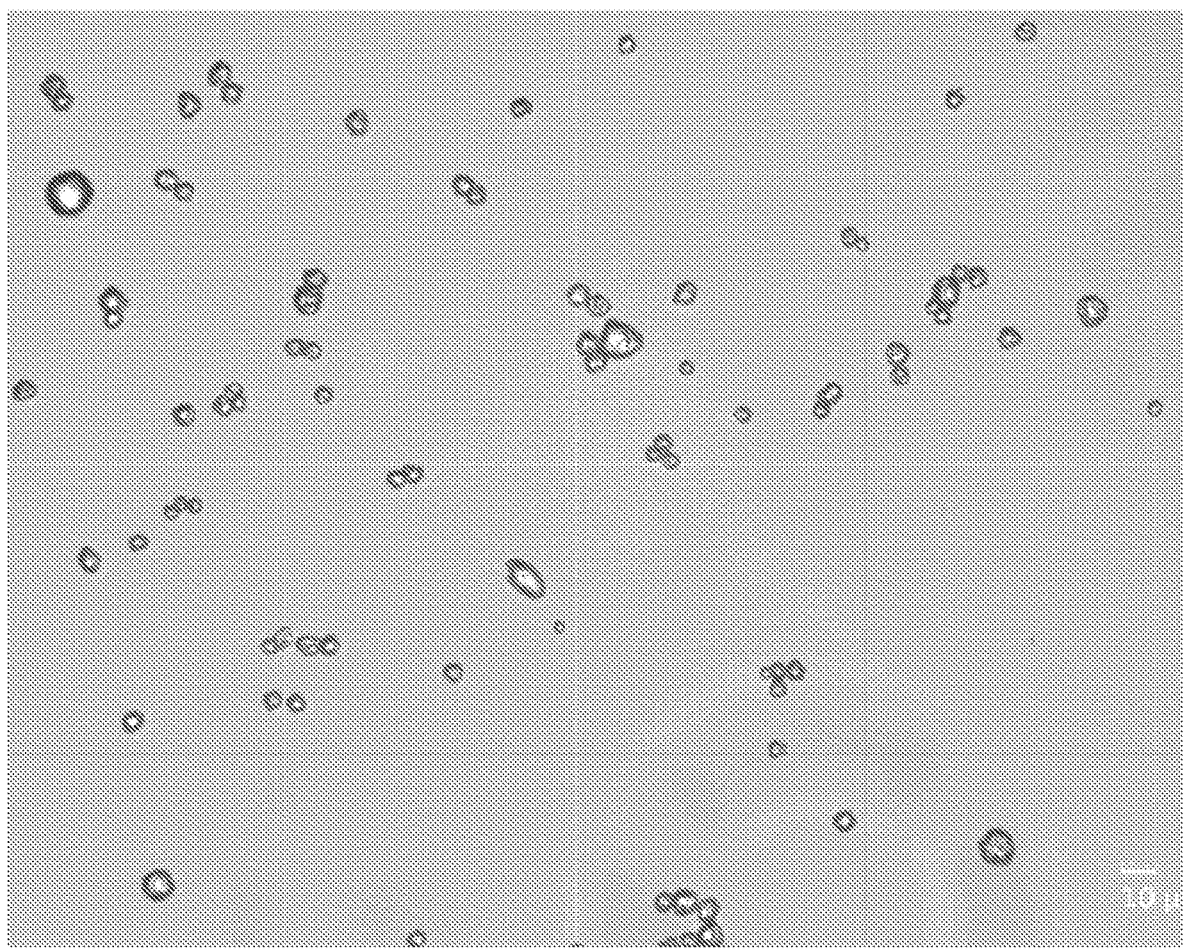

FIG. 20 is an image showing human IgG particles produced by an atomizer with the assistance of an electric field. The scale bar is 10 μm.

Figure 21:
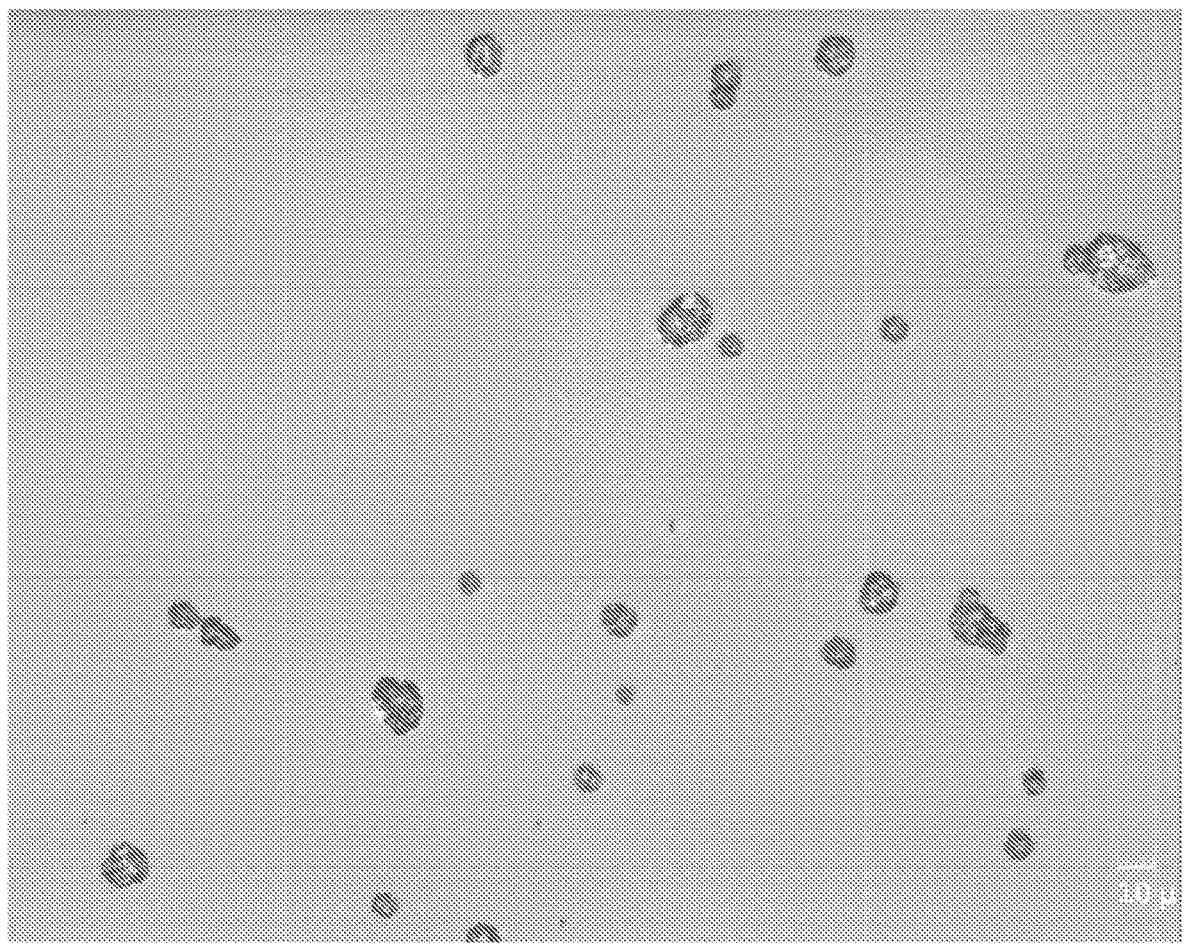

FIG. 21 is an image showing human IgG particles produced by an atomizer without the assistance of an electric field. The scale bar is 10 μm.

Figure 22:
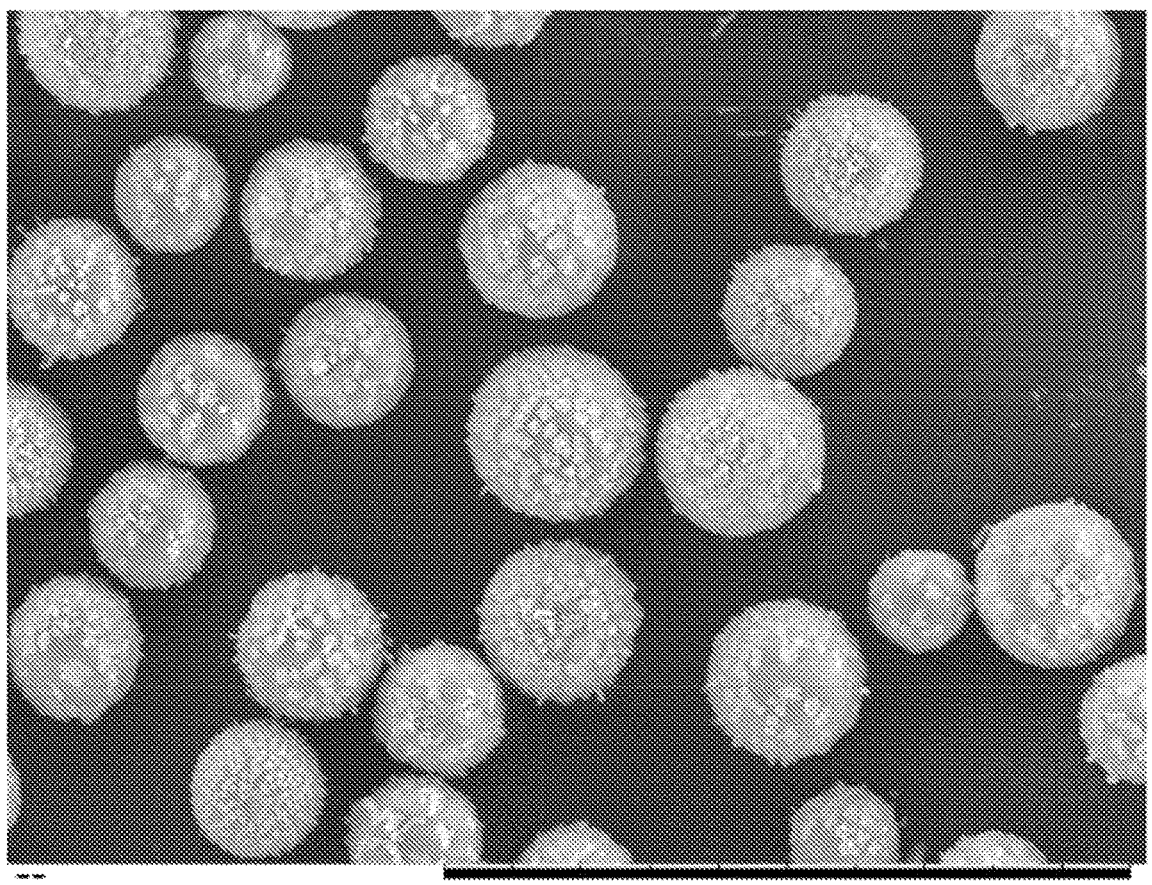

FIG. 22 is an image showing a family of human IgG particles including a salt which is salient at the surface of the particles. The scale bar is 100 μm.

Figure 23:
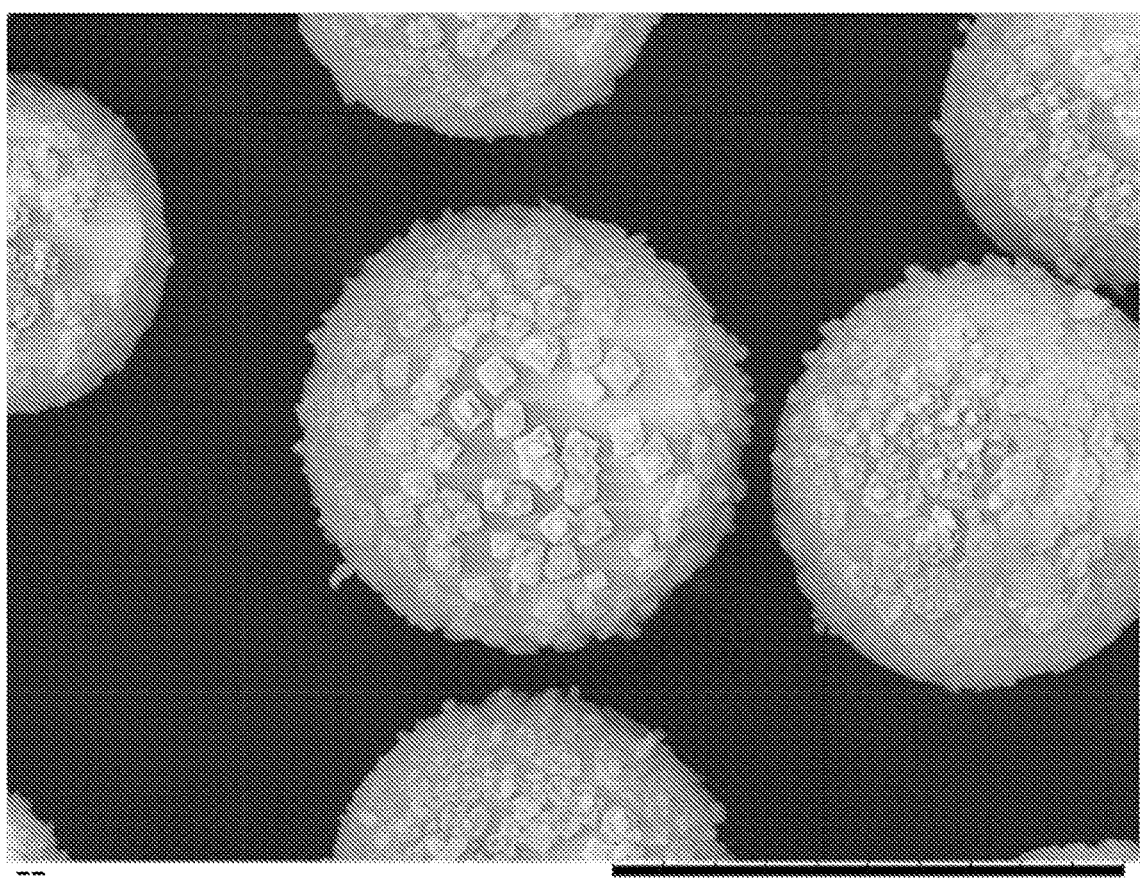

FIG. 23 is an image showing a family of human IgG particles including a salt which is salient at the surface of the particles. The scale bar is 30 μm.

Figure 24:
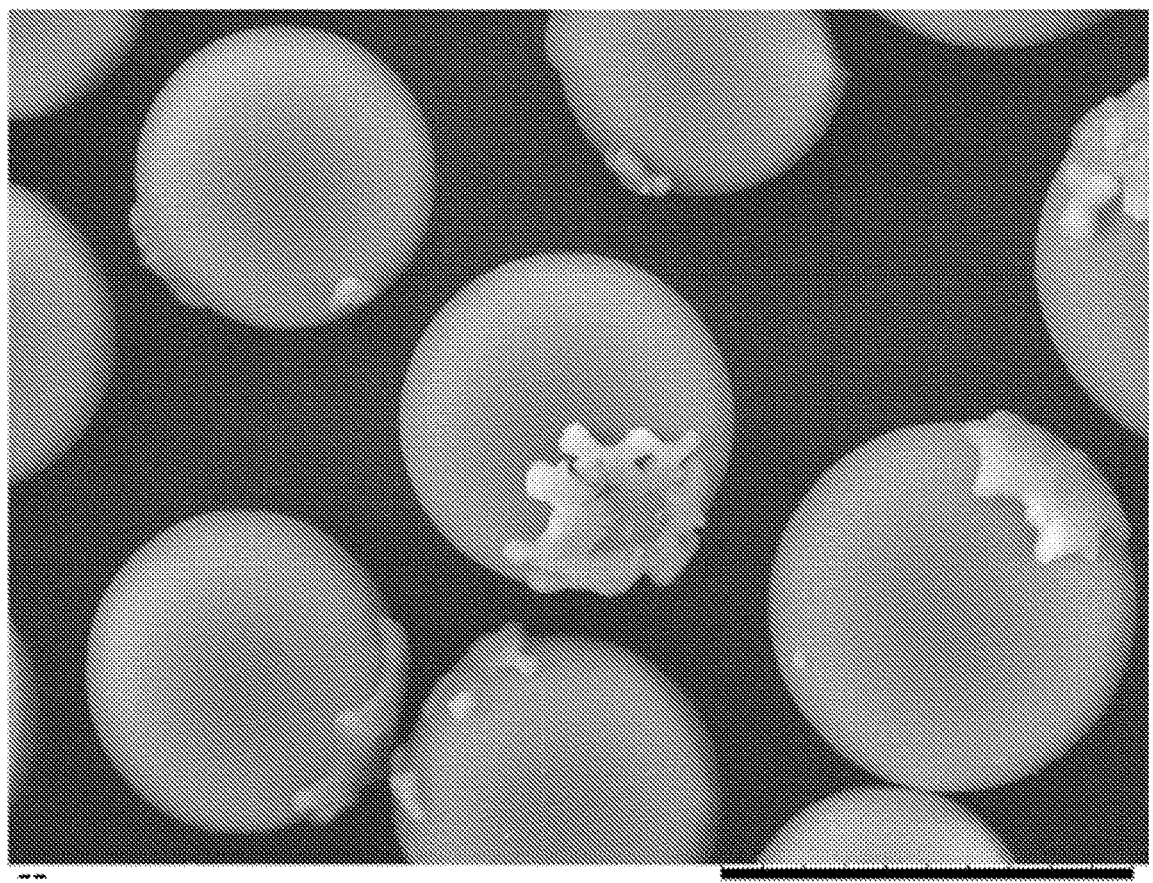

FIG. 24 is an image showing a family of human IgG particles including a sugar which is salient at the surface of the particles. The scale bar is 30 μm.

Figure 25:
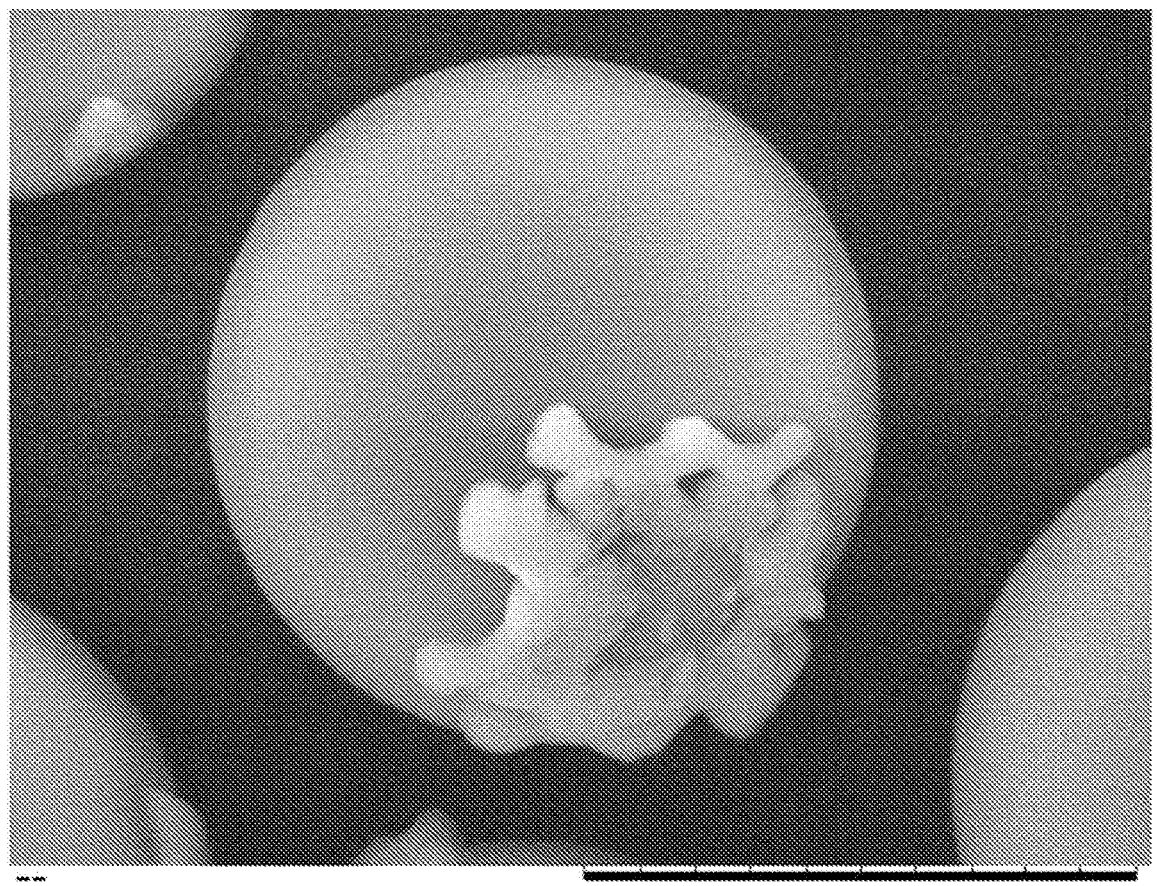

FIG. 25 is an image showing a family of human IgG particles including a sugar which is salient at the surface of the particles. The scale bar is 20 μm.

Figure 26:
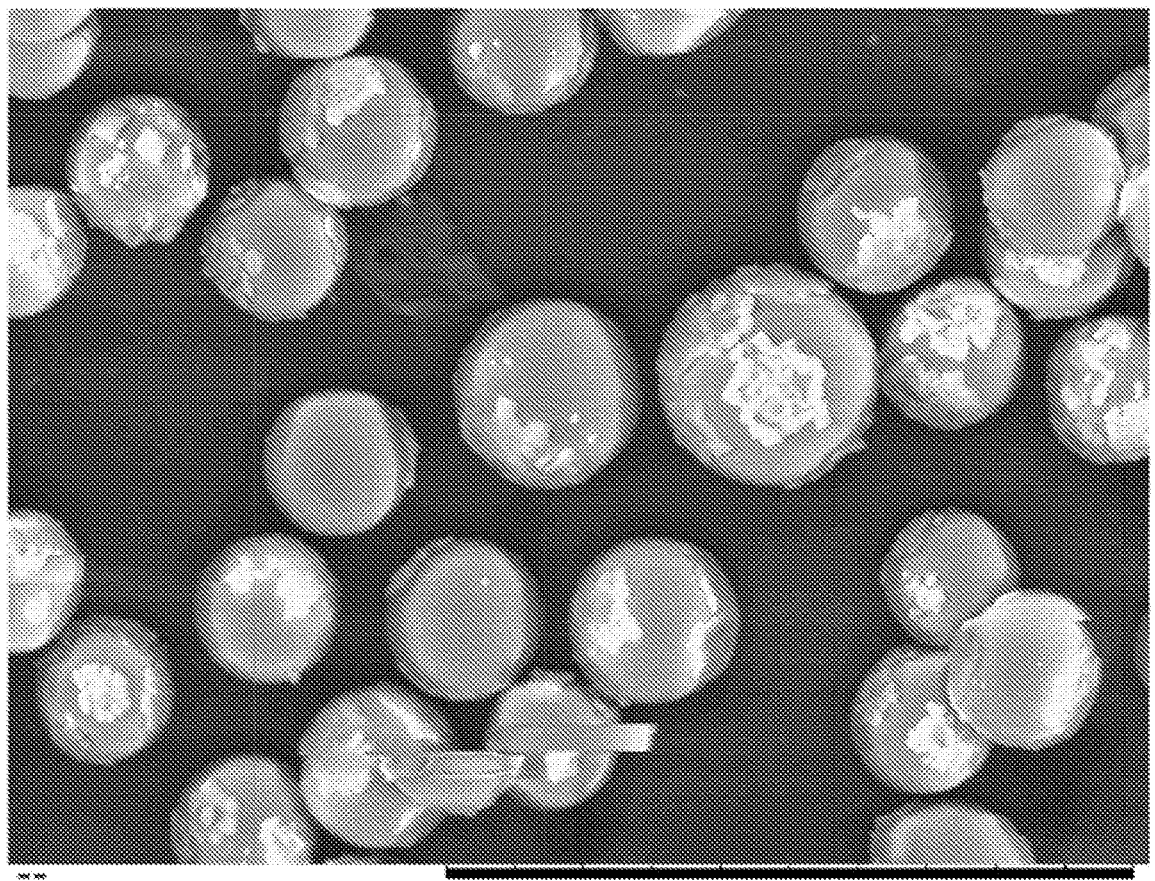

FIG. 26 is an image showing a family of monoclonal antibody (mAb3) particles including a sugar which is salient at the surface of the particles. The scale bar is 100 μm.

Figure 27:
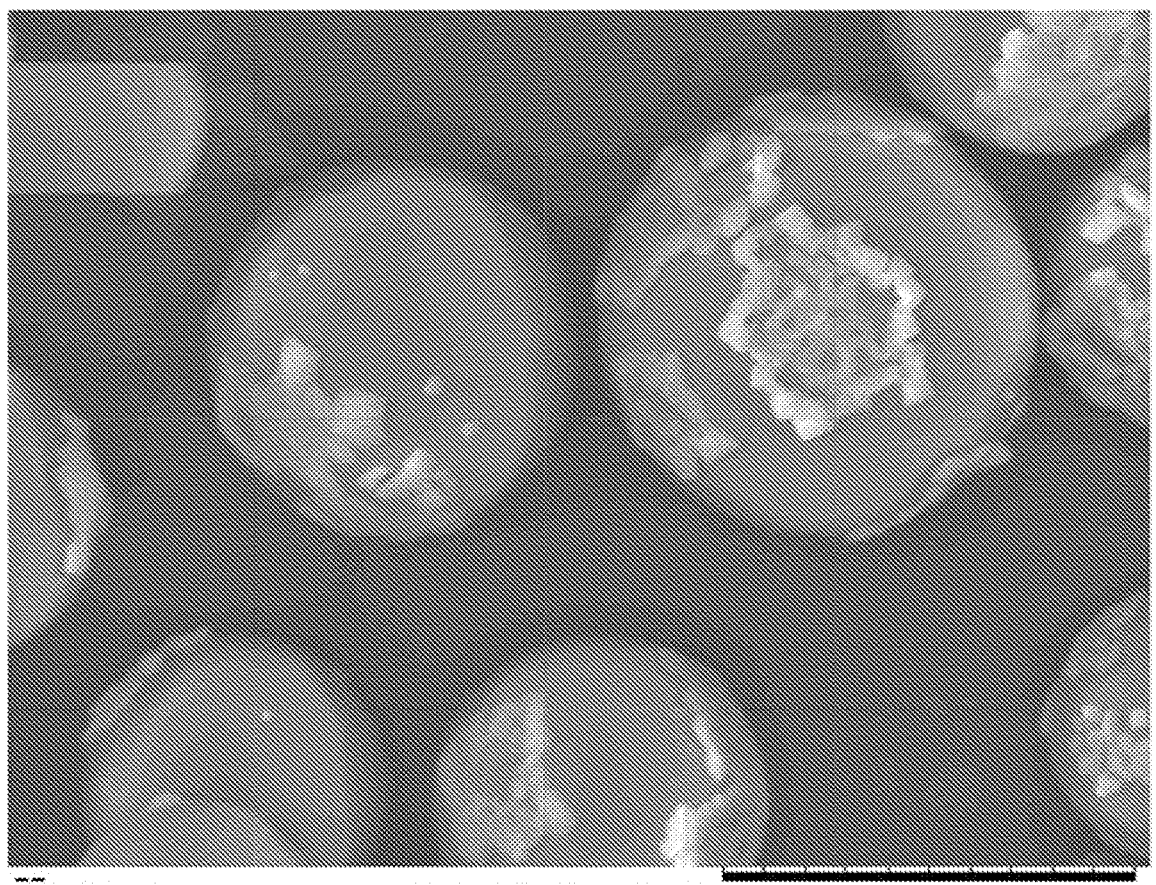

FIG. 27 is an image showing a family of monoclonal antibody (mAb3) particles including a sugar which is salient at the surface of the particles. The scale bar is 30 μm.

Figure 28:
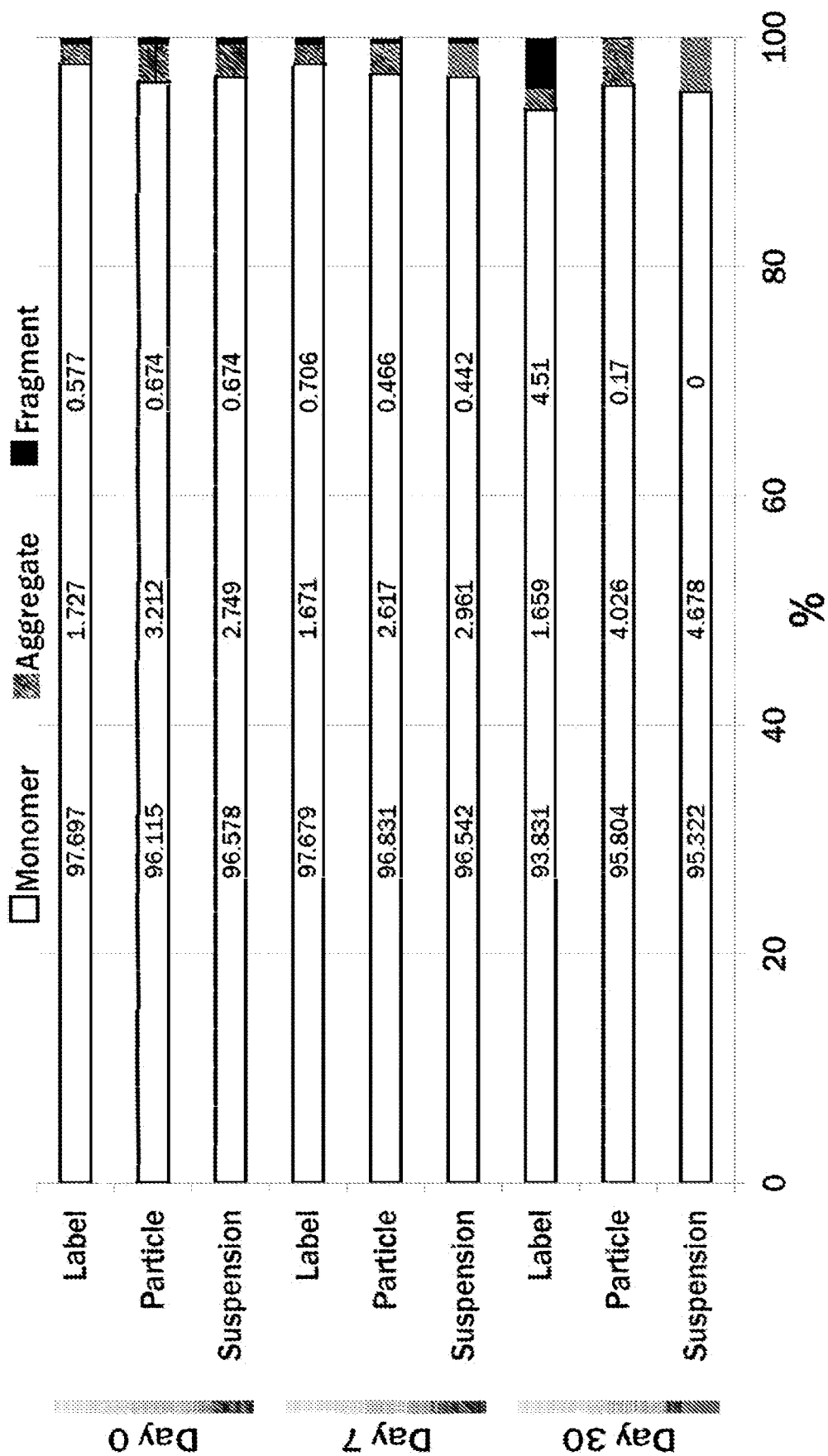

FIG. 28 is a graph showing size exclusion chromatography (SEC) data on Days 0, 7, and 30.

Figure 29A:
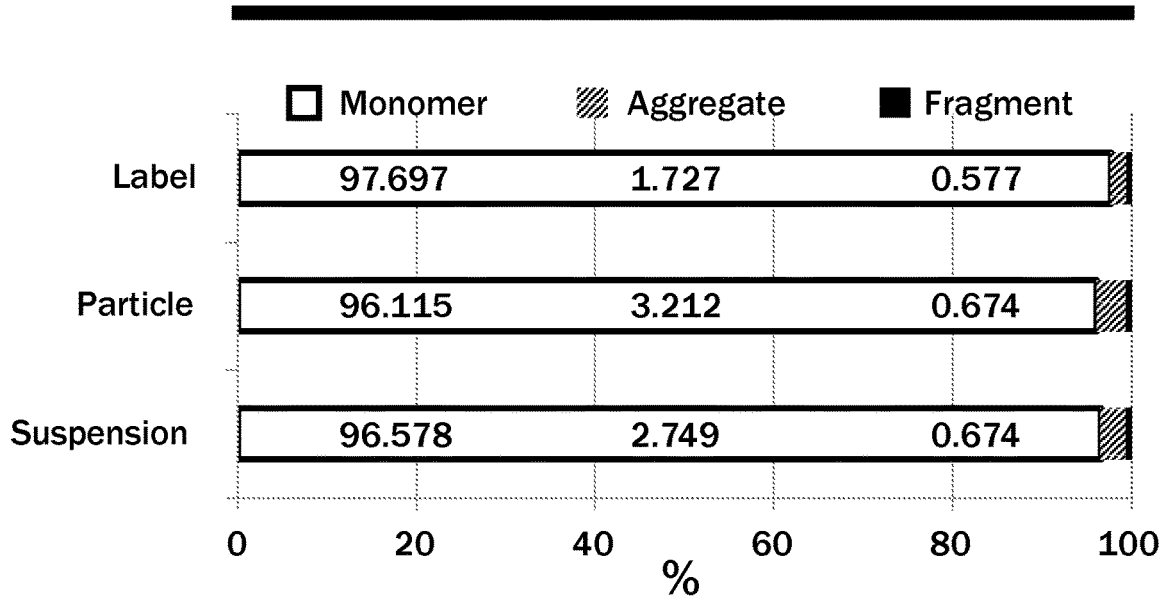
Figure 29B:
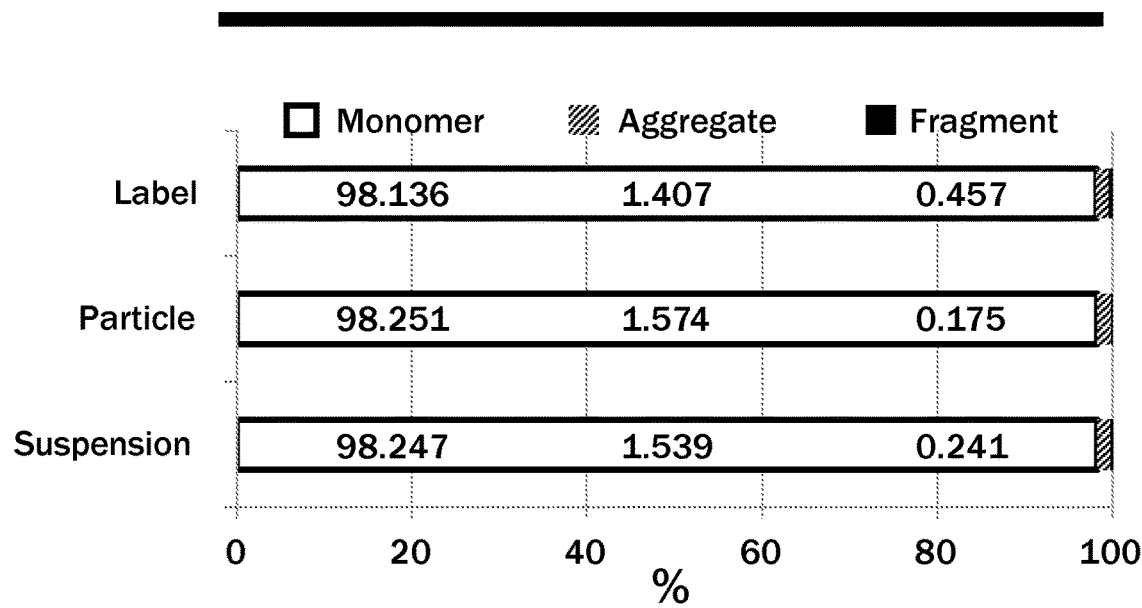

FIGS. 29A-29B is a series of graphs showing SEC data of Formulations A & B.

Figure 30A:
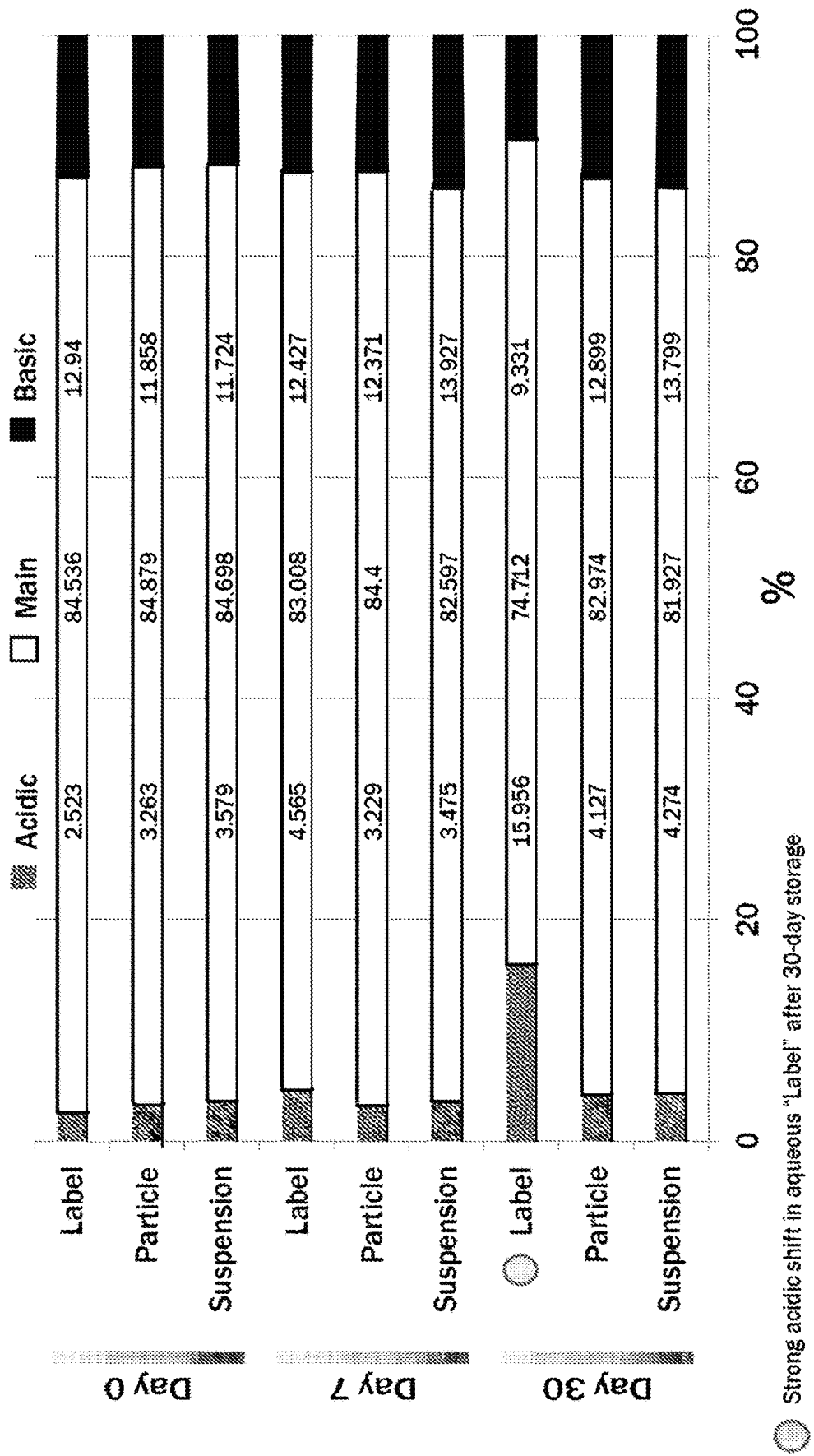

FIG. 30A is a graph showing cation ion exchange (CIEX) chromatography data on Days 0, 7, and 30.

Figure 30B:
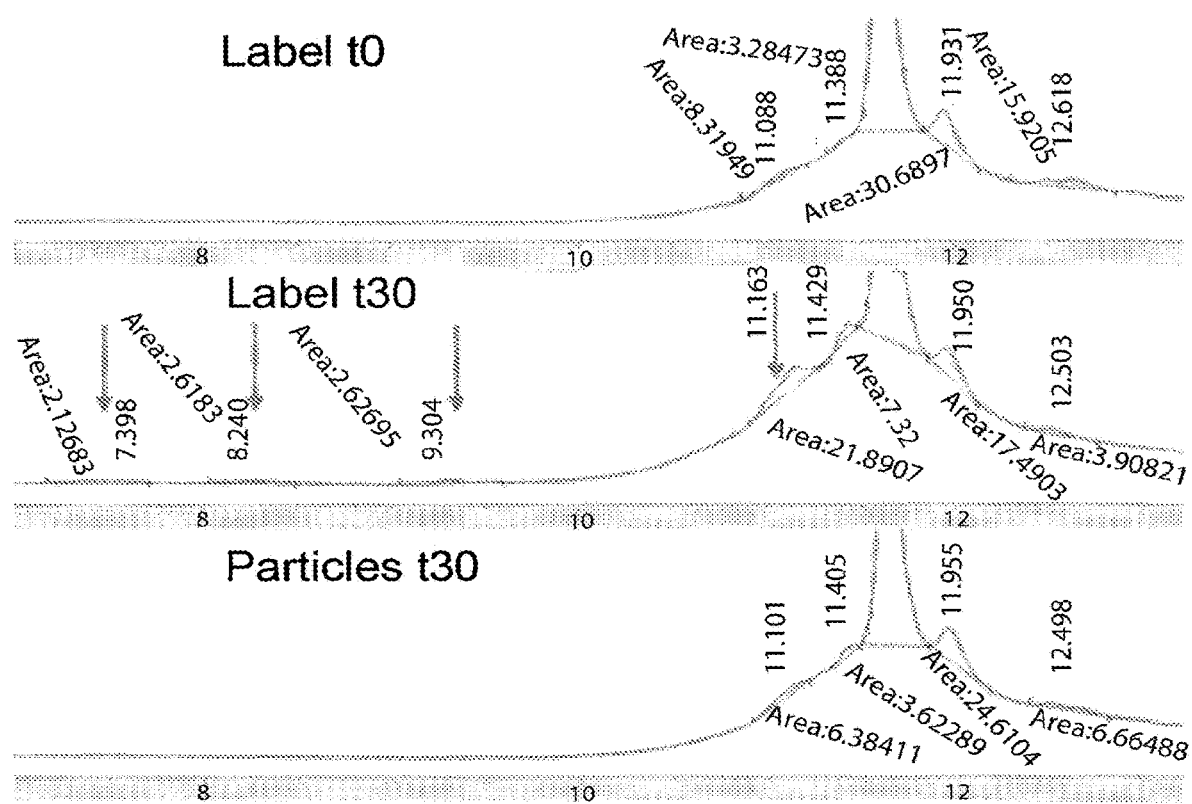

FIG. 30B is a series of plots showing the acidic shift experienced in the label formulation.

FIG. 31 is a table showing the results of a subvisible particle analysis of dissolved particles of the invention.

DETAILED DESCRIPTION

The present disclosure provides methods for the preparation of electrosprayed particles including one or more therapeutic or diagnostic agents. Particles have in the past been prepared by milling, conventional spray drying (G. Lee, Spray-Drying of Proteins. In: J. F. Carpenter and M. C. Manning (eds) Rational Design of Stable Protein Formulations, vol 13. Springer, Boston, MA), freeze drying, and conventional emulsion techniques (D. Saglam, P. Venema, R. de Vries, L. M. C. Sagis, E. van der Linde, Food Hydrocolloids, 2011, 25, 1139-1148). However, each of these techniques suffers drawbacks in preparation of particles from certain therapeutic or diagnostic agents. Milling of proteins, e.g., requires a first lyophilization step and subsequent grinding which can affect bioactivity. Control over particle morphology is also limited. Spray drying and emulsion techniques may affect protein biofunction due to high shear rates while the latter also presupposes high operating temperatures that can be harmful. A more gentle process, e.g., one that maintains bioactivity, and one whereby particle morphology can be accurately controlled, e.g., resulting in highly monodisperse particles, is that of electrospray.

In some embodiments, the particles do not have a shell. In some embodiments, the particles have a liquid, solid, or gel core and a shell. The liquid, solid, or gel includes the one or more therapeutic or diagnostic agents. In some embodiments, the therapeutic or diagnostic agents can be in the shell. The therapeutic or diagnostic agent may be dissolved or suspended in the liquid or gel, or otherwise carried by the liquid or gel, e.g., in a slurry. The electrosprayed particles can be incorporated into a medium to form a pharmaceutical composition. In some embodiments, the pharmaceutical compositions are high concentration colloidal suspensions or slurries having low viscosity, e.g., <50 cP or higher (Dias, C. et al. AAPS PharmSciTech. 2015, 16, 1107), while maintaining the stability and controlled drug release rates of the therapeutic or diagnostic agents. In some embodiments, the present invention allows for higher doses of therapeutic or diagnostic agents to be delivered while minimizing the delivery volume, shortening administration time, and/or reducing pain. In other embodiments, it provides for a powder composition of therapeutic or diagnostic agents that can be stored for periods of time in a stable fashion.

The particles can be formed by electrospraying a first liquid including a therapeutic or diagnostic agent to form droplets and removing (e.g., evaporating) the first liquid to produce particles from the droplets. The particles are solid in at least one aspect, e.g., they may have a solid shell and a liquid core. The particles can be suspended in a non-aqueous or aqueous liquid, thereby forming a non-aqueous or aqueous suspension. Alternatively, the particles can be employed in a dry form, e.g., as a powder. Electrospray permits high throughput gentle preparation and compatibility with highly viscous feed solutions. Importantly, the process of generating non-aqueous or aqueous suspensions with therapeutic or diagnostic agents does not significantly alter the structure or bioactivity of the agents. In addition, in some embodiments, the present invention allows for the delivery of higher doses of therapeutic or diagnostic agents while minimizing the delivery volume, shortening administration time, and/or reducing pain.

Suspension Concept

A pharmaceutical suspension formulation is formed in some embodiments to improve the injectability of certain therapeutic or diagnostic agents. Specifically, the suspension may exhibit lower viscosity than an aqueous solution of comparable therapeutic or diagnostic agent loading, thereby reducing the forces required to administer the suspension with a standard injector device, i.e., the breakaway and glide forces. Conceptually, particles in suspension provide a means for replacing the intermolecular interactions that prevail in regular solution, e.g., aqueous solution, with less onerous effects, e.g., excluded volume effects. In some embodiments, this permits the performance of the suspension to approximately obey the Einstein Equation for the viscosity of solutions (E. W. J. Mardles, Nature, 1940, 145, 970):

$$\eta = \eta_0(1 + 2.5\phi)$$

where $\eta$ is the apparent viscosity of the suspension, $\eta_0$ is the viscosity of the suspension carrier medium, and $\phi$ is the volume fraction of the solutes or particles. To aid with the conceptual understanding, FIG. 9 presents a comparison of a conventional approach to protein delivery involving a high viscosity solution 29 (top drawing). The electrospray particle suspension technique 31 of the current invention is shown with particles 32 including a protein 33 (bottom drawing). Although this technique of the invention involves regions in which the local viscosity may be extremely high, i.e., within the particles, where the viscosity may be exceedingly large if the particle is a dry solid or concentrated liquid, the average macro-scale viscosity of the injectable suspension formulation is reasonably low, such that it may be administered with a standard injection device 28. Note that the continuous phase of the injectable suspension formulation, the carrier medium, may contain a non-zero concentration of a therapeutic or diagnostic agent. This therapeutic or diagnostic agent may or may not be the same therapeutic or diagnostic agent which is included the particles.

In other embodiments, particularly those involving high volume fraction, (p, the performance of the suspensions approximately obeys other equations such as the Krieger-Dougherty equation or the Frankel-Acrivos equation (S. Mueller, E. W. Llewellin, H. M. Mader, Proc. Royal Soc. A, 2010, 466, 1201-1228), amongst others.

In certain embodiments, the suspension formulation provides a means of enhancing the stability of certain therapeutic or diagnostic agents at a given concentration, e.g., as compared to an aqueous formulation, and improving the injectability concurrently. In other embodiments, in which the injectability is not necessarily improved, the suspension formulation enhances the stability properties of the therapeutic or diagnostic at a given concentration. In still other embodiments, powder formulations enhance the stability of certain therapeutic or diagnostic agents, e.g., as compared to an aqueous formulation.

Particle

The particles can have diameters from 0.1 to 1000 µm. For example, a range of 0.1 to 90 µm may be delivered by a 25 gauge needle. Larger particles, e.g., within the range from 90 to 230 µm, may be of use in connection with larger needles (lower gauge) or other delivery routes or modalities. A lower range of 0.1 to 1 µm is of interest in certain embodiments. The particles can have a dispersity index from 0.05 to 0.9. Methods of measuring the particle size and distribution include imaging flow cytometry and image analysis of scanning electron micrographs of the particles in which an average spherical radius or diameter is calculated on the basis of the cross-sectional areas of the particles projected onto the plane of the image.

The particles may include both a core and a shell. In some embodiments, the particles include a core but not a shell. The core is a gel core or dry solid-state core when no shell is present but may exist in the liquid state when the particles include a gel shell or dry solid-state shell. The morphology of the particles is approximately spherical, mushroom-like, or raisin-like, among potentially other morphologies (FIG. 10), depending on the properties of the electrospray feed solution and the desiccation conditions.

In some embodiments the particle surfaces may have wrinkles or crenellations.

In some embodiments, the particles exhibit a skeletal density from about 1 to 6 g/cm$^3$, e.g., from about 1 to 5 g/cm$^3$, from about 1 to 3 g/cm$^3$, from about 1 to 2 g/cm$^3$, from about 1 to 1.5 g/cm$^3$, or from about 1.1 to 1.4 g/cm$^3$. Exemplary methods of density measurements include gas displacement pycnometry.

In some embodiments, residual quantities of the first liquid in the particles after desiccation are from 0 to 10% by weight, e.g., from 0 to 5% by weight, from 0 to 3% by weight, or from 0 to 1% by weight. Exemplary methods of measuring residual solvent content include Karl Fischer titration and various weight-loss methods.

In some embodiments, the particles may exhibit a porosity from about 0 to 50%, e.g., from about 0 to 10%, from about 0 to 5%, from about 0 to 1%, from about 0 to 0.5%, from about 0 to 0.1%, or from about 0 to 0.01%. Exemplary pore size measurements include scanning electron microscopy (SEM), transmission electron microscopy (TEM), and confocal laser scanning microscopy analysis. The specific surface area of porous micro- and nanospheres may also be investigated by nitrogen adsorption/desorption analysis and a Brunauer-Emmett-Teller adsorption model. In embodiments where the pore sizes are sufficiently large, mercury-intrusion porosimetry may be employed.

In some embodiments, the particles have a residual net electrical charge of either polarity, i.e., net positive or net negative charge. In terms of magnitude, the particles may have from 0 to 10 billion charges, e.g., from 0 to 100 million charges, from 0 to 1 million charges, from 0 to 0.01 million charges, or from 0 to 100 charges. The magnitude of a charge is defined as the magnitude of charge carried by an electron, i.e., the elementary charge, $1.6 \times 10^{-19}$ Coulombs. Exemplary methods of measuring particle charge include those involving the analysis of particle motion in response to an externally applied electric field. In some cases, this is done while particles are suspended in an insulating liquid such as oil.

In certain embodiments, the therapeutic or diagnostic agents have a zeta potential from about −90 to 90 mV; e.g., from about −60 to 60 mV, from about −40 to 40 mV, from about −20 to 20 mV, or from about −5 to 5 mV. Exemplary methods of measuring zeta potential include reconstituting the therapeutic or diagnostic agents by dissolving the particles in water and analyzing the solution by electrophoretic light scattering. This is similar to a dynamic light scattering (DLS) measurement which is performed in the presence of a positive or negative electric field.

In some embodiments, insoluble particulate matter with characteristic sizes greater than or equal to 1 μm persist upon reconstitution of the particles of the invention. These are sometimes referred to as subvisible particles (SvPs). SvPs are present in quantities from about 0 to 100,000,000 per mL, e.g., from 0 to 10,000,000 per mL, from 0 to 1,000,000 per mL, from 0 to 500,000 per mL, from 0 to 100,000 per mL, from 0 to 50,000 per mL, from 0 to 10,000 per mL, from 0 to 6,000 per mL, from 0 to 1,000 per mL, from 0 to 600 per mL, from 0 to 250 per mL, from 0 to 100 per mL, from 0 to 60 per mL, or from 0 to 10 per mL. In some embodiments, the count of particles with characteristic size greater than or equal to 10 μm is from 0 to 6,000 per mL, e.g., from 0 to 1,000 per mL, from 0 to 100 per mL, from 0 to 10 per mL, from 0 to 5 per mL, from 0 to 3 per mL, or from 0 to 1 per mL. In some embodiments, the count of particles with characteristic size greater than or equal to 25 μm is from 0 to 600 per mL, e.g., from 0 to 100 per mL, from 0 to 10 per mL, from 0 to 3 per mL, from 0 to 1 per mL, from 0 to 0.5 per mL, or from 0 to 0.1 per mL. Exemplary methods of measuring SvPs include analysis of the therapeutic or diagnostic agent with a Coulter Counter, HIAC Royco, or micro-flow imaging system after reconstitution and dilution of the therapeutic or diagnostic agent to a concentration of about 1 mg/mL.

In some embodiments, the dose will be administered by small volume injection (SVI). In some such embodiments, the total count of SvPs exhibiting a characteristic size greater than or equal to 10 μm within the container from which the SVI is to be administered is from 0 to 6,000, e.g., from 0 to 3,000, from 0 to 1,000, from 0 to 500, from 0 to 100, from 0 to 50, or from 0 to 10. In some embodiments, the total count of SvPs exhibiting a characteristic size greater than or equal to 25 μm within the container from which the SVI is to be administered is from 0 to 600, e.g., from 0 to 300, from 0 to 100, from 0 to 50, from 0 to 10, from 0 to 5, or from 0 to 1. Exemplary methods of measuring the total count of insoluble particle matter in a container include removing the dose from the container, reconstituting or dissolving the particles of the invention comprising the dose, diluting the therapeutic or diagnostic agent to a suitable concentration, e.g., 1 mg/mL, and counting all insoluble particulate matter by light obscuration or light microscopy methods, among potentially others. Such methods include analysis with a Coulter Counter, HIAC Royco, or micro-flow imaging system. In certain embodiments, the method of administering a first therapeutic or diagnostic agent is by administering a composition comprising particles made by electrospray as described herein.

In some embodiments, the particles include a loading of therapeutic or diagnostic agents from 1 to 100 wt %, e.g., from 50 to 100 wt %, from 75 to 100 wt %, from 90 to 100 wt %, from 95 to 100 wt %, from 99 to 100 wt %, or from 99.9 to 100 wt %. At these loadings the therapeutic or diagnostic agents retain from 0.5 to 1.0 activity during electrospray particle formation, e.g., from 0.75 to 1.0 activity, from 0.9 to 1.0 activity, from 0.95 to 1.0 activity, from 0.99 to 1.0 activity, or from 0.999 to 1.0 activity. This includes the activity retained through primary desiccation and, in some cases, secondary desiccation.

In some embodiments, the dissolution or reconstitution of the particles provides less than a 10% increase in aggregates of the diagnostic or therapeutic agent, e.g., a protein, (e.g., less than 8%, less than 5%, less than 4%, less than 3%, or less than 1%) as compared to the therapeutic or diagnostic agent in the first liquid prior to processing. Exemplary methods of measuring aggregates include size exclusion high-performance liquid chromatography (SEC-HPLC), where the aggregate population is quantified by dividing the area under the peak corresponding to the aggregate population by the cumulative area contained beneath all peaks in the sample spectrum. Changes in aggregate percentage between two samples, e.g., Sample A and Sample B, are computed as the numerical difference in the respective aggregate percentages, i.e., by subtracting the aggregate percentage of Sample B from the aggregate percentage of Sample A, or vice versa.

In some embodiments, the dissolution or reconstitution of the particles provides less than a 10% increase in fragments of the diagnostic or therapeutic agent, e.g., a protein, (e.g., less than 8%, less than 5%, less than 4%, less than 3%, or less than 1%) as compared to the therapeutic or diagnostic agent in the first liquid prior to processing. Exemplary methods of measuring fragments include size exclusion high-performance liquid chromatography (SEC-HPLC), where the fragment population is quantified by dividing the area under the peak corresponding to the fragment population by the cumulative area contained beneath all peaks in the sample spectrum. Changes in fragment percentage between two samples, e.g., Sample A and Sample B, are computed as the numerical difference in the respective fragment percentages, i.e., by subtracting the fragment percentage of Sample B from the fragment percentage of Sample A, or vice versa.

In some embodiments, the process of particle formation provides less than a 50% change in charge variants in the population of a diagnostic or therapeutic agent, e.g., an antibody, (e.g., less than 40, 30, 20, 10, 8, 5, 4, 3, or 1%) as compared to the therapeutic or diagnostic agent prior to particle formation. Charge variants may be acidic, basic, or neutral, and the variation may be caused post-translation modifications at terminal amino acids, such as asparagine deamidation or lysine glycation. For example, charge variants include the loss of a positive charge by the loss of a C-terminal lysine residue, covalent bonding of the amine portions of two lysine residues by reducing sugars, or the conversion of an N-terminal amine to a neutral amide by the cyclization of N-terminal glutamines. Negative charges on proteins, e.g., antibodies, can appear by the conversion of asparagine residues to aspartic acid and/or isoaspartic residues via a deamidation reaction. Exemplary methods of measuring charge variants include cation exchange chromatography (CIEX), where the variants are quantified by dividing the area under the peak corresponding to the variant, e.g., acidic, basic, or natural population by the cumulative area contained beneath all peaks in the sample spectrum. Changes in charge variant population percentage between two samples, e.g., Sample A and Sample B, are computed as the numerical difference in the respective population variant percentages, i.e., by subtracting the specific variant, e.g., acidic, percentage of Sample B from the specific variant, e.g., acidic, percentage of Sample A, or vice versa. This analysis may be extended similarly for all variants within a population.

In some embodiments, the particles are flowable. The Hausner ratio may be from 1.0 to greater than 3.0, e.g., from 1.0 to 3.0, from 1.0 to 2.0, from 1.0 to 1.70 (e.g., very poor), from 1.0 to 1.59, from 1.0 to 1.35, from 1.0 to 1.25, or from 1.0 to 1.11 (e.g., excellent). Exemplary methods of measuring the flowability of a powder include the tapped density method (Carr R L. Chem. Eng., 1965; 72:163-168). Bulk density may be first be obtained by adding a known mass of powder to a graduated cylinder. The density can be calculated as mass/volume. The same sample may then be mechanically tapped until further volume change is not observed. The tapped density can then be calculated as mass divided by the final volume of the powder. A comparison of tapped and bulk density may be used to index the ability of the powder to flow. In particular, the Hausner ratio (unsettled apparent volume or bulk volume, $V_0$, divided by the final tapped volume, $V_t$) is a measure of the product's ability to settle and permits an assessment of the relative importance of interparticulate interactions. These interactions are less significant in free flowing powders. The bulk and tapped densities for such free flowing powders are close in value, such that the Hausner ratio is close to 1.0.

In some embodiments, the particles have one or more of the following characteristics: a size from 1 to 50 µm; a solid core; a gel or solid shell; a density from 1 to 1.5 g/cm$^3$; a residual solvent content from 0 to 3 wt %; a porosity from 0 to 10%; a net electrical charge of either polarity, i.e., positive or negative charge, from 0 to 1 million charges; therapeutic or diagnostic components with a zeta potential from −60 to 60 mV; SVPs from 0 to 1,000,000 per mL upon reconstitution; a therapeutic or diagnostic agent loading from 50 to 100 wt % in which the activity of the therapeutic or diagnostic agents is from 0.9 to 1.0 upon reconstitution; less than 10% aggregates upon reconstitution; and/or a Hausner ratio between 1.0 and 1.35, or between 1.0 and 1.11.

Particles can be stored and formulated for delivery in various devices. In some embodiments, the device is a subcutaneous administration device, such as a pre-filled syringe. In some embodiments, the invention provides a method of making an article of manufacture including filling a container with a suspension formulation. The container in the article of manufacture may include syringes (e.g., pre-filled syringes), autoinjectors, bottles, vials (e.g., dual chamber vials), and test tubes. The container may hold the suspension formulation, and the label on, or associated with, the container may indicate directions for use. The article of manufacture may further include other materials desirable from a commercial and user standpoint, including, e.g., other buffers, diluents, filters, needles, syringes, and package inserts with instructions for use.

Particle Core

The core of each particle, e.g., formed from the first liquid, typically includes one or more therapeutic or diagnostic agents. The core is a solid-state dry core when no shell is present but may exist in the liquid state when the particle includes a gel shell or solid-state dry shell. When a shell is present, the shell may include the therapeutic or diagnostic agent, while the core does not.

The therapeutic or diagnostic agent or agents may be dissolved or suspended in the electrospray feed solution, a first liquid, prior to particle formation. The concentration of the therapeutic or diagnostic agent in the first liquid can be in the range of 0.0001 to 1000 mg/mL. The liquid can be aqueous or an organic solvent, a hydrogel, an ionogel, or a combination thereof. The liquid is, for example, water, 0.9% saline, lactated Ringer's solution, dextrose 5%, or a buffer. In some embodiments, the buffer is acetate buffer, histidine buffer, succinate buffer, HEPES buffer, tris buffer, carbonate buffer, citrate buffer, phosphate buffer, glycine buffer, barbital buffer, and cacodylate buffer. Organic solvents, hydrogels, and ionogels are described herein. The liquid can further include, e.g., a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, and/or nutrient media. In some embodiments, the liquid may further include a paraben, a bactericide, a fungicide, a preservative, or a vitamin. For example, oligopeptides, e.g., trileucine, can be used as stabilizers for particles. In some cases, the liquid can further include an analgesic, such as acetaminophen or lidocaine. In some embodiments, each of the other components is, independently, at 0.0001 to 99% (w/v) of sprayed liquid, e.g., at 0.0001 to 90% (w/v), at 0.0001 to 50% (w/v), at 0.0001 to 10% (w/v), at 0.0001 to 1% (w/v), or at 0.0001 to 0.1% (w/v). One of ordinary skill in the art would be able to determine an appropriate amount of the other components in the sprayed liquid. In some embodiments, the carbohydrate is dextran, trehalose, sucrose, agarose, mannitol, lactose, sorbitol, or maltose. In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. In some embodiments, the salt is sodium chloride, calcium chloride, potassium chloride, sodium hydroxide, stannous chloride, magnesium sulfate, sodium glucoheptonate, sodium pertechnetate, or guanidine hydrochloride. In some embodiments, the chelator is disodium edetate or ethylenediaminetetraacetic acid (EDTA). In some embodiments, the mineral is calcium, zinc, or titanium dioxide. In some embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), or polylactic acid. In some embodiments, the surfactant is polysorbate, magnesium stearate, sodium dodecyl sulfate, polyethylene glycol nonylphenyl ether (TRITON™ N-101), glycerin, or polyoxyethylated castor oil. In some embodiments, the protein stabilizer is acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids (e.g., an oligopeptide), hydroxyethylstarch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, or mannitol. The paraben can be a parahydroxybenzoate. The bactericide can be benzalkonium chloride. In some embodiments, the emulsifier is selected from polysorbate 80, polysorbate 20, sorbitan monooleate, sorbitan monopalmitate, sorbitan monostearate, sorbitan tristearate, sorbitan trioleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In preferred embodiments, the emulsifier can be polysorbate 80 or sorbitan monooleate. In some embodiments, the antiseptic is phenol, m-cresol, benzyl alcohol, 2-phenyloxyethanol, chlorobutanol, neomycin, benzethonium chloride, gluteraldehyde, or beta-propiolactone. In some embodiments, the amino acid is alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, or glutamine, e.g., asparagine, L-arginine, histidine, glycine, or glutamine, or any combination thereof. In some embodiments, the antioxidant is glutathione, ascorbic acid, cysteine, or tocopherol. In some embodiments, the protein is protamine, protamine sulfate, or gelatin. In some embodiments, the organic solvent may be dimethyl sulfoxide or N-methyl-2-pyrrolidone. In some embodiments, the preservative is methyl hydroxybenzoate, thimerosal, parabens, formaldehyde, or castor oil. In some embodiments, the liquid can further include adenine, tri-n-butyl phosphate, octa-fluoropropane, white petrolatum, or p-aminophenyl-p-anisate. In some embodiments, the organic solvent may be dichloromethane, dimethyl sulfoxide, urea, sarcosine, methanol, formic acid, acetic acid, ethyl acetate, acetonitrile, acetone, methyl acetate, diethyl ether, hydrazine, ethyl nitrate, butanol, dimethoxyethane, methyl tert-butyl ether, triethylamine, or any combination thereof.

Particle Shell

Generally, any excipient is suitable as a shell material. Exemplary excipients include, but are not limited to, sugars, salts, and amino acids. Therapeutic agents, diagnostic agents, and biocompatible polymers may also be used to form the shell. This includes small molecule drugs. Non-limiting examples of hydrophilic biocompatible polymers include poly(vinyl alcohol), poly(acrylic acid), poly(acrylamide), poly(ethylene oxide), or co-polymers or combinations of any two or more of them. Hydrophilic polymers may be modified to adjust their characteristics. The shell component may alternatively or additionally include one or more biocompatible hydrophobic polymers. Hydrophobic polymers may be modified to adjust their characteristics. Non-limiting examples of hydrophobic polymers include polycaprolactam, poly(lactic acid), poly(glycolic acid), polycaprolactone, PLGA or co-polymers, or combinations of any two or more of them. In some embodiments, a PLGA (50:50) polymer is used as a shell to encapsulate a therapeutic, e.g., antibody, in an amount just below its solubility limit. The polymer also may be prepared as a function of PLGA at various lactic acid-glycolic acid ratios, as well as be co-polymer with other polymers, e.g., chitosan, cellulose, etc.

The thickness of the particle shell may range from 0 to 90% of the diameter of the particle in some embodiments. The shell does not have to be uniform of fully formed for encapsulation. In some embodiments the interface between the shell and the core is partially blended, such that a clear line of demarcation does not exist. Moreover, one or more therapeutic or diagnostic agents, as described herein, can be included in the particle shell. The therapeutic or diagnostic agents can be the same or different as those in the core. The concentration of the therapeutic or diagnostic agent in the shell may be in the range 0.0001 to 2000 mg/mL (or crystalline density of the therapeutic or diagnostic agent, if higher).

Core-Shell Ratio

For those embodiments in which the particle includes a shell, a core-shell volume ratio between 1:99 vol % and 99:1% are expected to be most useful, e.g., about 10:90 vol % or about 90:10 vol % or about 95:5 vol %. Complete coverage is not always required for sufficient encapsulation. In certain circumstances, e.g., for highly concentrated cores, thick shells can be beneficial. The core-shell ratio may be useful in the modulation of the release kinetics of the therapeutic or diagnostic agent or agents. In certain embodiments, it is advantageous to have a polydisperse system, e.g., for lowering the viscosity of a suspension formulation. In this instance a variety of core-shell ratios may be of interest.

Electrospray Particle Formation

Electrospray is a process by which droplets of a first liquid are formed in a dielectric medium in the presence of an electric field. Exemplary dielectric media include vacuo, air, a second liquid that is a suitable electrical insulator in which the first liquid is at least partially immiscible, and combinations thereof. The first liquid does not need to be electrically conductive, and the droplets do not need to possess net electrical charge (e.g., droplets can be formed from electrically insulating liquids, such as oils). Furthermore, the electric field acting on the first liquid need not be the primary driving force behind the formation of the droplets. In some embodiments, droplets are formed primarily on account of electrostatic interactions between the first liquid and the electric field, such as in conventional electrospray. In other embodiments, the electric field acts to assist in the formation of droplets by a primary droplet formation device, playing an ancillary role and in some instances modifying the properties of the droplets. Devices include rotary atomizers, pneumatic nozzle atomizers, ultrasonic nozzle atomizers, sonic nozzles, microfluidic T-junctions, microfluidic Y-junctions, microcapillaries, etc. In all embodiments, the electric field is effectuated by enforcing a potential difference between the first liquid and an electrode which is disposed in the dielectric medium.

The potential difference between the location at which droplets are first produced and the electrode, as measured within the dielectric medium separating the electrospray source and the electrode, is from 0.001 and 100,000 V, e.g., from 1 to 50,000 V, 100 to 25,000 V, or 1,000 to 10,000 V. As a fraction of the Rayleigh limit, the droplets in this field may on average be charged from 0 to 1, e.g., from 0.1 to 1.0, from 0.2 to 1.0, from 0.3 to 1.0, from 0.4 to 1.0, or from 0.5 to 1.0. In some embodiments the droplets are charged to beyond the Rayleigh limit to induce Coulomb fission. The droplets can be desiccated through any of several techniques known throughout the literature and then collected for use. Exemplary collectors include, but are not limited to, electrode plates (N. Bock, T. R. Dargaville, M. A. Woodruff, Prog. Polym. Sci., 2012, 37, 1510-1551), liquid baths (FIGS. 2, 3, 5, 6) (U.S. Pat. No. 8,939,388), electrostatic precipitators (Y. A. Haggag, A. M. Faheem, Front. Pharmacol., 2015, 6, 140), and cyclones (J. Bogelein, G. Lee, Int. J. Pharm., 2010, 401, 68-71).

The electrospray technique is perhaps most widely known for its utilization in biological mass spectrometers (J. Fenn, M. Mann, C. Kai Meng, S. Fu Wong, and C. M. Whitehouse, Science, vol. 246, no. 4926, pp. 64-71, October 1989), where its properties of soft atomization have helped to enable the analysis of molecules with high molecule weight. The canonical electrospray apparatus includes a tube and an electrode which are coordinated such that one end of the tube is located at a distance from the electrode (FIG. 1). The tube carries a flow of liquid that is driven by a displacement pump, e.g., a syringe pump, or a source of pressurized gas, e.g., a compressed gas bottle. A power supply charges the liquid in the tube relative to the electrode, creating an electric field in the region between the distal end of the tube and the electrode. Charges accumulate in the liquid meniscus at the end of the tube in proportion to the strength of this field (FIG. 7). When the field reaches a certain critical strength, the force of electrostatic traction acting on the charge is sufficient to overcome the surface tension forces of the meniscus (FIG. 8). In some embodiments, this results in a morphologically stable reconfiguration of the meniscus that is typified by a cone with a half-angle of about 49.2 degrees. This so-called Taylor cone, characteristic of conventional electrospray droplet formation, anchors at its tip a thin jet which extends briefly toward the electrode as it breaks into a train of uniform charged droplets. These droplets propagate toward the electrode through the agency of the field before they are eventually intercepted. In other embodiments, the increase in electrostatic traction over surface tension forces results in a pulsating meniscus that produces droplets via dripping. During each cycle of pulsation, the meniscus extends towards the electrode in the form of a jet that eventually detaches from the base of the meniscus. The detached jet forms either a single droplet or breaks into an ensemble of droplets as the meniscus recoils in preparation for a subsequent cycle. In still other embodiments, disparate modes of electrospray prevail. The exact mode through which electrified droplets are produced is generally dependent upon at least the conductivity, polarizability, viscosity, surface tension coefficient of the electrosprayed liquid, and electric field geometry (M. Cloupeau and B. Prunet-Foch, Electrostatic spraying of liquids: Main functioning modes, J. Electrostatics, 25, 165-184, 1990; M. Cloupeau and B. Prunet-Foch, J. Aerosol Sci., vol. 25, no. 6, pp. 1021-1036, 1994).

In some embodiments, the electrospray technique is utilized by complementing an atomizer, a microfluidic device, or some other primary drop formation device with an electric field to form electrospray droplets. In some embodiments, this can reduce the amount of energy that the primary device contributes to the formation of each drop. In the instance of an ultrasonic atomizer, e.g., the presence of the electric field may in some cases reduce the minimum power required by the ultrasonic generator to produce drops. This can be advantageous in that it mitigates select effects, e.g., cavitation, which may have an impact on the integrity of certain therapeutic or diagnostic agents in the first liquid (S. Vonhoff, The Influence of Atomization Conditions on Protein Secondary and Tertiary Structure During Microparticle Formation by Spray-Freeze-Drying, PhD Thesis, Univ. of Erlangen-Nuremberg, 2010). In certain embodiments, the electric field may similarly reduce the average droplet size and/or narrow the droplet dispersity relative to what can be achieved in its absence.

Desiccation of the droplets, i.e., removal of the first liquid to produce dry particles, is performed through any of several methods known throughout the art. These include, but are not limited to, warm gas evaporation, freeze drying, critical point drying, emulsion solvent evaporation, emulsion solvent diffusion (as described in U.S. Pat. Nos. 8,013,022 and 8,512,754), and combinations thereof. In some embodiments, the primary desiccation step is followed by a secondary desiccation step such as lyophilization or vacuum desiccation intended to further reduce residual quantities of the first liquid within the particles. In some embodiments, residual quantities of the first liquid in the particles after primary or secondary desiccation are from 0 and 10% by weight, e.g., from 0 to 5% by weight, from 0 to 3% by weight, from 1 to 3% by weight, or from 0 to 1% by weight.

In some embodiments, the agency of the electric field is such that a reversible or irreversible charge is induced on the therapeutic or diagnostic agents in a droplet of the first liquid, i.e., the agents are ionized (Anal. Chem., 2005, 77, 5370). This effect may be modulated by controlling certain electrospray parameters such as the size of the drops and their composition. In some embodiments, the inclusion of certain excipients, e.g., amino acids, stabilizes the charged therapeutic or diagnostic agents. In other embodiments, the excipient carries the charge preferentially, such that the therapeutic or diagnostic agents are less susceptible to ionization. In some embodiments, charge on the drops is reduced or even completely neutralized during desiccation and/or contact between the particle and an electrode. In other embodiments, portions of this charge are intentionally preserved by preventing direct contact between the particle and an electrode.

In some embodiments, the agency of the electric field is such that free charges and/or polar molecules move to the surface of the droplet of the first liquid preferentially on account of Coulombic effects. The former phenomenon, the localization of free charges at the interface between the first liquid and the dielectric medium in which the droplets are formed, produces a layer of surface charge. In some embodiments, such effects are leveraged to influence the structure and/or surface properties of the droplet and/or particle. This includes instances in which the surface charge is used to achieve spherical particle morphologies under conditions in which they would not otherwise be readily accessible. In some embodiments, e.g., coordination of the first liquid, which may be polar, near the surface of the droplet facilitates faster removal of the first liquid and in some cases at lower temperatures. The ability to reach low residual moisture content with primary desiccation may also be improved. This may be particularly beneficial when desiccating with a warm gas stream, where the temperature of the gas stream is in some cases correlated with degradation of the therapeutic or diagnostic agents. It may also be beneficial when desiccating electrosprayed drops in a collection bath, e.g., a bath of supercritical carbon dioxide, where localization of the first liquid near the surface may promote greater particle sphericity and/or mitigation of surface-related degradation events among the therapeutic or diagnostic agents and/or potentially other advantageous effects.

In some embodiments, the agency of the electric field is such that free charges and/or polar molecules move to the surface of the droplet of the first liquid preferentially on account of Coulombic effects, and the therapeutic or diagnostic agent crystallizes. Crystal nucleation of the agent may be controlled to obtain a desired polymorph preferentially (A. Ziabicki, L. Jarecki, Macromolecular Symposia, 1996, 104, 65-87).

In some embodiments, core-shell particles are produced by coaxial electrospray (FIG. 4). In this case a second liquid including a dissolved encapsulant or shell material is provided with the first liquid during electrospraying. This is typically achieved by flowing the second liquid through an annular tube that is coordinated coaxially with respect to a tube through which the first liquid flows. At end of this coaxial tube arrangement, an electrospray is formed in which droplets include a core of the first liquid and a shell of the second liquid. Desiccation of the droplets may proceed through any of the usual pathways. In other embodiments, core-shell particles are formed from an electrospray of only a first liquid by leveraging the proclivity of certain polar molecules and free charges to arrange themselves at the surface of the droplet. In certain instances, this produces a localization of the therapeutic or diagnostic agents, either towards the core of the droplet or its surface, that can be preserved during desiccation. In some embodiments, this involves a deterministic stratification of various agents (e.g., therapeutic agents, diagnostic agents, excipients) throughout the thickness of the particle. In certain embodiments, non-therapeutic components, such as a salt (e.g., NaCl) or a sugar (e.g., sucrose) are driven to the surface, preferentially with the electric field, to form a thin shell around the particle, crystalline or otherwise. This shell may have protective effects or provide a measure of control over pharmacokinetics. In other embodiments, portions of the agents may be localized at the particle surface without necessarily forming a uniform or continuous shell (FIG. 22, FIG. 23).

In preferred embodiments, the composition comprising particles is formed using electrospray as described herein.

Therapeutics

Exemplary therapeutic or diagnostic agents are nucleic acids, oligonucleotides, antibodies (or an antibody fragment, e.g., a bispecific fragment, a trispecific fragment, Fab, F(ab')$_2$, or a single-chain variable fragment (scFv)), amino acids, peptides, proteins, cells, bacteria, gene therapeutics, genome engineering therapeutics, epigenome engineering therapeutics, carbohydrates, chemical drugs, contrast agents, magnetic particles, polymer beads, metal nanoparticles, metal microparticles, quantum dots, antioxidants, antibiotic agents, hormones, nucleoproteins, polysaccharides, glycoproteins, lipoproteins, steroids, analgesics, local anesthetics, anti-inflammatory agents, anti-microbial agents, chemotherapeutic agents, exosomes, outer membrane vesicles, vaccines, viruses, bacteriophages, adjuvants, vitamins, minerals, organelles, and combinations thereof (Table 1). Therapeutic and diagnostic agents may have a molecular weight of 20 to 200 kDa, e.g., 40 to 150 kDa. The concentration of the therapeutic or diagnostic agent in the droplet is typically at least 1 mg/mL, e.g., at least 5 mg/mL, at least 10 mg/mL, at least 50 mg/mL, at least 100 mg/mL, or at least 500 mg/mL. The first therapeutic or diagnostic agent in the particles may have 0.5 to 1.0 activity per unit, 0.75 to 1.0 activity per unit, 0.9 to 1.0 activity per unit, 0.95 to 1.0 activity per unit, or 0.99 to 1.0 activity per unit. Activity is measured relative to the same therapeutic or diagnostic agent prior to being electrosprayed.

TABLE 1

Various therapeutic and diagnostic agents in the particles and their concentrations.

| Therapeutic/diagnostic agent | Concentration range (mg/mL) |
|---|---|
| proteins | 20-1500 (e.g., 20-600) (or crystalline density, if higher) |
| peptides | 20-1500 (e.g., 20-600) (or crystalline density, if higher) |
| chemical drugs | 0.0001-2000 (e.g., 0.0001-1000) (or crystalline density, if higher) |

TABLE 1-continued

Various therapeutic and diagnostic agents in the particles and their concentrations.

| Therapeutic/diagnostic agent | Concentration range (mg/mL) |
|---|---|
| magnetic particles | 0.001-5400 (e.g., 0.001-500) (iron oxide density) |
| carbohydrates | 0.001-400 |
| nucleic acids | 0.001-100 |

In some embodiments of any of the foregoing methods, the therapeutic and diagnostic agent is an antibody or an antibody fragment, e.g., a bispecific fragment, a trispecific fragment, Fab, F(ab')$_2$, or a single-chain variable fragment (scFv). In some embodiments, the antibody or fragment is 3F8, Abagovomab, Abciximab, Abituzumab, Abrilumab, Acritumomab, Actoxumab, Adalimumab, Adalimumab-atto, Adecatumumab, Ado-trastuzumab emtansine, Aducanumab, Afasevikumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, Crotedumab, CR6261, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Inebilizumab, Infliximab, Infliximab-dyyb, Intetumumab, Inolimomab, Inotuzumab ozogamicin, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Mavrilimumab, Matuzumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tildrakizumab, Tigatuzumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, Zolimomab aritox, 8H9, Abrezekimab, Aprutumab ixadotin, Atidortoxumab, Azintuxizumab vedotin, Belantamab mafodotin, BCD-100, Berlimatoxumab, Bersanlimab, Birtamimab, BIVV009, BMS-986016, Cetrelimab, Cibisatamab, Cosfroviximab, Cusatuzumab, Dezamizumab, DS-8201, Enapotamab vedotin, Etigilimab, Faricimab, FBTA05, Gancotamab, Gosuranemab, GSK2831781, lanalumab, IBI308, Ifabotuzumab, Iladatuzumab vedotin, Imaprelimab, Infliximab-abda, Infliximab-qbtx, Iomab-B, Iscalimab, Istiratumab, Lacnotuzumab, Ladiratuzumab vedotin, Larcaviximab, Lenvervimab, Leronlimab, Lesofavumab, Letolizumab, Loncastuximab tesirine, Losatuxizumab vedotin, Lupartumab amadotin, Lutikizumab, MABp1, Marstacimab, Modotuximab, Mosunetuzumab, Naxitamab, NEOD001, Netakimab, Netakimab, Oleclumab, Olendalizumab, OMS721, Onvatilimab, Otilimab, PDR001, Ravagalimab, Ravulizumab, Remtolumab, Romilkimab, Rozanolixizumab, SA237, Samrotamab vedotin, Setrusumab, SHP647, Sirtratumab vedotin, Spartalizumab, Suptavumab, Sutimlimab, Suvratoxumab, Talacotuzumab, Tavolimab, Telisotuzumab vedotin, Tepoditamab, Tibulizumab, Timigutuzumab, Tiragotumab, Tislelizumab, Tomuzotuximab, TRBSO7, Vanalimab, Varisacumab, Vonlerolizumab, Vopratelimab, Vunakizumab, XMAB-5574, Zenocutuzumab, or Zolbetuximab.

In some embodiments, the antibody or fragment is 8H9, Abrezekimab, Aprutumab ixadotin, Atidortoxumab, Azintuxizumab vedotin, Belantamab mafodotin, BCD-100, Berlimatoxumab, Bersanlimab, Birtamimab, BIVV009, BMS-986016, Cetrelimab, Cibisatamab, Cosfroviximab, Cusatuzumab, Dezamizumab, DS-8201, Enapotamab vedotin, Etigilimab, Faricimab, FBTA05, Gancotamab, Gosuranemab, GSK2831781, lanalumab, 1B1308, Ifabotuzumab, Iladatuzumab vedotin, Imaprelimab, Infliximab-abda, Infliximab-qbtx, Iomab-B, Iscalimab, Istiratumab, Lacnotuzumab, Ladiratuzumab vedotin, Larcaviximab, Lenvervimab, Leronlimab, Lesofavumab, Letolizumab, Loncastuximab tesirine, Losatuxizumab vedotin, Lupartumab amadotin, Lutikizumab, MABp1, Marstacimab, Modotuximab, Mosunetuzumab, Naxitamab, NEOD001, Netakimab, Netakimab, Oleclumab, Olendalizumab, OMS721, Onvatilimab, Otilimab, PDR001, Ravagalimab, Ravulizumab, Remtolumab, Romilkimab, Rozanolixizumab, SA237, Samrotamab vedotin, Setrusumab, SHP647, Sirtratumab vedotin, Spartalizumab, Suptavumab, Sutimlimab, Suvratoxumab, Talacotuzumab, Tavolimab, Telisotuzumab vedotin, Tepoditamab, Tibulizumab, Timigutuzumab, Tiragotumab, Tislelizumab, Tomuzotuximab, TRBS07, Vanalimab, Varisacumab, Vonlerolizumab, Vopratelimab, Vunakizumab, XMAB-5574, Zenocutuzumab, or Zolbetuximab.

In some embodiments, the therapeutic is an immunotherapy. In some embodiments, the immunotherapy is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In some embodiments, the immunotherapy is a PD-1 inhibitor (e.g., nivolumab, pembrolizumab, pidilizumab, BMS 936559, and MPDL328OA). In some embodiments, the immunotherapy is a PD-L1 inhibitor (e.g., atezolizumab and MEDI4736). In some embodiments, the immunotherapy is a CTLA-4 inhibitor (e.g., ipilimumab). In some embodiments, the immunotherapy is a CSF-1R inhibitor (e.g., pexidartinib and AZD6495). In some embodiments, the immunotherapy is an IDO inhibitor (e.g., norharmane, rosmarinic acid, and alpha-methyl-tryptophan). In some embodiments, the immunotherapy is an A1 adenosine inhibitor (e.g., 8-cyclopentyl-1, 3-dimethylxanthine, 8-cyclopentyl-1,3-dipropylxanthine, 8-phenyl-1,3-dipropylxanthine, bamifylline, BG-9719, BG-9928, FK-453, FK-838, rolofylline, or N-0861). In some embodiments, the immunotherapy is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241,385). In some embodiments, the immunotherapy is an A2B adenosine inhibitor (e.g., ATL-801, CVT-6883, MRS-1706, MRS-1754, OSIP-339,391, PSB-603, PSB-0788, or PSB-1115). In some embodiments, the immunotherapy is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In some embodiments, the immunotherapy is an arginase inhibitor (e.g., an arginase antibody, (2S)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapy is an HDAC inhibitor (e.g., valproic acid, SAHA, or romidepsin). In some embodiments, the immunotherapy is a toll-like receptor activator. In some embodiments, the immunotherapy is a RIG-1-like receptor activator. In some cases, the immunotherapy is a stimulator of interferon genes (STING) pathway activator. In some embodiments, the immunotherapy is an Interleukin-1 receptor agonist, e.g., an IL-R1 antagonist. In some embodiments, the immunotherapy is a PTEN inhibitor, e.g., a bisperoxovanadium compound. In some embodiments, the immunotherapy is a tumor necrosis factor receptor (TNFR), e.g., TNFR-1 or TNFR-2 inhibitor. In some embodiments, the immunotherapy is a Lymphocyte-activation gene 3 (LAG-3) inhibitor, e.g., GSK2831781.

In some embodiments, the therapeutic can be ledipasvir/sofosbuvir, insulin glargine, lenalidomide, pneumococcal 13-valent conjugate vaccine, fluticasone/salmeterol, elvitegravir/cobicistat/emtricitabine/tenofovir alafenamide, emtricitabine, rilpivirine and tenofovir alafenamide, emtricitabine/tenofovir alafenamide, grazoprevir/elbasvir, coagulation factor VIIa recombinant, epoetin alfa, Aflibercept or etanercept.

In some embodiments, the therapeutic or diagnostic agents is Abatacept, AbobotulinumtoxinA, Agalsidase beta, Albiglutide, Aldesleukin, Alglucosidase alfa, Alteplase (cathflo activase), Anakinra, Asfotase alfa, Asparaginase, Asparaginase *Erwinia chrysanthemi*, Becaplermin, Belatacept, Collagenase, Collagenase *clostridium histolyticum*, Darbepoetin alfa, Denileukin diftitox, Dornase alfa, Dulaglutide, Ecallantide, Elosulfase alfa, Etanercept-szzs, Filgrastim, Filgrastim-sndz, Galsulfase, Glucarpidase, Idursulfase, IncobotulinumtoxinA, Interferon alfa-2b, Interferon alfa-n3, Interferon beta-1a, Interferon beta-1b, Interferon gamma-1b, Laronidase, Methoxy polyethylene glycol-epoetin beta, Metreleptin, Ocriplasmin, OnabotulinumtoxinA, Oprelvekin, Palifermin, Parathyroid hormone, Pegaspargase, Pegfilgrastim, Peginterferon alfa-2a, Peginterferon alfa-2a co-packaged with ribavirin, Peginterferon alfa-2b, Peginterferon beta-1a, Pegloticase, Rasburicase, Reteplase, Rilonacept, RimabotulinumtoxinB, Romiplostim, Sargramostim, Sebelipase alfa, Tbo-filgrastim, Tenecteplase, or Ziv-aflibercept.

In some embodiments, the diagnostic agent is tuberculin purified protein derivative, hyrotropin alpha, secretin, soluble transferrin receptor, troponin, B-type natriuretic peptide, iobenguane 1123, florbetapir F 18, perflutren, gadoterate meglumine, florbetaben F 18, flutemetamol F 18, gadoterate meglumine, isosulfan blue, regadenoson, technetium Tc 99m tilmanocept, florbetaben F 18, perflutren, regadenoson, or flutemetamol F 18.

Formulations

The electrosprayed particles can be suspended in a non-aqueous or aqueous liquid or gel (or a mixture thereof) to form a suspension formulation. The non-aqueous liquid can be an organic solvent or an ionic liquid or some combination thereof. In some embodiments, the organic solvent is benzyl alcohol, benzyl benzoate, corn oil, coconut oil, cottonseed oil, fish oil, grape seed oil, hazelnut oil, hydrogenated vegetable oils, olive oil, palm seed oil, peanut oil, peppermint oil, safflower oil, sesame oil, soybean oil, sunflower oil, walnut oil, castor oil, polyoxyl 40 hydrogenated castor oil, polyoxyl 35 castor oil, simple alcohols such as ethanol, octanol, hexanol, decanol, propanol, and butanol, gamma-butyrolactone, acetone, ethyl acetate, ethyl lactate, dimethylacetamide, dimethyl isosorbide, dimethyl sulfoxide, glycofurol, diglyme, tocopherol, methyl tert-butyl ether, N-methyl pyrrolidone, perfluorodecalin, octa-fluoropropane, (perfluorohexyl)octane, polyethylene glycol, 2-pyrrolidone, n-acetyltryptophan, tetrahydrofurfuryl alcohol, triglycerides, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, fatty acid esters, propanoic acid, hexanoic acid, octanoic acid, triacetin, citral, anisole, anethol, benzaldehyde, linalool, caprolactone, phenol, thioglycerol, dimethylacetamide, TRANSCUTOL® HP (diethylene glycol monoethyl ether), solketal, isosorbide dimethyl ether, ethyl formate, ethyl hexyl acetate, diethyl glycol monoether, gamma-butyrolactone, eugenol, clove bud oil, citral, limonene, and any combination thereof. In some embodiments, the ionic liquid includes pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6^-$, $BF_4^-$, triflate, nonaflate, bis(trifyl)amide, trifluoroacetate, heptafluorobutanoate, haloaluminate, or any combination thereof. Aqueous liquids for suspension include water, 0.9% saline, lactated Ringer's solution, dextrose 5% or a buffer. The buffer may include, e.g., acetate buffer, histidine buffer, succinate buffer, HEPES buffer, tris buffer, carbonate buffer, citrate buffer, phosphate buffer, glycine buffer, barbital buffer, and cacodylate buffer. The medium for suspension may further include another component, such as, e.g., a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, or nutrient media. In certain embodiments, the suspension further comprises an analgesic, e.g., acetaminophen. In some embodiments, each of the other components is, independently, at 0.0001 to 99% (w/v) of the medium, e.g., at 0.0001 to 90% (w/v), at 0.0001 to 50% (w/v), at 0.0001 to 10% (w/v), at 0.0001 to 1% (w/v), or at 0.0001 to 0.1% (w/v). One of ordinary skill in the art would be able to determine an appropriate amount of the other components in the medium.

Carbohydrates dextran, trehalose, sucrose, agarose, mannitol, lactose, sorbitol, or maltose. The pH adjusting agent may be, e.g., acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. Exemplary salts are sodium chloride, calcium chloride, potassium chloride, sodium hydroxide, stannous chloride, magnesium sulfate, sodium glucoheptonate, sodium pertechnetate, or guanidine hydrochloride. The chelator can be, e.g., disodium edetate. The mineral can be, e.g., calcium, zinc, or titanium dioxide. Examples of polymers are propyleneglycol, glucose star polymer, silicone polymer, polydimethylsiloxane, polyethylene glycol, carboxymethylcellulose, poly(glycolic acid), poly(lactic-co-glycolic acid), or polylactic acid. The surfactant may be, e.g., polysorbate, magnesium stearate, sodium dodecyl sulfate, TRITON™ N-101 (polyethylene glycol nonylphenyl ether), glycerin, or polyoxyethylated castor oil. Protein stabilizers include acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids (e.g., an oligopeptide), hydroxyethylstarch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, or mannitol. The paraben can be a parahydroxybenzoate. The bactericide can be benzalkonium chloride. The emulsifier can be, e.g., polysorbate 80, polysorbate 20, sorbitan monooleate, sorbitan monopalmitate, sorbitan monostearate, sorbitan tristearate, sorbitan trioleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In preferred embodiments, the emulsifier can be polysorbate 80 or sorbitan monooleate. Exemplary antiseptics include phenol, m-cresol, benzyl alcohol, 2-phenyloxyethanol, chlorobutanol, neomycin, benzethonium chloride, gluteraldehyde, or beta-propiolactone. The amino acid may be alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, or glutamine, e.g., asparagine, L-arginine, histidine, glycine, or glutamine, or a combination thereof. The antioxidant can be glutathione, ascorbic acid, cysteine, or tocopherol. The protein can be protamine, protamine sulfate, or gelatin.

For aqueous suspension formulations, high concentration trehalose solutions can stabilize the particles in suspension and prevent premature dissolution. The sugar acts as a "crowder" molecule, i.e., a crowding agent, that occupies a large volume, increasing short range protein-protein attractive interactions in some embodiments. This stabilizing effect has also been described for other crowding agents in water such as (i) polymers, e.g., PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, and hydroxyethylstarch, etc. (note that these may be used alone or in combination); (ii) organic molecules, e.g., N-methyl-2-pyrrolidone (Miller et al. J. Pharm. Sci., 2012, 101, 3763-3778), and (iii) sugars and sugar alcohols such as sorbitol, sucrose, and mannitol, among others.

The viscosity of the suspension can range from 0.27 to 200 cP, e.g., 0.27 to 50 cP, 1 to 30 cP, or 20 to 50 cP. In some embodiments, the viscosity of the suspension ranges from 0.27 to 200 cP, e.g., 0.27 to 100 cP, 0.27 to 50 cP, 0.27 to 30 cP, 1 to 20 cP, or 1 to 15 cP. In certain embodiments, the viscosity is measured at a shear rate in the Newtonian regime. In other embodiments, the viscosity is measured at a shear rate of 100 $s^{-1}$ or greater, e.g., at 1000 $s^{-1}$ or greater than 1000 $s^{-1}$. The suspension may include from 5 to 90% particles by volume, e.g., 20 to 90%, 40 to 80%, 50 to 60%, or 70 to 90%. The suspension may have a concentration of the first therapeutic or diagnostic agent from 0.0001 to 1000 mg/mL, e.g., from 100 to 900, 150 to 800, or 200 to 700 mg/mL.

In some embodiments of the invention described herein, high concentrations of therapeutic or diagnostic agents in the particles and high concentrations of particles in the non-aqueous or aqueous liquid are possible. The latter may be achieved by mixing particles of various sizes.

In some embodiments, one or more therapeutic or diagnostic agents can be in the particles and outside of the particles, i.e., in the non-aqueous or aqueous liquid. The therapeutic or diagnostic agent included in the non-aqueous or aqueous liquid can be the same or different than that employed in the particle. The one or more therapeutic or diagnostic agent can reduce pain or inflammation during administration. The concentration of the therapeutic agent in the pharmaceutical composition outside of the particles can range, e.g., from 0.0001 to 1000 mg/mL.

In some embodiments, the particles are sprayed and collected for use in a needle-free injector or in an inhalation or other nasal delivery system. In some embodiments, the particles are stored as a dry powder. In some embodiments, the dry powder is reconstituted shortly before administration of a formulation in which the therapeutic or diagnostic agents are dissolved in an aqueous or non-aqueous solution. Such a paradigm is beneficial in some cases for circumventing the relative instability or degradation of certain therapeutic or diagnostic agents stored in an aqueous or non-aqueous solution form, rather than a dry powder form.

Needle-free injection systems may involve administration of liquids, suspensions, powders, or projectiles. Exemplary needle-free injection systems include those made by Portal Instruments and PharmaJet (Stratis), among others. Powders are suitable for long term storage and can be injected at home without reconstitution or extensive user preparation using such systems. Needle-free injection system incorporating powders often require an injection chamber filled with solid drug and a nozzle for firing the solid drug particles into the skin. In brief, in some embodiments, the particles exit the nozzle with a gas stream and impinge the skin surface. This leads to small perforations or holes in which the particles are deposited. They penetrate the stratum corneum before being distributed completely into the stratum corneum and viable epidermis. Particles for needle-free injection may have a density from 0.1 to 5 g/$cm^3$ (e.g., in the case of magnetic nanoparticle inclusion), e.g., from 0.1 to 2.5 g/$cm^3$, from 0.1 to 1.4 g/$cm^3$, from 0.5 to 1.4 g/$cm^3$, or from 1.0 to 1.4 g/$cm^3$. The mean diameter greater of the particles can be from 1 to 100 μm, e.g., from 4 to 100 μm, from 10 to 100 μm, or from 20 to 50 μm.

In some embodiments, the particles are administered via a dual-chamber syringe device such as LYOTWIST™. The particles exist as a dry powder in one chamber of the device while the second chamber is occupied by an aqueous or non-aqueous carrier liquid. The components of the two chambers are mixed briefly before administration.

In other embodiments, the composition comprising particles is formed by electrospray as described herein.

Methods of Use

The pharmaceutical compositions including suspensions or dry forms of the invention may be administered in a suitable dosage that may be adjusted as required, depending on the clinical response. Compositions may also be used cosmetically. The dosage of the pharmaceutical composition can vary depending on many factors, such as the pharmacokinetics of the therapeutic or diagnostic agents; the mode of administration; the age, health, and weight of the recipient; the nature and extent of the symptoms; the frequency of the treatment, and the type of concurrent treatment, if any; and the clearance rate of the therapeutic or diagnostic agents in the animal to be treated. One of skill in the art can determine the appropriate dosage based on the above factors. Administration may occur daily, weekly, every two weeks, every three weeks, monthly, or any other suitable interval. In general, satisfactory results may be obtained when the therapeutic or diagnostic agent is administered to a human at a dosage of, for example, between 0.01 mg/kg and 70 mg/kg (measured as the solid form). In some embodiments, the dosage may range from 0.01 mg/kg to 1 mg/kg. Dose ranges include, for example, between 30 mg and 5000 mg. In some embodiments, at least 30, 100, 500, 1000, 2000, or 5000 mg of the compound is administered. Preferred dose ranges include, for example, between 1-30 mg/kg, such as 1-10 mg/kg.

The volume delivered will depend on the indication and the route of delivery. In one embodiment, a dose of more than 0.5 mL, e.g., more than 2 mL, of a pharmaceutical composition having a viscosity less than 50 cP, e.g., less than 30 cP, is administered, e.g., injected into skin of an animal. In some embodiments, a dose of more than 1.5 mL, e.g., more than 5 mL, of a pharmaceutical composition having a viscosity less than 50 cP, e.g., less than 30 cP, is administered, e.g., injected into skin of an animal.

The pharmaceutical composition may be administered by any suitable method, for example, by auricular, buccal, conjunctival, cutaneous, dental, electro-osmotical, endocervical, endosinusial, endotracheal, enteral, epidural, extraamniotical, extracorporeal, infiltration, interstitial, intra-abdominal, intra-amniotical, intra-arterial, intra-articular, intrabiliary, intrabronchial, intrabursal, intracameral, intracardial, intracartilaginous, intracaudal, intracavernous, intracavitary, intracerebral, intracisternal, intracorneal, intracoronal, intracoronary, intracorporus cavernosum, intradermal, intradiscal, intraductal, intraduodenal, intradural, intraepidermal, intraesophageal, intragastrical, intragingival, intrailleal, intralesional, intraluminal, intralymphatical, intramedullar, intrameningeal, intramuscular, intraocular, intraovarian, intrapericardial, intraperitoneal, intrapleural, intraprostatical, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastrical, occlusive dressing technique, ophthalmical, oral, oropharyngeal, parenteral, percutaneous, periarticular, peridural, perineural, periodontal, rectal, inhalation, retrobulbar, soft tissue, subarachnoidial, subconjunctival, subcutaneous, sublingual, submucosal, topical, transdermal, transmucosal, transplacental, transtracheal, transtympanic, ureteral, urethral, or vaginal administration and the pharmaceutical compositions formulated accordingly. In certain embodiments, the composition is administered by small volume injection (SVI). In preferred embodiments, the pharmaceutical composition is administered by small volume injection (SVI).

In certain embodiments, the method of administering a first therapeutic or diagnostic agent is by administering a composition comprising particles formed by electrospray as described herein.

The disclosure generically described, will be more readily understood by reference to the following examples, which are included merely for purposes of illustration of certain aspects and embodiments of the present disclosure, and are not intended to be limiting.

EXAMPLES

The methods disclosed herein have been utilized in separate instances to produce particles including bovine serum albumin (BSA), particles including whole human IgG, and particles including one of three discrete monoclonal antibodies. Various analytical techniques have been applied to assess the physical characteristics of the particles themselves and the structural and functional properties of the proteins they include. Scanning electron microscopy and associated image analysis have been used to study the particle morphology and size distribution, respectively. Smooth particles of high sphericity were achieved for certain excipient profiles while facile control of the mean size was possible over a broad range with low dispersity. In certain instances, the particle surfaces were decorated with excipients. Density and water content measurement demonstrated that the particles approached crystalline packing efficiencies and retained very low levels of residual moisture, particularly in instances in which secondary desiccation was employed. The functional properties of the proteins were also preserved, as evidenced by ELISA and binding assays performed on reconstituted particles. This was corroborated by size exclusion HPLC analysis indicating that the process had a minimal or even remedial effect on the degree of inter-protein association. Finally, suspension of the particles in various carrier media showed that ultra-high loadings, e.g., >300 mg/mL, were possible, and the apparent viscosity of the particle-medium complex was below 20 cP.

Materials and Methods

Bovine serum albumin and human IgG were obtained from Sigma-Aldrich (A2934, >98%) and Innovative Research (IRHUGGF-LY, >97%), respectively, as lyophilized powders. Biosimilar versions of three marketed monoclonal antibody products (mAb1, mAb2, mAb3) were obtained in aqueous solution. The formulations were congruent with the corresponding FDA label. Concentration columns were procured from Millipore Sigma (Amicon® Ultra 15 mL Filters for Protein Purification and Concentration with a 3 kDa cut off) and used where necessary to reach the desired protein concentration for the electrospray feed solution. All excipients and the carrier medium, benzyl benzoate, were purchased from Sigma-Aldrich and used as received.

The mAb was purchased as an aqueous formulation of 10 mg/mL mAb, 9 mg/mL sodium chloride, 7.35 mg/mL sodium citrate dihydrate, and 0.7 mg/mL polysorbate 80. Formulation of custom "feed solutions" used for processing particles were produced through modifying the formulation by desalting followed by concentrating and adding desired excipients.

Electrospray Particle Formation

Unless otherwise noted, a conventional electrospray apparatus of custom design was used to prepare the particle samples disclosed herein. This apparatus comprised a 30-gauge blunt disposable syringe needle (89134-196, VWR International) attached to a Harvard Apparatus Model 33 dual-channel syringe pump. The needle was charged by a Matsusada EQ-30P1-LCtG high voltage DC power supply. For select samples, the needle was replaced by a Sono-Tek 120 kHz ultrasonic atomizer nozzle driven at a power of 4.5 W.

Lyophilization

The particles for lyophilized samples, i.e., samples marked as having gone through secondary desiccation, were loaded into microcentrifuge tubes and subjected to snap freezing by immersion in liquid nitrogen for approximately 10 min. The samples were then loosely covered and transferred to a Labconoco Freezone lyophilizer for approximately 48 hours at a pressure of approximately 0.035 Torr.

Scanning Electron Microscopy

Electron micrographs were collected for select samples with a Hitachi TM3030Plus tabletop microscope. The samples were immobilized on conductive tape and examined in a low-vacuum anti-charging environment, obviating the need for sample preparation.

Optical Microscopy

Select samples were prepared for imaging by vortexing 5 mg of particles with benzyl benzoate (20 microliters). Samples were then pipetted onto a glass slide and imaged using a Celena microscope by Logos Biosystems.

Image Analysis

Select microscopy images were chosen for further analysis on the basis of (i) minimal particle overlapping, (ii) good contrast between the particles and the background, and (iii) a resolution providing for particle occupancies of at least 10 pixels. This allowed for particles to be easily identified and reduced resolution-based error. A binary threshold was applied to separate the particles from background, and a watershed segmentation algorithm was applied to ensure that individual particles were measured separately. The ImageJ tool "Analyze Particles" was then applied on the binary picture with the following parameters: circularity between 0.5 and 1.0; size between 5 and infinity square microns; exclude on edges; fill holes. The outlines of the identified particles were overlaid onto the original image. Particles which were misidentified, such as clusters that were identified as a single particle or particles whose outlines do not match the particle, were then discarded. Missing particles were measured by manually tracing the particle's outline and using ImageJ's Measure tool.

Density Analysis

The skeletal density of electrosprayed particles from select samples was determined by examining approximately 0.1 g of powder with an AccuPyc II 1340 gas displacement pycnometry system.

Water Content Analysis

The residual moisture in electrosprayed particles from select samples was determined by placing approximately 0.1 g of powder in a vacuum oven with a Karl Fischer titrator and heating the sample.

Salt Content Analysis

The salt content of electrosprayed particles from select samples was determined by elemental analysis for chlorine. This was performed by flask combustion followed by ion chromatography.

Zeta Potential Analysis

Zeta potential analysis was carried out on select samples using a Malvern Instruments ZetaSizer Nano. ZS. Solutions were made up at 8 mg/mL in DI water and placed in a Malvern Instruments INC DTS1070 folded capillary cell.

ELISA Assay

ELISA assay was used on select samples to detect human antibody in a denaturation sensitive manner. Human IgG was first plated in PBS for 1 hour, followed by washing with wash buffer (PBS+0.05% Tween20) three times for 4 minutes, followed by blocking with 2% BSA (Sigma) in wash buffer for 45 minutes, followed incubation with dilute (20μg/mL) protein A-HRP (Abcam) for 45 minutes, followed by wash buffer three times for 3 minutes, followed by incubation with TMB (Abcam) for 10 minutes, finally followed by quenching of the reaction with STOP solution (Abcam). The colorimetric readout was conducted on a Thermo Multiskan Spectrum.

Monoclonal Antibody Binding Assay

Monoclonal antibodies from select samples were assessed for cellular binding ability utilizing cells that express the appropriate cell surface receptors. Cells were incubated for 30 minutes at 4° C. with monoclonal antibodies at respective concentrations and then spun down at 2000 rpm followed by washing with PBS three times. Cells were then incubated with secondary goat anti-human Fab antibody fluorescently labeled with PE for 30 minutes at 4° C. The cells were then spun down at 2000 rpm followed by washing with PBS three times. The cells were then re-suspended and then analyzed on an Attune Flow Cytometer (Invitrogen).

Size Exclusion Chromatography

The quantification of size variants in select samples was determined by size exclusion chromatography. This analysis utilized Advanced BioSEC), column, 7.8 mm ID×30 cm, 3 μm (Agilent) run on an HPLC system (1100, Agilent). The mobile phases were 0.2 M potassium phosphate and 0.25 M potassium chloride at pH 6.0. The chromatography was run isocractically at a flow rate of 1.0 mL/min for 15 minutes. The column temperature was maintained at ambient 25° C. and the eluent absorbance was monitored at 280 nm. Each monoclonal antibody was diluted with its respective formulation buffer to 1 mg/mL. Their injection volume was 20 μL.

Suspension Preparation

For select samples, particles were weighed in a 2-mL Eppendorf Microcentrifuge tube. Based on the measured powder density, the appropriate amount of suspension vehicle was added to prepare a suspension of the desired concentration. Samples were then vortexed for 30 seconds.

Viscosity Measurement

The viscosities of solutions and suspensions were measured through the use of an AR-G2 rheometer (TA Instruments) with a cone and plate geometry (20 mm/2°). The samples were measured every 30 seconds for 5 minutes at a shear rate of 1000 per second. In certain instances, the intrinsic viscosity factor [η] was calculated on the basis of the measurements. This was an indication of the extent to which particles contributed to the viscosity of the suspension. It was computed from the Krieger-Dougherty equation:

$$\eta_{rel} = \left(1 - \frac{\phi}{\phi_m}\right)^{-[\eta]\phi_m}$$

where $\eta_{rel}$ is the apparent viscosity of the suspension normalized by the viscosity of the suspension medium, $\phi$ is the volume fraction of particles in suspension, and $\phi_m$ is the maximum feasible volume fraction for the particles (approximately 0.6 in theory and approximately 0.5 in practice (M. A. Miller, J. D. Engstrom, B. S. Ludher, K. P. Johnston, Langmuir, 2010, 26, 1067)). The value of [η] was typically above the limiting value of 2.5 dL/g, the so-called Einstein value, depending on the effects of particle shape, electro-viscosity, and solvation.

FlowCam

Particle sizing was measured using FlowCam; a dynamic image analysis instrument. Samples were diluted to ~1 mg/mL in isopropanol and passed through a thin channel. Images of particles were recorded and analyzed according to size and shape.

Aging Protocol

All samples were transferred to Wheaton E-Z ex-traction round-bottom glass vials for aging (2 mL or 4 mL volume, depending on sample). The glass vials were sealed with parafilm, placed in an oven at 40° C., and visually inspected on a daily basis over the aging period to ensure integrity.

Particle Dissolution

Phosphate-buffered saline (PBS) was added to dry particle samples to produce a final concentration of 10 mg/mL (particle mass/mL of solution). Samples were placed on a VWR angular rocker with a speed setting of "35" and angle setting of "15". At 1, 10, 20, 30, 40, 50, 60, 90, and 120 minutes a 10 uL aliquot was removed from the sample vial and the absorbance at 280 nm was measured and recorded. The Rituximab concentration was plotted against time for all samples.

Salt Content

Salt Content was Recorded by Measuring Sodium Content Using ICP-OES (Inductively Coupled plasma optical emission spectroscopy). A calibration curve was prepared using a sodium standard (ICPTraceCERT, 1000 mg/L). Quality control was completed using a diluted standard solution at 100 ppm Na. A sample of particles (~15 mg) dissolved in 2 vol % nitric acid (10 mL) was then analyzed, resulting in an intensity lower than the instrument detection limit of ~0.5 ppm for sodium. This indicated a sodium content of less than 0.034 wt % and a total salt content (assuming sodium citrate and sodium chloride to have been removed equally) of less than 0.1 wt %.

Size Exclusion Chromatography (SEC) Measurements 20 uL injections of samples (1 mg/mL) were run at a flow rate of 1 mL/min in SEC buffer (25 mM phosphate, 250 mM NaCl pH 6.8) for 15 minutes on an Agilent AdvanceBio SEC (300 mm×2.7 µm, 300 Å column). Peak analysis was performed by auto-integrating using the following parameters: slope sensitivity=0.5, peak width=0, height reject=0, area reject=0, shoulders off, area percent reject 0, standard tangent skim mode, advanced baseline correction, 0 for front peak skim height ratio, 0 for tail peak skim height ratio, 0 for peak to valley ratio, and 0 for skim valley ratio.

Cation Exchange Chromatography (CIEX) Measurements

Charge variant analysis was performed for each sample on days 0, 7 and 30 under accelerated storage conditions, using an Agilent BioMAb NP5, 4.6×250 mm, PEEK ion exchange column. Samples were prepared at 1 mg/mL concentration after overnight dialysis in water. Buffer A was prepared with: 30 mM phosphate, pH: 6.3, and NaCl: 0 mM. Buffer B was prepared with: Buffer A: 30 mM phosphate, pH 6.3 plus NaCl: 175 mM. The samples were run in a gradient starting with 100% Buffer A, ramping up to a 100% Buffer B over a course of 20 min, after which the gradient was set to return to 100% Buffer A and 0% Buffer B in the next 1 min. The system re-equilibrated in 100% Buffer A for 10 min before the injection of the next sample. Integration was performed as a manual skim peak mode to reflect the Agilent data in the following protocol: https://www.agilent.com/cs/library/applications/5991-5557EN.pdf Results and Discussion Particle Size, Shape, and Chemical Composition 4 mL of BSA solution was prepared in deionized water at a concentration of about 80 mg/mL. The solution was electrosprayed with a flow rate of 0.4 mL/hr and an applied voltage of about 13.3 kV. After primary desiccation and optical microscopy, ImageJ analysis indicated a mean particle size of 19.95 µm with a dispersity index of 0.27 (FIG. 11).

3 mL of desalted IgG solution was prepared at a concentration of 50 mg/mL by exchanging PBS buffer solution with deionized water through the use of a concentration column. The solution was electrosprayed with a flow rate of 0.4 mL/hr and an applied voltage of 10.6 kV. After primary desiccation and SEM imaging, ImageJ indicated a mean particle size of 18.06 µm with a dispersity index of 0.12 (FIG. 12). Salt content was found to be less than 1.5 wt % (note that the initial PBS buffer contained NaCl at around 8 g/L). The particle density and water content after primary desiccation were 1.324 g/mL and 7-10 wt %, respectively. A residual moisture content of less than 3 wt % was achieved after implementation of a secondary desiccation step.

5 mL of desalted mAb solution was prepared at a concentration of about 20 mg/mL by exchanging a buffer solution with deionized water in a concentration column. The solution was electrosprayed with a flow rate of about 0.4 mL/hr and an applied voltage of about 11.8 kV. After primary drying and optical microscopy, ImageJ analysis indicated a mean size of 16.02 µm with a dispersity index of 0.09 (FIG. 13).

Aggregate Analysis 1 mL of a solution of mAb1 at a concentration of 20 mg/mL with an excipient at a concentration of 8 mg/mL was prepared at pH 6.5 (feed solution). The solution was electrosprayed at a flow rate of 0.4 mL/hr with an applied voltage of 11.9 kV. Aggregate analysis was performed by HPLC after (i) primary desiccation, (ii) secondary desiccation, (iii) and storage at accelerated conditions (7 days, 40° C.). The size distribution of aggregates was compared to those observed in both the feed solution and the label formulation. After seven days of accelerated storage, the particle formulation had about 0.2% fewer aggregates than the label formulation when stored under similar conditions (see Table 2 below).

TABLE 2

| Formulation | % Monomers | % Aggregates |
|---|---|---|
| Label | 96.8 | 3.2 |
| Feed | 96.6 | 3.4 |
| Electrosprayed t = 0 w/ primary desiccation | 97.3 | 2.7 |
| Electrosprayed t = 0 days w/ secondary desiccation | 96.6 | 3.4 |
| Label t = 7 days | 95.7 | 4.3 |
| Electrosprayed t = 7 days | 95.9 | 4.1 |

IgG Function by ELISA Assay

A solution of IgG at a concentration of 50 mg/mL was electrosprayed at a flow rate of about 0.4 mL/hr with an applied voltage of 10.6 kV. Particles were reconstituted in PBS after primary desiccation so that the IgG contained therein could be analyzed by ELISA assay. FIG. 15 shows that the signal for the reconstituted IgG was equivalent to that of the control sample in FIG. 14, indicating that the binding activity for the Fc (constant) domain of the electrosprayed protein was preserved.

Cellular Binding Activity (In Vitro Indicator for Therapeutic Activity) for mAb1 and mAb2

A solution of mAb1 at a concentration of 20 mg/mL was electrosprayed at a flow rate of about 0.4 mL/hr with an applied voltage of 11.8 kV. A second solution of mAb2 at a concentration of 20 mg/mL was electrosprayed at a flow rate of about 0.4 mL/hr with an applied voltage of 11.9 kV. The particles were subjected to primary desiccation. In FIG. 16 and FIG. 17, the binding activities of the label formulations for mAb1 and mAb2 are shown, as assessed by flow cytometry. Thermal denaturation controls and a negative mAb control with no affinity for the target expressed by the cell line indicated that the assay was sensitive to thermal denaturation and selectivity. Particles including mAb1 (FIG. 16) and particles including mAb2 (FIG. 17) were then reconstituted in PBS and assayed for binding activity. The results indicated that full binding activity of the antibodies was preserved through the electrospray particle formation process.

In FIG. 18, the thermal stability of mAb1 particles was assessed over a seven-day period of accelerated storage at 40° C. The particles were split into two samples, one stored as a dry powder and the other stored in benzyl benzoate. The particles were reconstituted in PBS after storage, at which point the flow cytometry assay again indicated preservation of the cellular binding activity as compared to unprocessed material (label formulation) without storage.

Viscosity of an IgG Particle Suspension

Particles of desalted IgG and mAb1 were prepared by electrospray as described above. These particles were individually suspended in benzyl benzoate and analyzed on a rheometer at a shear rate of approximately 1000 per second. Both suspensions exhibited similar rheological behavior and substantially outperformed an aqueous formulation of mAb1 (FIG. 19). Suspension formulations of greater than 300 mg/mL of either agent were observed to have an apparent viscosity below approximately 20 cP. Moreover, IgG particles in suspension at 500 mg/mL were found to have a $[\eta]$ value of about 2.64 dL/g, indicating that the viscosity was primarily governed by excluded volume effects. This is to be compared against aqueous solutions of various proteins in which intermolecular interactions can significantly contribute to the apparent viscosity of the medium, e.g., aqueous IgG is typified by $[\eta]$ values near 6.5 dL/g (E. Longman, S. E. Harding, N. Mareineke, LCGC North America, 2006, 24, 1, 64-72).

Comparison of Human IgG Particles Produced with and without an Electric Field

Particles of human IgG were produced by drying the drops of an aerosol of aqueous IgG (approximately 16 mg/mL IgG, 4 mg/mL NaCl) which was generated by an ultrasonic nozzle. The aerosol formation for one group of particles (Group A) was assisted by an electric field (FIG. 20), applied by enforcing an 8 kV bias between the nozzle and an electrode stationed several centimeters downstream, and for another group it was not (Group B) (FIG. 21).

The mean sizes of the particles in Groups A and B were 6.5 and 10.1 μm, respectively, indicating that the electric field acted to reduce the average drop size. The standard deviations were 1.8 and 3.4 μm, respectively. The particles were then reconstituted in water and analyzed via HPLC. Aggregates were found to be 7.9% (Group A) and 6.9% (Group B) of the protein populations, as compared to 14.1% aggregates in the feed solution. The zeta potentials for the same reconstituted material were 3.95 mV (Group A) and 6.91 mV (Group B).

Surface Prominent Excipients in Human IgG Particles Produced by Electrospray

A solution of human IgG at about 80 mg/mL and a salt at about 30 mg/mL was electrosprayed at a flow rate of 0.4 mL/hr with an applied voltage of 12.2 kV. Particles were produced after primary desiccation of the drops and visualized with SEM (FIG. 22, FIG. 23). Crystalline or semi-crystalline salt was observed at the surface of the particles in large quantities.

A solution of human IgG at about 80 mg/mL, a salt at about 20 mg/mL, and a sugar at about 10 mg/mL was electrosprayed at a flow rate of 0.4 mL/hr with an applied voltage of 12 kV. Particles were produced after primary desiccation of the drops and visualized with SEM (FIG. 24, FIG. 25). The salt and/or sugar was observed at the surface of the particles in large quantities.

A solution of monoclonal antibody comprising mAb3 at about 70 mg/mL and a sugar at about 46 mg/mL was electrosprayed at a flow rate of 0.4 mL/hr with an applied voltage of 12.1 kV. Particles were produced after primary desiccation of the drops and visualized with SEM (FIG. 26, FIG. 27). The sugar was observed at the surface of the particles in large quantities.

Protein Structure and Stability (Days 0, 7, 30 at 40° C.) after Particle Formation by Structural Assays Size Exclusion Chromatography (SEC)

FIG. 28 shows a collection of SEC data collected to assess the degradation of the monomers through processing and storage at 40° C. for 30 days. SEC was performed on the FDA-label, particles, and suspensions. The monomer, aggregate, and fragment data for each sample is summarized in FIG. 28. The SEC data demonstrates good stability of monomers through processing and storage on day 0, 7, and 30 after storage at 40° C. The 30-day sample for the FDA label had poor preservation of the monomers as compared to the particle and formulations including a suspension of particles of the invention, which each had >98% preservation of monomers. The small increase in aggregates through processing of particles can be addressed through improved formulation.

Improved Formulation

FIGS. 29A-29B shows a series of studies showing SEC data of Formulations A and B. An additional formulation was studied with lower polysorbate and higher salt content which reduced the small initial increase in aggregates and fragmentation after the particle processing step (FIG. 29B). FIG. 29A shows results from a formulation described in FIG. 28. FIG. 29B shows results from an improved formulation and processing procedure which showed no significant structural loss. FIGS. 29A-29B shows that the initial damage was reduced through a slight modification of the formulation through lowering the amount of polysorbate 80 and reintroducing a fraction of the salt removed through desalting. The data indicates an almost unmeasurable difference in aggregates and fragmentation and very little monomer change through processing. Thus, Formulation B demonstrates lower accumulation of aggregates (~0.1%) through processing, whereas formulation A accumulated more aggregates (~2-2.5%).

Cation Exchange Chromatography (CIEX)

FIG. 30A shows a collection of CIEX data on Days 0, 7, and 30. The CIEX data was collected to assess the distribution of charge variant species and their changes through processing and storage at 40° C. for 30 days. CIEX was performed on the FDA-label, particles, and suspensions. The acidic, main, and basic species data for each sample is summarized in FIG. 30A and shows a strong acidic shift in aqueous "Label" after 30-days of storage. Select CIEX plots are presented in FIG. 30B which highlights the acidic shift (arrows) experienced by the label formulation compared to the absence of such a shift in the solid particles of the invention after 30 days of storage. The particles resemble the unprocessed material whereas the label formulation experiences degradation. The CIEX data in FIG. 30B demonstrates good stability of charge variants through processing and storage on day 0, 7, and 30 after storage at 40° C. The 30-day sample for the FDA-label had a drastically poorer preservation of the charge variant distribution as compared to the particle and the formulations including a suspension of particles of the invention due to the acidic shift in variants.

Sub-Visible Particle Analysis

FIG. 31 shows the result of an subvisible particle analysis of the subvisible particle matter present in dissolved particles of the invention. Subvisible particle analysis was performed after dissolution of the technology. The data shown in FIG. 31 demonstrates a low particle count which is adjusted for background signal in the control sample. The subvisible particle count measured in the sample of particles of the invention was found to be less than observed for standard spray dry technologies.

2.5 mL of monoclonal antibody was prepared at 25 mg/mL in a sugar buffer (15 mg/mL) and placed in a syringe. The flow rate of the solution was set to 0.1 mL/min and this flowed through an atomizer into a solvent bath. The bath contained 400 mL of butyl acetate and 400 mg of SPAN 80 (sorbitan monooleate) surfactant. The solution was stirred and was connected to a power supply set to −10 kV. Atomized droplets were collected and dehydrated in the bath. After all droplets had dehydrated the resulting particles were collected via filtration and dried in vacuo for 20 hrs. This experiment was repeated in a bath containing no surfactant. The particles were dissolved in deionized water to a protein concentration of 50 mg/mL and analysis showed a reduction in subvisible particle matter.

Other embodiments are in the claims.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific aspects and embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A method of electrospraying an aqueous first liquid comprising a protein to form droplets and removing the aqueous first liquid to produce particles from the droplets, wherein the protein in the particles has 0.5 to 1.0 activity per unit, wherein after electrospraying, the particles are suspended in a non-aqueous liquid, thereby forming a suspension, wherein the particles in suspension have less than 10% aggregation of the protein.

2. The method of claim 1, wherein the particles in suspension have less than 10% fragmentation of the protein.

3. The method of claim 1, wherein the particles in suspension have less than 50% change in charge variants of the protein compared to the protein prior to particle formation.

4. The method of claim 1, wherein the suspension further comprises insoluble particulate matter larger than or equal to 1 μm.

5. The method of claim 4, wherein the number of insoluble particles is from 0 to 100,000,000 per mL.

6. The method of claim 4, wherein the number of insoluble particles greater than 10 μm is from 0 to 6,000 per mL.

7. The method of claim 4, wherein the number of insoluble particles greater than 25 μm is from 0 to 600 per mL.

8. The method of claim 1, wherein the particles have diameters from 0.1 to 1000 μm.

9. The method of claim 1, wherein the particles have a polydispersity index from 0.05 to 0.9.

10. The method of claim 1, wherein the concentration of the protein in the aqueous first liquid is from 0.0001 to 1000 mg/mL.

11. The method of claim 1, wherein the aqueous first liquid is selected from the group consisting of water, 0.9% saline, lactated Ringer's solution, dextrose 5%, or a buffer.

12. The method of claim 1, wherein the aqueous first liquid further comprises a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, or a nutrient media.

13. The method of claim 1, wherein the non-aqueous liquid is an organic solvent.

14. The method of claim 13, wherein the organic solvent is selected from the group consisting of benzyl benzoate, coconut oil, cottonseed oil, fish oil, grape seed oil, hazelnut oil, hydrogenated vegetable oils, olive oil, palm seed oil, peanut oil, peppermint oil, safflower oil, sesame oil, soybean oil, sunflower oil, walnut oil, acetone, ethyl acetate, ethyl lactate, dimethylacetamide, dimethyl isosorbide, dimethyl sulfoxide, glycofurol, diglyme, methyl tert-butyl ether, N-methyl pyrrolidone, perfluorodecalin, polyethylene glycol, 2-pyrrolidone, tetrahydrofurfuryl alcohol, trigylcerides, triglycerides of the fractionated plant fatty acids C8 and C10, propylene glycol diesters of saturated plant fatty acids C8 and C10, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, and limonene or any combination thereof.

15. The method of claim 13, wherein the organic solvent is selected from the group consisting of polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, diethylene qlycol monoethyl ether, solketal, isosorbide dimethyl ether, ethyl formate, and ethyl hexyl acetate.

16. The method of claim 1, wherein the suspension has viscosity from 0.27 to 200 cP.

17. The method of claim 1, wherein the suspension comprises from 5 to 90% particles by volume.

18. The method of claim 1, wherein the suspension has a concentration of the protein from 0.0001 to 1000 mg/mL.

19. The method of claim 1, wherein the protein is selected from the group consisting of antibodies or fragment thereof, nucleoproteins, glycoproteins, lipoproteins, and any combination thereof.

* * * * *

UNITED STATES PATENT AND TRADEMARK OFFICE
CERTIFICATE OF CORRECTION

PATENT NO. : 12,115,262 B2
APPLICATION NO. : 17/058339
DATED : October 15, 2024
INVENTOR(S) : Coffman et al.

Page 1 of 1

It is certified that error appears in the above-identified patent and that said Letters Patent is hereby corrected as shown below:

In the Claims

In Claim 15, Column 45, Line 4, delete "qlycol" and insert -- glycol --.

Signed and Sealed this
Twenty-first Day of January, 2025

Coke Morgan Stewart
*Acting Director of the United States Patent and Trademark Office*